United States Patent
Quay et al.

(10) Patent No.: US 9,074,205 B2
(45) Date of Patent: Jul. 7, 2015

(54) NICKED OR GAPPED NUCLEIC ACID MOLECULES AND USES THEREOF

(75) Inventors: Steven C. Quay, Woodinville, WA (US); James Mcswiggen, Bothell, WA (US); Narendra K. Vaish, Kirkland, WA (US); Mohammad Ahmadian, Bothell, WA (US)

(73) Assignee: Marina Biotech, Inc., New York, NY (US)

( * ) Notice: Subject to any disclaimer, the term of this patent is extended or adjusted under 35 U.S.C. 154(b) by 661 days.

(21) Appl. No.: 12/445,868

(22) PCT Filed: Oct. 18, 2007

(86) PCT No.: PCT/US2007/081836
§ 371 (c)(1),
(2), (4) Date: Apr. 16, 2009

(87) PCT Pub. No.: WO2008/049078
PCT Pub. Date: Apr. 24, 2008

(65) Prior Publication Data
US 2010/0209487 A1    Aug. 19, 2010

Related U.S. Application Data

(60) Provisional application No. 60/862,027, filed on Oct. 18, 2006, provisional application No. 60/910,393, filed on Apr. 5, 2007, provisional application No. 60/955,317, filed on Aug. 10, 2007, provisional application No. 60/969,136, filed on Aug. 30, 2007.

(51) Int. Cl.
| | |
|---|---|
| C07H 21/02 | (2006.01) |
| C07H 21/04 | (2006.01) |
| A61K 48/00 | (2006.01) |
| C12N 15/11 | (2006.01) |
| A61K 38/00 | (2006.01) |

(52) U.S. Cl.
CPC ............... *C12N 15/111* (2013.01); *A61K 38/00* (2013.01); *C12N 2310/14* (2013.01); *C12N 2310/315* (2013.01); *C12N 2310/321* (2013.01); *C12N 2310/322* (2013.01); *C12N 2320/51* (2013.01); *C12N 2330/30* (2013.01)

(58) Field of Classification Search
CPC .......................... C12N 15/111; C12N 15/113
See application file for complete search history.

(56) References Cited

U.S. PATENT DOCUMENTS

| | | | |
|---|---|---|---|
| 3,687,808 A | 8/1972 | Merigan, Jr. et al. | |
| 5,334,711 A | 8/1994 | Sproat et al. | |
| 5,627,053 A | 5/1997 | Usman et al. | |
| 5,716,824 A | 2/1998 | Beigelman et al. | |
| 5,767,264 A | 6/1998 | Otvos et al. | |
| 6,268,490 B1 | 7/2001 | Imanishi et al. | |
| 6,300,074 B1 | 10/2001 | Gold et al. | |
| 6,670,461 B1 | 12/2003 | Wengel et al. | |
| 6,794,499 B2 | 9/2004 | Wengel et al. | |
| 2004/0014956 A1 | 1/2004 | Woolf et al. | |
| 2004/0161777 A1 | 8/2004 | Baker et al. | |
| 2005/0176025 A1 | 8/2005 | McSwiggen et al. | |
| 2005/0244858 A1* | 11/2005 | Rossi et al. | 435/6 |
| 2006/0009409 A1* | 1/2006 | Woolf | 514/44 |
| 2006/0142230 A1 | 6/2006 | Quay | |
| 2007/0031844 A1 | 2/2007 | Khvorova et al. | |
| 2009/0182136 A1* | 7/2009 | Wengel et al. | 536/24.5 |
| 2009/0286852 A1* | 11/2009 | Kariko et al. | 514/44 R |

FOREIGN PATENT DOCUMENTS

| | | |
|---|---|---|
| EP | 1657312 A1 | 5/2006 |
| EP | 1849865 A1 | 10/2007 |
| WO | 9103162 A1 | 3/1991 |
| WO | 9932619 A1 | 7/1999 |
| WO | 011887 A2 | 2/2003 |
| WO | 021978 A2 | 3/2004 |
| WO | 044133 A2 | 5/2004 |
| WO | 044136 A2 | 5/2004 |
| WO | 044138 A2 | 5/2004 |
| WO | 2005028649 A1 | 3/2005 |
| WO | 056792 A1 | 6/2005 |
| WO | 2006032041 A2 | 3/2006 |
| WO | 080564 A1 | 8/2006 |
| WO | 2007048244 A2 | 5/2007 |
| WO | 2007056153 A2 | 5/2007 |
| WO | 107162 A2 | 9/2007 |
| WO | 2007107162 A2 | 9/2007 |
| WO | 2008049078 A1 | 4/2008 |
| WO | 2008109350 A2 | 9/2008 |
| WO | 2008109352 A2 | 9/2008 |

(Continued)

OTHER PUBLICATIONS

Schwarz et al., PLoS Genetics, 2006, vol. 2, Issue 9, e140, pp. 1307-1318.*

(Continued)

*Primary Examiner* — Amy Bowman
(74) *Attorney, Agent, or Firm* — Gary M. Myles; John A. Morgan; Lowe Graham Jones PLLC

(57) ABSTRACT

The present disclosure provides meroduplex (nicked or gapped) ribonucleic acid molecules (mdRNA) that decreases or silences target gene expression. An mdRNA of this disclosure comprises at least three strands that combine to form at least two non-overlapping double-stranded regions separated by a nick or gap wherein one strand is complementary to a target gene RNA. In addition, the meroduplex may have one or more modifications or substitutions, such as nucleotide base, sugar, terminal cap structure, internucleotide linkage, or any combination of such modifications. Also provided are methods of decreasing expression of a target gene in a cell or in a subject to treat a disease related to altered expression of a target gene.

22 Claims, 12 Drawing Sheets

(56) References Cited

FOREIGN PATENT DOCUMENTS

| | | |
|---|---|---|
| WO | 2008109353 A1 | 9/2008 |
| WO | 2008109354 A1 | 9/2008 |
| WO | 2008109355 A1 | 9/2008 |
| WO | 2008109356 A1 | 9/2008 |
| WO | 2008109357 A1 | 9/2008 |
| WO | 2008109358 A1 | 9/2008 |
| WO | 2008109359 A1 | 9/2008 |
| WO | 2008109361 A1 | 9/2008 |
| WO | 2008109362 A1 | 9/2008 |
| WO | 2008109364 A2 | 9/2008 |
| WO | 2008109365 A1 | 9/2008 |
| WO | 2008109366 A2 | 9/2008 |
| WO | 2008109368 A2 | 9/2008 |
| WO | 2008109369 A2 | 9/2008 |
| WO | 2008109370 A2 | 9/2008 |
| WO | 2008109371 A1 | 9/2008 |
| WO | 2008109443 A2 | 9/2008 |
| WO | 2008109447 A1 | 9/2008 |
| WO | 2008109449 A1 | 9/2008 |
| WO | 2008109450 A2 | 9/2008 |
| WO | 2008109452 A1 | 9/2008 |
| WO | 2008109454 A2 | 9/2008 |
| WO | 2008109455 A1 | 9/2008 |
| WO | 2008109456 A1 | 9/2008 |
| WO | 2008109460 A2 | 9/2008 |
| WO | 2008109461 A1 | 9/2008 |
| WO | 2008109465 A2 | 9/2008 |
| WO | 2008109468 A1 | 9/2008 |
| WO | 2008109469 A2 | 9/2008 |
| WO | 2008109470 A2 | 9/2008 |
| WO | 2008109472 A2 | 9/2008 |
| WO | 2008109473 A1 | 9/2008 |
| WO | 2008109474 A1 | 9/2008 |
| WO | 2008109475 A2 | 9/2008 |
| WO | 2008109487 A2 | 9/2008 |
| WO | 2008109488 A1 | 9/2008 |
| WO | 2008109490 A2 | 9/2008 |
| WO | 2008109492 A1 | 9/2008 |
| WO | 2008109493 A2 | 9/2008 |
| WO | 2008109494 A1 | 9/2008 |
| WO | 2008109495 A2 | 9/2008 |
| WO | 2008109497 A1 | 9/2008 |
| WO | 2008109498 A2 | 9/2008 |
| WO | 2008109500 A2 | 9/2008 |
| WO | 2008109503 A1 | 9/2008 |
| WO | 2008109505 A1 | 9/2008 |
| WO | 2008109506 A1 | 9/2008 |
| WO | 2008109509 A1 | 9/2008 |
| WO | 2008109511 A1 | 9/2008 |
| WO | 2008109516 A2 | 9/2008 |
| WO | 2008109518 A1 | 9/2008 |
| WO | 2008109520 A2 | 9/2008 |
| WO | 2008109526 A1 | 9/2008 |
| WO | 2008109531 A2 | 9/2008 |
| WO | 2008109532 A2 | 9/2008 |
| WO | 2008109534 A1 | 9/2008 |
| WO | 2008109544 A1 | 9/2008 |
| WO | 2008109546 A2 | 9/2008 |
| WO | 2008109547 A2 | 9/2008 |
| WO | 2008109548 A2 | 9/2008 |
| WO | 2008109551 A1 | 9/2008 |
| WO | 2008109555 A2 | 9/2008 |
| WO | 2008109556 A1 | 9/2008 |
| WO | 2008109558 A2 | 9/2008 |
| WO | 2008147824 A2 | 12/2008 |
| WO | 2009029293 A2 | 3/2009 |
| WO | 2010017311 A2 | 2/2010 |
| WO | 2010017319 A2 | 2/2010 |

OTHER PUBLICATIONS

Elbashir et al., The EMBO Journal, 2001, vol. 20, No. 23, pp. 6877-6888.*
Hannon et al. (Nature 431: 371-378, 2004).*
Office Action received in copending European Application No. 07844409.8, mailed Jul. 19, 2011.
Office Action, issued in U.S. Appl. No. 12/039,668, mailed Jul. 21, 2010.
Office Action, issued in U.S. Appl. No. 12/039,658, mailed Jan. 26, 2010.
Office Action, issued in U.S. Appl. No. 12/039,668, mailed Jan. 8, 2010.
Office Action, issued in U.S. Appl. No. 12/039,650, mailed Apr. 16, 2010.
Office Action, issued in U.S. Appl. No. 12/039,658, mailed Jun. 23, 2010.
Office Action, issued in U.S. Appl. No. 12/529,011, mailed Aug. 19, 2010.
Office Action, issued in U.S. Appl. No. 12/552,082, mailed Aug. 19, 2010.
Office Action, issued in U.S. Appl. No. 12/528,619, mailed Aug. 27, 2010.
Office Action, issued in U.S. Appl. No. 12/039,662 mailed Mar. 22, 2010.
Sarkar et al., "Condensation of oligonucleotides assembled into nicked and gapped duplexes: potential structures for oligonucleotide delivery," Nucleic Acids Research, 2005, vol. 33, No. 1, pp. 143-151.
International Search Report and Written Opinion, issued in International Patent Application No. PCT/US2009/052878, mailed Apr. 8, 2010.
International Preliminary Report on Patentability, issued in International Patent Application No. PCT/US2008/055360, mailed Sep. 17, 2009.
International Search Report and Written Opinion, issued in International Patent Application No. PCT/US2008/055360, mailed Jul. 24, 2008.
International Preliminary Report on Patentability, issued in International Patent Application No. PCT/US2008/055380, mailed Sep. 17, 2009.
International Search Report and Written Opinion, issued in International Patent Application No. PCT/US2008/055380, mailed Aug. 8, 2008.
International Preliminary Report on Patentability, issued in International Patent Application No. PCT/US2008/55615, mailed Sep. 17, 2009.
International Search Report and Written Opinion, issued in International Patent Application No. PCT/US2008/55615, mailed Mar. 27, 2009.
International Preliminary Report on Patentability, issued in International Patent Application No. PCT/US2008/055339, mailed Sep. 17, 2009.
International Search Report and Written Opinion, issued in International Patent Application No. PCT/US2008/055339, mailed Oct. 20, 2008.
International Preliminary Report on Patentability, issued in International Patent Application No. PCT/US2008/055385, mailed Sep. 17, 2009.
International Search Report and Written Opinion, issued in International Patent Application No. PCT/US2008/055385, mailed Aug. 21, 2008.
International Preliminary Report on Patentability, issued in International Patent Application No. PCT/US2008/055515, mailed Sep. 17, 2009.
International Search Report and Written Opinion, issued in International Patent Application No. PCT/US2008/055515, mailed Aug. 21, 2008.
International Preliminary Report on Patentability, issued in International Patent Application No. PCT/US2008/055644, mailed Sep. 17, 2009.
International Search Report and Written Opinion, issued in International Patent Application No. PCT/US2008/055644, mailed Sep. 4, 2008.
International Preliminary Report on Patentability, issued in International Patent Application No. PCT/US2008/055649, mailed Sep. 17, 2009.
International Search Report and Written Opinion, issued in International Patent Application No. PCT/US2008/055649, mailed Jul. 28, 2008.

(56) References Cited

OTHER PUBLICATIONS

International Search Report and Written Opinion, issued in International Patent Application No. PCT/US2007/081836, mailed Feb. 20, 2008.
International Preliminary Report on Patentability, issued in International Patent Application No. PCT/US2007/081836, mailed Apr. 30, 2009.
Office Action, issued in U.S. Appl. No. 12/039,650 mailed Nov. 12, 2009.
Office Action, issued in U.S. Appl. No. 12/039,662 mailed Nov. 17, 2009.
Office Action, issued in U.S. Appl. No. 12/529,011 mailed Dec. 10, 2010.
Aymami et al., "Molecular structure of nicked DNA: A substrate for DNA repair enzymes," Proc. Nat'l Acad. Sci., vol. 87, pp. 2526-2530, Apr. 1990.
Elmen et al., "Locked nucleic acid (LNA) mediated improvements in siRNA stability and functionality"; Nucleic Acids Research; Jan. 14, 2005; 439-447; vol. 33; No. 1.
Matranga et al., "Passenger-Strand Cleavage Facilitates Assembly of siRNA into Ago2-Containing RNAi Enzyme Complexes," Cell, vol. 123, pp. 1-14, Nov. 18, 2005.
Protozanova et al., "Stacked-Unstacked Equilibrium at the Nick Site of DNA," J. Mol. Biol., vol. 342, No. 3, pp. 775-785, 2004.
Rand et al., "Argonaute2 Cleaves the Anti-Guide Strand of siRNA during RISC Activation," Cell, vol. 123, pp. 621-629, Nov. 18, 2005.
Yakovchuk et al., "Base-stacking and base-pairing contributions into thermal stability of the DNA double helix," Nucleic Acids Research, vol. 24, No. 2, pp. 564-574, 2006.
Wengel, "LNA Enhances Gene Silencing and miRNA Targeting," Informa Life Sciences 8th Annual Conference, Eurotides Conference, 21 pages, Dec. 4, 2007.
Office Action, issued in Australian Patent Application No. 2007310982, mailed Apr. 12, 2012.
Office Action, issued in Canadian Patent Application No. 2,666,657, mailed Mar. 22, 2013.
Office Action, issued in Japanese Patent Application No. 2009-533539, mailed Dec. 4, 2012.
Office Action, issued in Japanese Patent Application No. 2009-533539, mailed Mar. 11, 2014.
Office Action, issued in U.S. Appl. No. 12/039,662, mailed Dec. 11, 2013.
Office Action, issued in U.S. Appl. No. 12/528,619, mailed Oct. 19, 2011.
Office Action, issued in U.S. Appl. No. 12/528,619, mailed May 29, 2013.
Office Action, issued in U.S. Appl. No. 12/529,011, mailed Jun. 10, 2011.
Office Action, issued in U.S. Appl. No. 12/529,011, mailed Nov. 13, 2012.
Office Action, issued in U.S. Appl. No. 12/039,658, mailed Jul. 29, 2014.
Office Action, issued in U.S. Appl. No. 12/039,668, mailed Dec. 1, 2011.
Office Action, issued in U.S. Appl. No. 12/039,668, mailed May 17, 2013.
Office Action, issued in U.S. Appl. No. 12/039,650, mailed Dec. 11, 2013.
Office Action, issued in U.S. Appl. No. 12/528,508, mailed Jun. 7, 2011.
Bahramian et al., "Transcriptional and Posttranscriptional Silencing of Rodent α1(I) Collagen by a Homologous Transcriptionally Self-silenced Transgene," Molecular and Cellular Biology, vol. 19, No. 1, pp. 274-283, Jan. 1999.
Beigelman et al., "Chemical modification of hammerhead ribozymes. Catalytic activity and nuclease resistance," J. Biol. Chem. 270:25702-8, Oct. 1995.
Bernstein et al., "Role for a bidentate ribonuclease in the inititation step of RNA interference," Nature, vol. 409, 363-366, Jan. 18, 2001.

Bramsen, J.B. et al., "Improved silencing properties using small internally segmented interfering RNAs," Nucleic Acids Research, vol. 35, No. 17, Jul. 28, 2007, pp. 5886-5897.
Brody et al., "Aptamers as therapeutic and diagnostic agents," Reviews in Molecular Biotechnology, vol. 74, pp. 5-13, Mar. 2000.
Burgin et al., "Chemically modified hammerhead ribozymes with improved catalytic rates," Biochemistry, vol. 35, pp. 14090-14097, Nov. 1996.
Burlina et al., "Chemical engineering of RNase resistant and catalytically active hammerhead ribozymes," Bioorganic & Medicinal Chemistry, vol. 5, No. 11, pp. 1999-2010, Nov. 1997.
De Mesmaeker et al., "Novel Backbone Replacements for Oligonucleotides," American Chemical Society, 24-39, 1994.
Dorsett et al., "siRNAs: Applications in functional genomics and potential as therapeutics," Nature Reviews Drug Discovery, vol. 3, pp. 318-29, Apr. 2004.
Du et al., "A systematic analysis of the silencing effects of an active siRNA at all single-nucleotide mismatched target sites," Nucleic Acids Research, vol. 33, pp. 1671-1677, Mar. 21, 2005.
Earnshaw et al., "Modified Oligoribonucleotides as Site-Specific Probes of RNA Structure and Function," Biopolymers (Nucleic Acid Sciences), vol. 48, pp. 39-55, 1998.
Elbashir et al., "Duplexes of 21-nucleotide RNAs mediate RNA interference in cultured mammalian cells," Nature, vol. 411, pp. 494-498, May 24, 2001.
Elbashir et al., "Functional anatomy of siRNAs for mediating efficient RNAi in *Drosophila melanogaster* embryo lysate," EMBO J., vol. 20, pp. 6877-6888, Dec. 3, 2001.
Elbashir et al., "RNA interference is mediated by 21- and 22-nucleotide RNAs," Genes & Development, vol. 15, pp. 188-200, 2001.
Fire et al., "Potent and specific genetic interference by double-stranded RNA in *Caenorhabditis elegans*," Nature, vol. 391, pp. 806-811, Feb. 19, 1998.
Fire et al., "RNA-triggered gene silencing," Trends in Genetics, vol. 15, No. 9, pp. 358-363, Sep. 1999.
Gold et al., "Diversity of oligonucleotide functions," Annu. Rev. Biochem., vol. 64, pp. 763-797, 1995.
Hagerman, K.R. et al., "Helix rigidity of DNA: the meroduplex as an experimental paradigm," Journal of Molecular Biology, vol. 260, Jul. 12, 1996, pp. 207-223.
Hamilton et al., "A species of small antisense RNA in post-transcriptional gene silencing in plants," Science, vol. 286, pp. 950-952, Oct. 1999.
Hammond et al., "An RNA-directed nuclease mediates post-transcriptional gene silencing in *Drosophila* cells," Nature, vol. 404, pp. 293-296, Mar. 16, 2000.
Herdewijn, "Heterocyclic Modifications of Oligonucleatides and Antisense Technology," Antisense Nucleic Acid Drug Development, vol. 10, pp. 297-310, 2000.
Hermann et al., "Adaptive recognition by nucleic acid aptamers," Science, vol. 287, pp. 820-825, Feb. 4, 2000.
Hunziker et al., "Nucleic Acid Analogues: Synthesis and Properties," Modern Synthetic Methods, pp. 331-417, 1995.
Hutvagner et al., "A cellular function for the RNA-interference enzyme Dicer in the maturation of the let-7 small temporal RNA," Science, vol. 293, pp. 834-838, Jul. 2001.
Jackson et al., "Expression profiling reveals off-target gene regulation by RNAi," Nature Biotechnology, vol. 21, No. 6, pp. 635-637, May 18, 2003.
Jayasena, "Aptamers: an emerging class of molecules that rival antibodies in diagnostics," Clinical Chem., vol. 45, pp. 1628-1650, Sep. 1999.
Karpeisky et al., "Highly Efficient Synthesis of 2'-O-Amino Nucleosides and Their Incorporation in Hammerhead Ribozymes," Tetrahedron Letters, vol. 39, pp. 1131-1134, 1998.
Kim et al., "Synthetic dsRNA Dicer substrates enhance RNAi potency and efficacy," Nature Biotechnology, vol. 23, No. 2, pp. 222-226, Dec. 26, 2004.
Kroschwitz, J. I., "Polynucleotides," Concise Encyclopedia of Polymer Science and Engineering, pp. 858-859, Kroschwitz, J. I., ed. John Wiley & Sons, 1990.

(56) References Cited

OTHER PUBLICATIONS

Kurreck, "Antisense technologies. Improvement through novel chemical modifications," Eur. J. Biochem., vol. 270, pp. 1628-1644, Apr. 2003.

Kusser, "Chemically modified nucleic acid aptamers for in vitro selections: evolving evolution," Molecular Biotechnology, vol. 74, pp. 27-38, Mar. 2000.

Leuschner, Philipp et al., "Cleavage of the siRNA passenger strand during RISC assembly in human cells," EMBO Reports, Nature Publishing Group, vol. 7, No. 3, Mar. 1, 2006, pp. 314-320.

Lin et al. "A Cytosine Analogue Capable of Clamp-Like Binding to a Guanine in Helical Nucleic Acids," J. Am. Chem. Soc., vol. 120, pp. 8531-8532, 1998.

Loakes et al., "Stability and structure of DNA oligonucleotides containing non-specific base analogues," J. Mol. Bio., vol. 270, pp. 426-435, Jul. 18, 1997.

Loakes, "Survey and summary: The applications of universal DNA base analogues," Nucleic Acids Res., vol. 29, pp. 2437-2447, Jun. 15, 2001.

Ma et al., "Design and synthesis of RNA miniduplexes via a synthetic linker approach," Biochemistry, vol. 32, pp. 1751-17588, Feb. 23, 1993.

Ma et al., "Design and synthesis of RNA miniduplexes via a synthetic linker approach. 2. Generation of covalently closed, double-stranded cyclic HIV-1 TAR RNA analogs with high Tat-binding affinity," Nucleic Acids Research, vol. 21, No. 11, pp. 2585-2589, 1993.

Martinez et al., "Single-stranded antisense siRNAs guide target RNA cleavage in RNAi," Cell, vol. 110, pp. 563-574, Sep. 6, 2002.

Mills, Janine B. et al., "Origin of the intrinsic rigidity of DNA," Nucleic Acids Research, vol. 32, No. 13, Jan. 1, 2004, pp. 4055-4059.

Nykanen et al., "ATP requirements and small interfering RNA structure in the RNA interference pathway," Cell, vol. 107, pp. 309-321, Nov. 2, 2001.

Perreault et al., "Mixed deoxyribo- and ribo-oligonucleotides with catalytic activity," Nature, vol. 344, pp. 565-567, Apr. 5, 1990.

Pieken et al., "Kinetic characterization of ribonuclease-resistant 2'-modified hammerhead ribozymes," Science, vol. 253, pp. 314-317, Jul. 19, 1991.

Schwarz et al., "Evidence that siRNAs function as guides, not primers, in the *Drosophila* and human RNAi pathways," Molecular Cell, vol. 10, pp. 537-548, Sep. 2002.

Sun, "Technology evaluation: SELEX, Gilead Sciences Inc.," Current Opinion in Molecular Therapeutics, vol. 2, No. 1, pp. 100-105, 2000.

Usman et al., "Exploiting the chemical synthesis of RNA," Trends in Biochem. Sci., vol. 17, pp. 334-339, Sep. 1992.

Usman et al., "Chemical modification of hammerhead ribozymes: activity and nuclease resistance," Nucleic Acids Symposium Series, No. 31, pp. 163-164, 1994.

Verma et al., "Modified oligonucleotides: synthesis and strategy for users," Annual Review of Biochemistry, vol. 67, pp. 99-134, 1998.

Wianny et al., "Specific interference with gene function by double-stranded RNA in early mouse development," Nature Cell Biology, vol. 2, pp. 70-75, Feb. 2000.

Office Action, issued in EP Patent Application No. 07844409.8, mailed Jan. 14, 2010.

Office Action, issued in EP Patent Application No. 08731244.3, mailed Feb. 3, 2010.

* cited by examiner

SEQUENCE LISTING

```
<160> NUMBER OF SEQ ID NOS: 62

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 1
cuacacaaau cagcgauuut t                                                    21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 2
aaaucgcuga uuuguguagt t                                                    21

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 3
cuacacaaau cagcgauuuc caugt                                                25

<210> SEQ ID NO 4
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 4
acauggaaau cgcugauuug uguaguc                                              27

<210> SEQ ID NO 5
<211> LENGTH: 13
<212> TYPE: RNA
<213> ORGANISM: Artificial Sequence
<220> FEATURE:
<223> OTHER INFORMATION: Synthetic oligonucleotide

<400> SEQUENCE: 5
cuacacaaau cag                                                             13

<210> SEQ ID NO 6
<211> LENGTH: 11
<212> TYPE: DNA
<213> ORGANISM: Artificial Sequence
<220> FEATURE:
<223> OTHER INFORMATION: Synthetic oligonucleotide; combined DNA/RNA
```

```
<400> SEQUENCE: 6
gauuuccaug t                                                            11

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 7
ggaucuuauu ucuucggagt t                                                 21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 8
cuccgaagaa auaagaucct t                                                 21

<210> SEQ ID NO 9
<211> LENGTH: 11
<212> TYPE: RNA
<213> ORGANISM: Artificial Sequence
<220> FEATURE:
<223> OTHER INFORMATION: Synthetic oligonucleotide

<400> SEQUENCE: 9
ggaucuuauu u                                                            11

<210> SEQ ID NO 10
<211> LENGTH: 10
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 10
cuucggagtt                                                              10

<210> SEQ ID NO 11
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 11
cauugucucc gaagaaauaa gauccuu                                           27

<210> SEQ ID NO 12
<211> LENGTH: 8
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 12 ggaucuua                                                                 8
```

<210> SEQ ID NO 13
<211> LENGTH: 17
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 13
uuucuucgga gacaatg                                              17

<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 14
uucuucggag acaatg                                               16

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 15
ucuucggaga caatg                                                15

<210> SEQ ID NO 16
<211> LENGTH: 14
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 16
cuucggagac aatg                                                 14

<210> SEQ ID NO 17
<211> LENGTH: 13
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 17
uucggagaca atg                                                  13

<210> SEQ ID NO 18
<211> LENGTH: 12
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 18
ucggagacaa tg                                                   12

<210> SEQ ID NO 19
<211> LENGTH: 11
<212> TYPE: DNA
<213> ORGANISM: Artificial Sequence
<220> FEATURE:

<223> OTHER INFORMATION: Synthetic oligonucleotide

<400> SEQUENCE: 19
cggagacaat g                                                                11

<210> SEQ ID NO 20
<211> LENGTH: 9
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 20 ggaucuuau                                                                    9

<210> SEQ ID NO 21
<211> LENGTH: 10
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 21
ggaucuuauu                                                                  10

<210> SEQ ID NO 22
<211> LENGTH: 11
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 22
ggaucuuauu u                                                                11

<210> SEQ ID NO 23
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 23
ggaucuuauu uc                                                               12

<210> SEQ ID NO 24
<211> LENGTH: 8
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base

```
<222> LOCATION: (3)..(3)
<223> OTHER INFORMATION: LNA-A

<400> SEQUENCE: 24 cuacacaa                                                                    8

<210> SEQ ID NO 25
<211> LENGTH: 13
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (8)..(8)
<223> OTHER INFORMATION: LNA-A

<400> SEQUENCE: 25
aucagcgauu utt                                                             13

<210> SEQ ID NO 26
<211> LENGTH: 12
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (7)..(7)
<223> OTHER INFORMATION: LNA-A

<400> SEQUENCE: 26
ucagcgauuu tt                                                              12

<210> SEQ ID NO 27
<211> LENGTH: 11
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (6)..(6)
<223> OTHER INFORMATION: LNA-A

<400> SEQUENCE: 27
cagcgauuut t                                                               11

<210> SEQ ID NO 28
<211> LENGTH: 10
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (5)..(5)
<223> OTHER INFORMATION: LNA-A

<400> SEQUENCE: 28
agcgauuutt                                                                 10

<210> SEQ ID NO 29
<211> LENGTH: 9
<212> TYPE: DNA
<213> ORGANISM: Artificial Sequence
<220> FEATURE:
<223> OTHER INFORMATION: Synthetic oligonucleotide; combined DNA/RNA
<220> FEATURE:
```

<221> NAME/KEY: modified_base
<222> LOCATION: (4)..(4)
<223> OTHER INFORMATION: LNA-A

<400> SEQUENCE: 29 gcgauuutt                                                                    9

<210> SEQ ID NO 30
<211> LENGTH: 8
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (3)..(3)
<223> OTHER INFORMATION: LNA-A

<400> SEQUENCE: 30 cgauuutt                                                                     8

<210> SEQ ID NO 31
<211> LENGTH: 7
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (2)..(2)
<223> OTHER INFORMATION: LNA-A

<400> SEQUENCE: 31 gauuutt                                                                      7

<210> SEQ ID NO 32
<211> LENGTH: 9
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: LNA-A

<400> SEQUENCE: 32 cuacacaaa                                                                    9

<210> SEQ ID NO 33
<211> LENGTH: 10
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: LNA-A

<400> SEQUENCE: 33
cuacacaaau                                                                  10

<210> SEQ ID NO 34
<211> LENGTH: 11
<212> TYPE: RNA
<213> ORGANISM: Artificial Sequence
<220> FEATURE:
<223> OTHER INFORMATION: Synthetic oligonucleotide

```
<220> FEATURE:
<221> NAME/KEY: modified_base
<222> LOCATION: (3)..(3)
<223> OTHER INFORMATION: LNA-A

<400> SEQUENCE: 34
cuacacaaau c                                                            11

<210> SEQ ID NO 35
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<220> FEATURE:
<221> NAME/KEY: modified_base
<222> LOCATION: (3)..(3)
<223> OTHER INFORMATION: LNA-A

<400> SEQUENCE: 35
cuacacaaau ca                                                           12

<210> SEQ ID NO 36
<211> LENGTH: 13
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: LNA-A

<400> SEQUENCE: 36
cuacacaaau cag                                                          13

<210> SEQ ID NO 37
<211> LENGTH: 14
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(3)
<223> OTHER INFORMATION: LNA-A

<400> SEQUENCE: 37
cuacacaaau cagc                                                         14

<210> SEQ ID NO 38
<211> LENGTH: 13
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 38
ggaucuuauu ucu                                                          13

<210> SEQ ID NO 39
<211> LENGTH: 14
```

```
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 39
ggaucuuauu ucuu                                                        14

<210> SEQ ID NO 40
<211> LENGTH: 8
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (8)..(8)
<223> OTHER INFORMATION: LNA-A

<400> SEQUENCE: 40 ggaucuua                                                                8

<210> SEQ ID NO 41
<211> LENGTH: 9
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (9)..(9)
<223> OTHER INFORMATION: LNA-U

<400> SEQUENCE: 41 ggaucuuau                                                               9

<210> SEQ ID NO 42
<211> LENGTH: 10
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (10)..(10)
<223> OTHER INFORMATION: LNA-U

<400> SEQUENCE: 42
ggaucuuauu                                                             10

<210> SEQ ID NO 43
<211> LENGTH: 11
<212> TYPE: RNA
<213> ORGANISM: Artificial Sequence
<220> FEATURE:
```

```
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (11)..(11)
<223> OTHER INFORMATION: LNA-U

<400> SEQUENCE: 43
ggaucuuauu u                                                              11

<210> SEQ ID NO 44
<211> LENGTH: 12
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (12)..(12)
<223> OTHER INFORMATION: LNA-C

<400> SEQUENCE: 44
ggaucuuauu uc                                                             12

<210> SEQ ID NO 45
<211> LENGTH: 13
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (13)..(13)
<223> OTHER INFORMATION: LNA-U

<400> SEQUENCE: 45
ggaucuuauu ucu                                                            13

<210> SEQ ID NO 46
<211> LENGTH: 14
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (14)..(14)
<223> OTHER INFORMATION: LNA-U

<400> SEQUENCE: 46
ggaucuuauu ucuu                                                           14

<210> SEQ ID NO 47
<211> LENGTH: 13
<212> TYPE: DNA
<213> ORGANISM: Artificial Sequence
```

-continued

```
<220> FEATURE:
<223> OTHER INFORMATION: Synthetic oligonucleotide; combined DNA/RNA
<220> FEATURE:
<221> NAME/KEY: modified_base
<222> LOCATION: (8)..(8)
<223> OTHER INFORMATION: LNA-G

<400> SEQUENCE: 47
uuucuucgga gtt                                                          13

<210> SEQ ID NO 48
<211> LENGTH: 12
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (7)..(7)
<223> OTHER INFORMATION: LNA-G

<400> SEQUENCE: 48
uucuucggag tt                                                           12

<210> SEQ ID NO 49
<211> LENGTH: 11
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (6)..(6)
<223> OTHER INFORMATION: LNA-G

<400> SEQUENCE: 49
ucuucggagt t                                                            11

<210> SEQ ID NO 50
<211> LENGTH: 10
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (5)..(5)
<223> OTHER INFORMATION: LNA-G

<400> SEQUENCE: 50
cuucggagtt                                                              10

<210> SEQ ID NO 51
<211> LENGTH: 9
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (4)..(4)
<223> OTHER INFORMATION: LNA-G

<400> SEQUENCE: 51 uucggagtt                                                                9

<210> SEQ ID NO 52
<211> LENGTH: 8
<212> TYPE: DNA
```

```
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (3)..(3)
<223> OTHER INFORMATION: LNA-G

<400> SEQUENCE: 52 ucggagtt                                                                    8

<210> SEQ ID NO 53
<211> LENGTH: 7
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: LNA-G

<400> SEQUENCE: 53 cggagtt                                                                     7

<210> SEQ ID NO 54
<211> LENGTH: 13
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (1)..(1)
<223> OTHER INFORMATION: LNA-U
<220> FEATURE:
<221> NAME/KEY: modified_base
<222> LOCATION: (8)..(8)
<223> OTHER INFORMATION: LNA-G

<400> SEQUENCE: 54
uuucuucgga gtt                                                             13

<210> SEQ ID NO 55
<211> LENGTH: 12
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (1)..(1)
<223> OTHER INFORMATION: LNA-U
<220> FEATURE:
<221> NAME/KEY: modified_base
<222> LOCATION: (7)..(7)
<223> OTHER INFORMATION: LNA-G

<400> SEQUENCE: 55
uucuucggag tt                                                              12

<210> SEQ ID NO 56
<211> LENGTH: 11
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (1)..(1)
<223> OTHER INFORMATION: LNA-U
```

```
<220> FEATURE:
<221> NAME/KEY: modified_base
<222> LOCATION: (6)..(6)
<223> OTHER INFORMATION: LNA-G

<400> SEQUENCE: 56
ucuucggagt t                                                              11

<210> SEQ ID NO 57
<211> LENGTH: 10
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (1)..(1)
<223> OTHER INFORMATION: LNA-C
<220> FEATURE:
<221> NAME/KEY: modified_base
<222> LOCATION: (5)..(5)
<223> OTHER INFORMATION: LNA-G

<400> SEQUENCE: 57
cuucggagtt                                                                10

<210> SEQ ID NO 58
<211> LENGTH: 9
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (1)..(1)
<223> OTHER INFORMATION: LNA-U
<220> FEATURE:
<221> NAME/KEY: modified_base
<222> LOCATION: (4)..(4)
<223> OTHER INFORMATION: LNA-G

<400> SEQUENCE: 58 uucggagtt                                                                 9

<210> SEQ ID NO 59
<211> LENGTH: 8
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (1)..(1)
<223> OTHER INFORMATION: LNA-U
<220> FEATURE:
<221> NAME/KEY: modified_base
<222> LOCATION: (3)..(3)
<223> OTHER INFORMATION: LNA-G

<400> SEQUENCE: 59 ucggagtt                                                                  8

<210> SEQ ID NO 60
<211> LENGTH: 7
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
```

```
<223> OTHER INFORMATION: LNA-C
<220> FEATURE:
<221> NAME/KEY: modified_base
<222> LOCATION: (2)..(2)
<223> OTHER INFORMATION: LNA-G

<400> SEQUENCE: 60 cggagtt                                                                    7

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide; combined DNA/RNA
<220> FEATURE:
<221> NAME/KEY: modified_base
<222> LOCATION: (2)..(2)
<223> OTHER INFORMATION: LNA-G
<220> FEATURE:
<221> NAME/KEY: modified_base
<222> LOCATION: (16)..(16)
<223> OTHER INFORMATION: LNA-G

<400> SEQUENCE: 61
ggaucuuauu ucuucggagt t                                                   21

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide; combined DNA/RNA

<400> SEQUENCE: 62
ggaucuuauu ucuucggaga caatg                                               25
```

NICKED OR GAPPED NUCLEIC ACID MOLECULES AND USES THEREOF

CROSS-REFERENCE TO RELATED APPLICATIONS

This application claims the benefit of U.S. provisional application Ser. Nos. 60/862,027 filed Oct. 18, 2006; 60/910,393 filed Apr. 5, 2007; 60/955,317 filed Aug. 10, 2007; and 60/969,136 filed Aug. 30, 2007.

SEQUENCE LISTING

The present application includes a Sequence Listing in electronic format as a txt file titled "12445868_Substitute-_Sequence_Listing_Sep09," which was created on Sep. 9, 2009 and which has a size of 17 kilobytes (KB). The contents of txt file "12445868_Substitute_Sequence_Listing_Sep09" are incorporated by reference herein.

TECHNICAL FIELD

The present disclosure provides double-stranded nucleic acid molecules capable of gene silencing and, more specifically, a nicked or gapped double-stranded RNA (dsRNA) comprising at least three strands that decreases expression of a target gene by, for example, RNA interference and uses of such dsRNA to treat or prevent disorders associated with expression of the target gene or genes affected by the target gene.

BACKGROUND

RNA interference (RNAi) refers to the cellular process of sequence specific, post-transcriptional gene silencing in animals mediated by small inhibitory nucleic acid molecules, such as a double-stranded RNA (dsRNA) that is homologous to a portion of a targeted messenger RNA (Fire et al., *Nature* 391:806, 1998; Hamilton et al., *Science* 286:950-951, 1999). RNAi has been observed in a variety of organisms, including mammalians (Fire et al., *Nature* 391:806, 1998; Bahramian and Zarbl, *Mol. Cell. Biol.* 19:274-283, 1999; Wianny and Goetz, *Nature Cell Biol.* 2:70, 1999). RNAi can be induced by introducing an exogenous synthetic 21-nucleotide RNA duplex into cultured mammalian cells (Elbashir et al., *Nature* 411:494, 2001a).

The mechanism by which dsRNA mediates targeted gene-silencing can be described as involving two steps. The first step involves degradation of long dsRNAs by a ribonuclease III-like enzyme, referred to as Dicer, into short interfering RNAs (siRNAs) having from 21 to 23 nucleotides with double-stranded regions of about 19 base pairs (Berstein et al., *Nature* 409:363, 2001; Elbashir et al., *Genes Dev.* 15:188, 2001b; and Kim et al., *Nature Biotech.* 23(2):222, 2005). The second step of RNAi gene-silencing involves activation of a multi-component nuclease having one strand (guide or antisense strand) from the siRNA and an Argonaute protein to form an RNA-induced silencing complex ("RISC") (Elbashir et al., *Genes Dev.* 15:188, 2001). Argonaute initially associates with a double-stranded siRNA and then endonucleolytically cleaves the non-incorporated strand (passenger or sense strand) to facilitate its release due to resulting thermodynamic instability of the cleaved duplex (Leuschner et al., *EMBO* 7:314, 2006). The guide strand in the activated RISC binds to a complementary target mRNA and cleaves the mRNA to promote gene silencing. Cleavage of the target RNA occurs in the middle of the target region that is complementary to the guide strand (Elbashir et al., 2001b).

Target specific gene silencing can be achieved by exogenously adding siRNA, but non-specific silencing of non-targeted genes (referred to as off-target effects) can be a challenge (see, e.g., Jackson et al., *Nat. Biotechnol.* 21:635, 2003; Du et al., *Nucleic Acids Res.* 33:1671, 2005. Hence, there remains a need in the art for alternative dsRNA molecules and methods to mediate gene silencing. The present disclosure meets such needs, and further provides other related advantages.

BRIEF SUMMARY

The present disclosure provides dsRNA molecules comprising at least three strands, designated herein as A, S1 and S2 (A:S1S2), wherein S1 and S2 are complementary to, and form base pairs (bp) with, non-overlapping regions of A. Thus, for siRNA molecules described herein; the double-stranded region formed by the annealing of S1 and A is distinct from the double-stranded region formed by the annealing of S2 and A. An A:S1 duplex may be separated from an A:S2 duplex by a "gap" resulting from at least one unpaired nucleotide in the A strand that is positioned between the A:S1 duplex and the A:S2 duplex and that is distinct from any one or more unpaired nucleotide at the 3' end of either or both of the A, S1, and/or S2 strand. Alternatively, an A:S1 duplex may be separated from an A:S2 duplex by a "nick" such that there are no unpaired nucleotides in the A strand that are positioned between the A:S1 duplex and the A:S2 duplex such that the only unpaired nucleotide, if any, is at the 3' end of either or both of the A, S1, and/or S2 strand.

In one aspect, the instant disclosure provides a meroduplex RNA (mdRNA) molecule, comprising a first strand that is complementary to a target RNA, and a second strand and a third strand that are each complementary to non-overlapping regions of the first strand, wherein the second strand and third strands can anneal with the first strand to form at least two double-stranded regions separated by a gap of up to 10 nucleotides, and wherein (a) at least one double-stranded region is from about 5 base pairs up to 13 base pairs, or (b) the double-stranded regions combined total about 15 base pairs to about 40 base pairs and the mdRNA molecule comprises blunt ends. In certain embodiments, the first strand is about 15 to about 40 nucleotides in length, and the second and third strands are each, individually, about 5 to about 20 nucleotides, wherein the combined length of the second and third strands is about 15 nucleotides to about 40 nucleotides. In other embodiments, the mdRNA is a RISC activator (e.g., the first strand has about 15 nucleotides to about 25 nucleotides) or a Dicer substrate (e.g., the first strand has about 26 nucleotides to about 40 nucleotides). In some embodiments, the gap comprises at least one to ten unpaired nucleotides in the first strand positioned between the double-stranded regions formed by the second and third strands when annealed to the first strand, or the gap comprises a nick. In certain embodiments, the nick or gap is located 10 nucleotides from the 5'-end of the first (antisense) strand or at the Argonaute cleavage site. In another embodiment, the meroduplex nick or gap is positioned such that the thermal stability is maximized for the first and second strand duplex and for the first and third strand duplex as compared to the thermal stability of such meroduplexes having a nick or gap in a different position.

In another aspect, the instant disclosure provides an mdRNA molecule having a first strand that is complementary to target RNA, and a second strand and a third strand that is each complementary to non-overlapping regions of the first strand, wherein the second strand and third strands can anneal with the first strand to form at least two double-stranded regions separated by a gap of up to 10 nucleotides, and wherein (a) at least one double-stranded region is from about 5 base pairs up to 13 base pairs, or (b) the double-stranded regions combined total about 15 base pairs to about 40 base pairs and the mdRNA molecule comprises blunt ends; and wherein at least one pyrimidine of the mdRNA comprises a pyrimidine nucleoside according to Formula I or II:

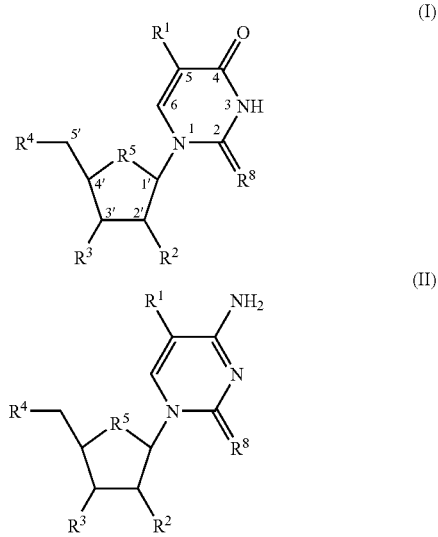

wherein $R^1$ and $R^2$ are each independently a —H, —OH, —OCH$_3$, —OCH$_2$OCH$_2$CH$_3$, —OCH$_2$CH$_2$OCH$_3$, halogen, substituted or unsubstituted $C_1$-$C_{10}$ alkyl, alkoxy, alkoxyalkyl, hydroxyalkyl, carboxyalkyl, alkylsulfonylamino, aminoalkyl, dialkylamino, alkylaminoalkyl, dialkylaminoalkyl, haloalkyl, trifluoromethyl, cycloalkyl, (cycloalkyl)alkyl, substituted or unsubstituted $C_2$-$C_{10}$ alkenyl, substituted or unsubstituted —O-allyl, —O—CH$_2$CH=CH$_2$, —O—CH=CHCH$_3$, substituted or unsubstituted $C_2$-$C_{10}$ alkynyl, carbamoyl, carbamyl, carboxy, carbonylamino, substituted or unsubstituted aryl, substituted or unsubstituted aralkyl, —NH$_2$, —NO$_2$, —C≡N, or heterocyclo group; $R^3$ and $R^4$ are each independently a hydroxyl, a protected hydroxyl, a phosphate, or an internucleoside linking group; and $R^5$ and $R^8$ are independently O or S. In certain embodiments, at least one nucleoside is according to Formula I and in which $R^1$ is methyl and $R^2$ is —OH. In certain related embodiments, at least one uridine of the dsRNA molecule is replaced with a nucleoside according to Formula I in which $R^1$ is methyl and $R^2$ is —OH, or $R^1$ is methyl, $R^2$ is —OH, and $R^8$ is S. In some embodiments, the at least one $R^1$ is a $C_1$-$C_5$ alkyl, such as methyl. In some embodiments, at least one $R^2$ is selected from 2'-O—($C_1$-$C_5$) alkyl, 2'-O-methyl, 2'-OCH$_2$OCH$_2$CH$_3$, 2'-OCH$_2$CH$_2$OCH$_3$, 2'-O-allyl, or fluoro. In some embodiments, at least one pyrimidine nucleoside of the mdRNA molecule is a locked nucleic acid (LNA) in the form of a bicyclic sugar, wherein $R^2$ is oxygen, and the 2'-O and 4'-C form an oxymethylene bridge on the same ribose ring (e.g., a 5-methyluridine LNA) or is a G clamp. In other embodiments, one or more of the nucleosides are according to Formula I in which $R^1$ is methyl and $R^2$ is a 2'-O—($C_1$-$C_5$) alkyl, such as 2'-O-methyl. In some embodiments, the gap comprises at least one unpaired nucleotide in the first strand positioned between the double-stranded regions formed by the second and third strands when annealed to the first strand, or the gap comprises a nick. In certain embodiments, the nick or gap is located 10 nucleotides from the 5'-end of the first strand or at the Argonaute cleavage site. In another embodiment, the meroduplex nick or gap is positioned such that the thermal stability is maximized for the first and second strand duplex and for the first and third strand duplex as compared to the thermal stability of such meroduplexes having a nick or gap in a different position.

Compositions and methods disclosed herein are useful for reducing expression of a target gene, or one or more genes that are a part of the target gene family, in a cell or to treating or preventing diseases or disorders associated with expression of one or more target gene family members, such as hyperproliferative disorders (e.g., cancer), inflammatory conditions (e.g., arthritis), respiratory disease, pulmonary disease, cardiovascular disease, autoimmune disease, allergic disorders, neurologic disease, infectious disease (e.g., viral infection, such as influenza), renal disease, transplant rejection, or any other disease or condition that responds to modulation of a target gene or gene family.

In certain embodiments, dsRNA of the present disclosure comprise, in sum, between about 15 base-pairs and about 40 base-pairs; or between about 18 and about 35 base-pairs; or between about 20 and 30 base-pairs; or 21, 22, 23, 24, 25, 26, 27, 28, or 29 base-pairs. Within certain embodiments, the siRNA may, optionally, comprise a single-strand 3'-overhang of between 1 nucleotide and 5 nucleotides. In particular embodiments, such a single-strand 3'-overhang is 1, 2, 3, or 4 nucleotides.

In another aspect, dsRNA of the present disclosure comprise either an A sense strand or an A antisense strand wherein the length of the A strand is between about 15 nucleotides and about 50 nucleotides; or the length of the A strand is between about 18 nucleotides and about 40 nucleotides; or the length of the A strand is between about 20 nucleotides and about 32 nucleotides; or the length of the A strand is 21, 22, 23, 24, 25, 26, 27, 28, 29, 30, or 31 nucleotides.

In another aspect, siRNA of the present disclosure additionally comprise two or more S strands, designated herein, for example, as S1 and S2, wherein each S strand is complementary to a non-overlapping region of a cognate A strand and wherein a first S strand (S1) is separated from a second S strand (S2) by a nick or a one or more nucleotide gap. Depending upon whether the cognate A strand is a sense strand or an antisense strand, each S strands will be either an antisense strand or a sense strand, respectively. Each S strand (S1, S2, etc.) described herein is, independently, between about 1 nucleotide and about 25 nucleotides in length; more typically between about 4 nucleotides and about 20 nucleotides in length; still more typically between about 5 nucleotides and about 16 nucleotides in length; most typically 6, 7, 8, 9, 10, 11, 12, 13, 14, or 15 nucleotides in length.

Depending upon the precise application contemplated, a first S strand (S1) may be separated from a second S strand (S2) by a nick or by a gap. In those embodiments wherein S1 and S2 are separated by a gap, the gap is between about one nucleotide and about 25 nucleotides; or between about one nucleotide and about 15 nucleotides; or between about one nucleotide and about 10 nucleotides; or the gap is 1, 2, 3, 4, 5, 6, 7, 8, or 9 nucleotide(s). Each S strand may, independently, terminate with a 5' hydroxyl (i.e., 5'-OH) or may terminate with a 5' phosphate group (i.e., 5'-PO$_4$).

In any of the aspects of this disclosure, there are provided mdRNA molecules having a 5-methyluridine (ribothymidine) or a 2-thioribothymidine in place of at least one uridine on the first, second, or third strand, or in place of each and every uridine on the first, second, or third strand. In further embodiments, the mdRNA may comprise any one of 5-methyluridine (ribothymidine), 2-thioribothymidine, deoxyuridine, locked nucleic acid (LNA) molecule, sugar modified with 2'-Omethyl, or G clamp, or any combination thereof. In certain embodiments, the mdRNA molecule comprises a 2'-sugar substitution, such as a 2'-O-methyl, 2'-O-methoxyethyl, 2'-O-2-methoxyethyl, 2'-O-allyl, or halogen (e.g., 2'-fluoro). In certain embodiments, the mdRNA molecule further comprises at least one terminal cap substituent on one or both ends of the first strand, second strand, or third strand, such as independently an alkyl, abasic, deoxy abasic, glyceryl, dinucleotide, acyclic nucleotide, or inverted deoxynucleotide moiety. In other embodiments, the mdRNA molecule further comprises at least one modified internucleoside linkage, such as independently a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, or boranophosphate linkage.

In any of the aspects of this disclosure, some embodiments provide an mdRNA comprising an overhang of one to four nucleotides on at least one 3'-end that is not part of the gap, such as at least one deoxyribonucleotide or two deoxyribonucleotides (e.g., thymidine). In some embodiments, at least one or two 5'-terminal ribonucleotide of the second strand within the double-stranded region comprises a 2'-sugar substitution. In related embodiments, at least one or two 5'-terminal ribonucleotide of the first strand within the double-stranded region comprises a 2'-sugar substitution. In other related embodiments, at least one or two 5'-terminal ribonucleotide of the second strand and at least one or two 5'-terminal ribonucleotide of the first strand within the double-stranded regions comprise independent 2'-sugar substitutions. In other embodiments, the mdRNA molecule comprises at least three 5-methyluridines within at least one double-stranded region. In some embodiments, the mdRNA molecule has a blunt end at one or both ends. In other embodiments, the 5'-terminal of the third strand is a hydroxyl or a phosphate.

It will be understood that methods of the present disclosure do not require a priori knowledge of the nucleotide sequence of every possible gene variant(s) targeted by the gapped or nicked dsRNA. Initially, the nucleotide sequence of the siRNA may be selected from a conserved region of the target gene.

DETAILED DESCRIPTION OF THE DISCLOSURE

Figure 1:
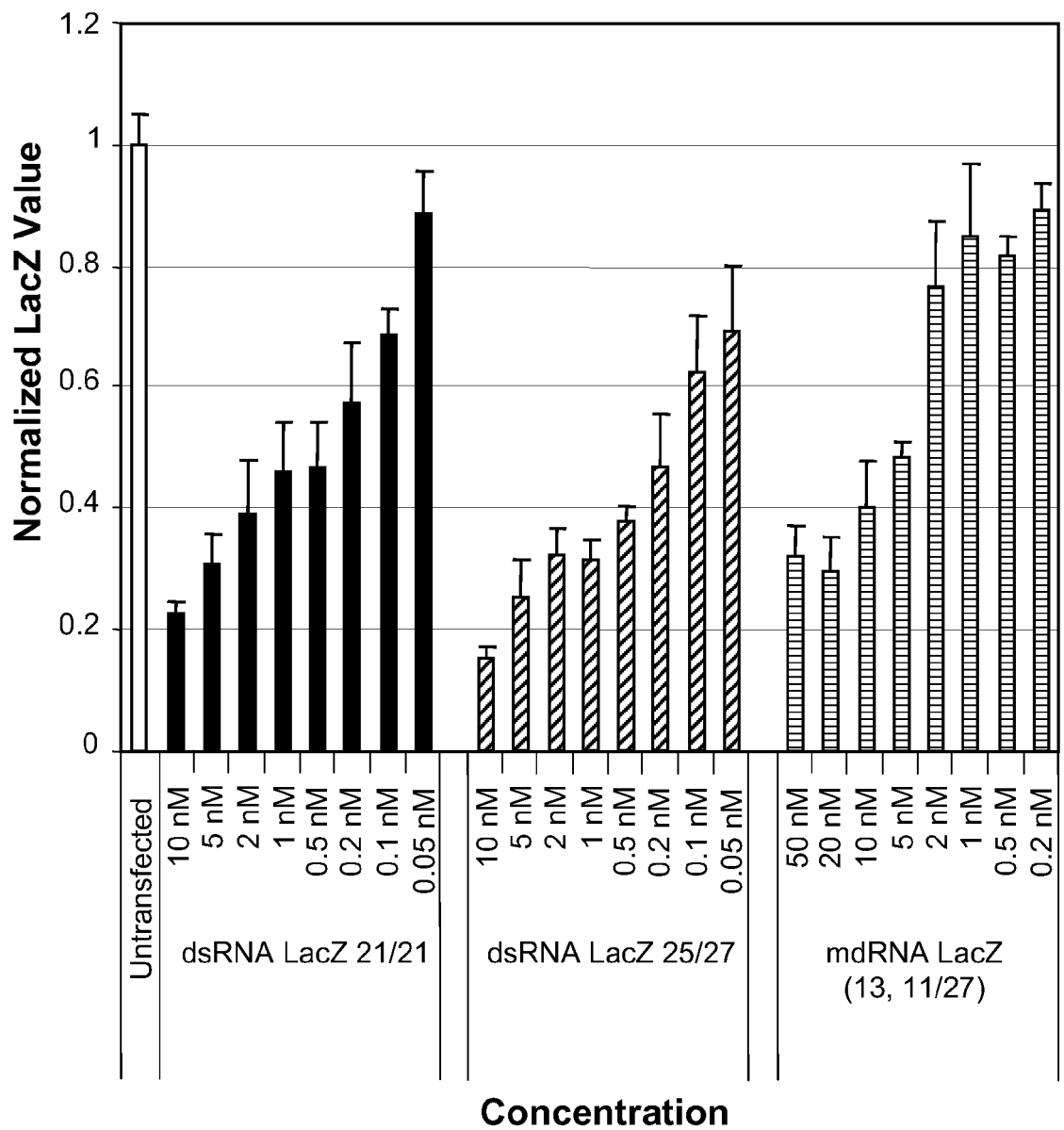
FIG. 1 shows knockdown activity for RISC activator lacZ dsRNA (21 nucleotide sense strand/21 nucleotide antisense strand; 21/21), Dicer substrate lacZ dsRNA (25 nucleotide sense strand/27 nucleotide antisense strand; 25/27), and meroduplex lacZ mdRNA (13 nucleotide sense strand and 11 nucleotide sense strand/27 nucleotide antisense strand; 13, 11/27—the sense strand is missing one nucleotide so that a single nucleotide gap is left between the 13 nucleotide and 11 nucleotide sense strands when annealed to the 27 nucleotide antisense strand. Knockdown activities were normalized to a Qneg control dsRNA and presented as a normalized value of Qneg (i.e., Qneg represents 100% or "normal" gene expression levels). A smaller value indicates a greater knockdown effect.

The instant disclosure provides gapped double-stranded RNA (dsRNA) comprising at least three strands that is a suitable substrate for Dicer or for association with RISC and, therefore, may be advantageously employed for gene silencing via, for example, the RNA interference (RNAi) pathway. That is, partially duplexed dsRNA molecules described herein (also referred to as meroduplexes or meromers having a nick or gap in at least one strand) are capable of initiating an RNAi cascade that modifies (e.g., reduces) expression of a target messenger RNA (mRNA) or a family of related target mRNAs. The gene silencing functionality of such a structure was unpredictable since the thermodynamically less stable nicked or gapped dsRNA passenger strand (as compared to an intact dsRNA) would be expected to fall apart before any gene silencing occurred (see, e.g., Leuschner et al., *EMBO* 7:314, 2006; Bramsen et al., *Nucleic Acids Res.* 35:5886, 2007).

Meroduplex ribonucleic acid (mdRNA) molecules described herein include a first (antisense) strand that is complementary to a target mRNA, along with second and third strands (together forming a gapped sense strand) that are each complementary to non-overlapping regions of the first strand, wherein the second and third strands can anneal with the first strand to form at least two double-stranded regions separated by a gap, and wherein at least one double-stranded region is from about 5 base pairs to 15 base pairs, or the combined double-stranded regions total about 15 base pairs to about 40 base pairs and the mdRNA is blunt-ended.

The gap can be from zero nucleotides (i.e., a nick in which only a phosphodiester bond between two nucleotides is broken in a polynucleotide molecule) up to about 10 nucleotides (i.e., the first strand will have at least non-terminal unpaired nucleotide). In certain embodiments, the nick or gap is located about 10 nucleotides from the 5'-end of the first (antisense) strand or at the Argonaute cleavage site. In another embodiment, the meroduplex nick or gap is positioned such that the thermal stability is maximized for the first and second strand duplex and for the first and third strand duplex as compared to the thermal stability of such meroduplexes having a nick or gap in a different position.

Also provided herein are methods of using such dsRNA to reduce expression of a target gene, or one or more genes that are a part of the target gene family, in a cell or to treat or prevent diseases or disorders associated with expression of one or more target gene family members, such as hyperproliferative disorders (e.g., cancer), inflammatory conditions (e.g., arthritis), respiratory disease, pulmonary disease, cardiovascular disease, autoimmune disease, allergic disorders, neurologic disease, infectious disease (e.g., viral infection, such as influenza), renal disease, transplant rejection, or any other disease or condition that responds to modulation of a target gene or gene family.

Prior to introducing more detail into this disclosure, it may be helpful to an appreciation thereof to provide definitions of certain terms to be used herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated. As used herein, the terms "include" and "comprise" are open-ended and are used synonymously. It should be understood that the terms "a" and "an" as used herein refer to "one or more" of the enumerated components. The use of the alternative (e.g., "or") should be understood to mean either one, both, or any combination thereof of the alternatives.

As used herein, "complementary" refers to a nucleic acid molecule that can form hydrogen bond(s) with another nucleic acid molecule or itself by either traditional Watson-Crick base pairing or other non-traditional types of pairing (e.g., Hoogsteen or reversed Hoogsteen hydrogen bonding) between complementary nucleosides or nucleotides. In reference to the nucleic molecules of the present disclosure, the binding free energy for a nucleic acid molecule with its complementary sequence is sufficient to allow the relevant function of the nucleic acid molecule to proceed, for example, RNAi activity, and there is a sufficient degree of complementarity to avoid non-specific binding of the nucleic acid molecule (e.g., dsRNA) to non-target sequences under conditions in which specific binding is desired, i.e., under physiological conditions in the case of in vivo assays or therapeutic treatment, or under conditions in which the assays are performed in the case of in vitro assays (e.g., hybridization assays). Determination of binding free energies for nucleic acid molecules is well known in the art (see, e.g., Turner et al., *CSH Symp. Quant. Biol.* LII:123, 1987; Frier et al., *Proc. Nat. Acad. Sci. USA* 83:9373, 1986; Turner et al., *J. Am. Chem. Soc.* 109:3783, 1987). Thus, "complementary" or "specifically hybridizable" or "specifically binds" are terms that indicate a sufficient degree of complementarity or precise pairing such that stable and specific binding occurs between a nucleic acid molecule (e.g., dsRNA) and a DNA or RNA target. It is understood in the art that a nucleic acid molecule need not be 100% complementary to a target nucleic acid sequence to be specifically hybridizable or to specifically bind. That is, two or more nucleic acid molecules may be less than fully complementary and is indicated by a percentage of contiguous residues in a nucleic acid molecule that can form hydrogen bonds with a second nucleic acid molecule.

For example, a first nucleic acid molecule may have 10 nucleotides and a second nucleic acid molecule may have 10 nucleotides, then base pairing of 5, 6, 7, 8, 9, or 10 nucleotides between the first and second nucleic acid molecules, which may or may not form a contiguous double-stranded region, represents 50%, 60%, 70%, 80%, 90%, and 100% complementarity, respectively. In certain embodiments, complementary nucleic acid molecules may have wrongly paired bases—that is, bases that cannot form a traditional Watson-Crick base pair or other non-traditional types of pair (i.e., "mismatched" bases). For instance, fully complementary nucleic acid molecules may be identified as having a certain number of "mismatches," such as zero or about 1, about 2, about 3, about 4 or about 5.

"Perfectly" or "fully" complementary nucleic acid molecules means those in which a certain number of nucleotides of a first nucleic acid molecule hydrogen bond (anneal) with the same number of residues in a second nucleic acid molecule to form a contiguous double-stranded region. For example, two or more fully complementary nucleic acid molecule strands can have the same number of nucleotides (i.e., have the same length and form one double-stranded region, with or without an overhang) or have a different number of nucleotides (e.g., one strand may be shorter than but fully contained within a second strand or one strand may overhang the second strand).

As used herein, "ribonucleic acid" or "RNA" means a nucleic acid molecule comprising at least one ribonucleotide molecule. It should be understood that "ribonucleotide" refers to a nucleotide with a hydroxyl group at the 2'-position of a β-D-ribofuranose moiety. The term RNA includes double-stranded (ds) RNA, single-stranded (ss) RNA, isolated RNA (such as partially purified RNA, essentially pure RNA, synthetic RNA, recombinantly produced RNA), altered RNA (which differs from naturally occurring RNA by the addition, deletion, substitution or alteration of one or more nucleotides), or any combination thereof. For example, such altered RNA can include addition of non-nucleotide material, such as at one or both ends of an RNA molecule, internally at one or more nucleotides of the RNA, or any combination thereof. Nucleotides in RNA molecules of the instant disclosure can also comprise non-standard nucleotides, such as naturally occurring nucleotides, non-naturally occurring nucleotides, chemically-modified nucleotides, deoxynucleotides, or any combination thereof. These altered RNAs may be referred to as analogs or analogs of RNA containing standard nucleotides (i.e., standard nucleotides, as used herein, are considered to be adenine, cytidine, guanidine, thymidine, and uridine).

The term "dsRNA" as used herein, which is interchangeable with "mdRNA," refers to any nucleic acid molecule comprising at least one ribonucleotide and is capable of inhibiting or down regulating gene expression, for example, by promoting RNA interference ("RNAi") or gene silencing in a sequence-specific manner. The dsRNAs (mdRNAs) of the instant disclosure may be suitable substrates for Dicer or for association with RISC to mediate gene silencing by RNAi. One or both strands of the dsRNA can further comprise a terminal phosphate group, such as a 5'-phosphate or 5',3'-diphosphate. As used herein, dsRNA molecules, in addition to at least one ribonucleotide, can further include substitutions, chemically-modified nucleotides, and non-nucleotides. In certain embodiments, dsRNA molecules comprise ribonucleotides up to about 100% of the nucleotide positions.

In addition, as used herein, the term dsRNA is meant to be equivalent to other terms used to describe nucleic acid molecules that are capable of mediating sequence specific RNAi, for example, meroduplex RNA (mdRNA), nicked dsRNA (ndsRNA), gapped dsRNA (gdsRNA), short interfering nucleic acid (siNA), siRNA, micro-RNA (miRNA), short hairpin RNA (shRNA), short interfering oligonucleotide, short interfering substituted oligonucleotide, short interfering modified oligonucleotide, chemically-modified dsRNA, post-transcriptional gene silencing RNA (ptgsRNA), or the like. The term "large double-stranded (ds) RNA" refers to any double-stranded RNA longer than about 40 base pairs (bp) to about 100 bp or more, particularly up to about 300 bp to about 500 bp. The sequence of a large dsRNA may represent a segment of an mRNA or an entire mRNA. A double-stranded structure may be formed by self-complementary nucleic acid molecule or by annealing of two or more distinct complementary nucleic acid molecule strands.

In one aspect, a dsRNA comprises two separate oligonucleotides, comprising a first strand (antisense) and a second strand (sense), wherein the antisense and sense strands are self-complementary (i.e., each strand comprises a nucleotide sequence that is complementary to a nucleotide sequence in the other strand and the two separate strands form a duplex or double-stranded structure, for example, wherein the double-stranded region is about 15 to about 24 or 25 base pairs or about 25 or 26 to about 40 base pairs); the antisense strand comprises a nucleotide sequence that is complementary to a nucleotide sequence in a target nucleic acid molecule or a portion thereof; and the sense strand comprises a nucleotide sequence corresponding (i.e., homologous) to the target nucleic acid sequence or a portion thereof (e.g., a sense strand of about 15 to about 25 nucleotides or about 26 to about 40 nucleotides corresponds to the target nucleic acid or a portion thereof).

In another aspect, the dsRNA is assembled from a single oligonucleotide in which the self-complementary sense and antisense strands of the dsRNA are linked by together by a nucleic acid based-linker or a non-nucleic acid-based linker. In certain embodiments, the first (antisense) and second (sense) strands of the dsRNA molecule are covalently linked by a nucleotide or non-nucleotide linker as described herein and known in the art. In other embodiments, a first dsRNA molecule is covalently linked to at least one second dsRNA molecule by a nucleotide or non-nucleotide linker known in the art, wherein the first dsRNA molecule can be linked to a plurality of other dsRNA molecules that can be the same or different, or any combination thereof. In another embodiment, the linked dsRNA may include a third strand that forms a meroduplex with the linked dsRNA.

In still another aspect, dsRNA molecules described herein form a meroduplex RNA (mdRNA) having three or more strands such as, for example, an 'A' (first or antisense) strand, 'S1' (second) strand, and 'S2' (third) strand in which the 'S1' and 'S2' strands are complementary to and form base pairs (bp) with non-overlapping regions of the 'A' strand (e.g., an mdRNA can have the form of A:S1S2). The S1, S2, or more strands together essentially comprise a sense strand to the 'A' strand. The double-stranded region formed by the annealing of the 'S1' and 'A' strands is distinct from and non-overlapping with the double-stranded region formed by the annealing of the 'S2' and 'A' strands. An mdRNA molecule is a "gapped" molecule, meaning a "gap" ranging from 0 nucleotides up to about 10 nucleotides. In one embodiment, the A:S1 duplex is separated from the A:S2 duplex by a gap resulting from at least one unpaired nucleotide (up to about 10 unpaired nucleotides) in the 'A' strand that is positioned between the A:S1 duplex and the A:S2 duplex and that is distinct from any one or more unpaired nucleotide at the 3'-end of one or more of the 'A', 'S1', or 'S2' strands. In another embodiment, the A:S1 duplex is separated from the A:S2 duplex by a gap of zero nucleotides (i.e., a nick in which only a phosphodiester bond between two nucleotides is broken or missing in the polynucleotide molecule) between the A:S1 duplex and the A:S2 duplex—which can also be referred to as nicked dsRNA (ndsRNA). For example, A:S1S2 may be comprised of a dsRNA having at least two double-stranded regions that combined total about 14 base pairs to about 40 base pairs and the double-stranded regions are separated by a gap of about 0 to about 10 nucleotides, optionally having blunt ends, or A:S1S2 may comprise a dsRNA having at least two double-stranded regions separated by a gap of up to 10 nucleotides wherein at least one of the double-stranded regions comprises between about 5 base pairs and 13 base pairs.

A dsRNA or large dsRNA may include a substitution or modification in which the substitution or modification may be in a phosphate backbone bond, a sugar, a base, or a nucleoside. Such nucleoside substitutions can include natural non-standard nucleosides (e.g., 5-methyluridine or 5-methylcytidine or a 2-thioribothymidine), and such backbone, sugar, or nucleoside modifications can include an alkyl or heteroatom substitution or addition, such as a methyl, alkoxyalkyl, halogen, nitrogen or sulfur, or other modifications known in the art.

In certain embodiments, the dsRNA or mdRNA will be isolated. As used herein, the term "isolated" means that the molecule referred to is removed from its original environment, such as being separated from some or all of the co-existing materials in a natural environment (e.g., a natural environment may be a cell).

As used herein, the term "RNAi" is meant to be equivalent to other terms used to describe sequence specific RNA interference, such as post transcriptional gene silencing, translational inhibition, or epigenetics. For example, dsRNA molecules of this disclosure can be used to epigenetically silence genes at the post-transcriptional level or the pre-transcriptional level or any combination thereof.

As used herein, "target nucleic acid" refers to any nucleic acid sequence whose expression or activity is to be altered. The target nucleic acid can be DNA, RNA, or analogs thereof, and includes single, double, and multi-stranded forms. By "target site" or "target sequence" is meant a sequence within a target nucleic acid (e.g., mRNA) that is "targeted" for cleavage by RNAi and mediated by a dsRNA construct of this disclosure containing a sequence within the antisense strand that is complementary to the target site or sequence.

As used herein, "off-target effect" or "off-target profile" refers to the observed altered expression pattern of one or more genes in a cell or other biological sample not targeted, directly or indirectly, for gene silencing by an mdRNA or dsRNA. For example, an off-target effect can be quantified by using a DNA microarray to determine how many non-target genes have an expression level altered by about 2-fold or more in the presence of a candidate mdRNA or dsRNA, or analog thereof specific for a target sequence, such as one or more target mRNA. A "minimal off-target effect" means that an mdRNA or dsRNA affects expression by about 2-fold or more of about 25% to about 1% of the non-target genes examined or it means that the off-target effect of substituted or modified mdRNA or dsRNA (e.g., having at least one uridine substituted with a 5-methyluridine or 2-thioribothymidine and optionally having at least one nucleotide modified at the 2'-position), is reduced by at least about 1% to about 80% or more as compared to the effect on non-target genes of an unsubstituted or unmodified mdRNA or dsRNA.

By "sense region" or "sense strand" is meant one or more nucleotide sequences of a dsRNA molecule having complementarity to one or more antisense regions of the dsRNA molecule. In addition, the sense region of a dsRNA molecule comprises a nucleic acid sequence having homology or identity to a target sequence. By "antisense region" or "antisense strand" is meant a nucleotide sequence of a dsRNA molecule having complementarity to a target nucleic acid sequence. In addition, the antisense region of a dsRNA molecule can comprise a nucleic acid sequence regions having complementarity to one or more sense strands of a dsRNA molecule.

"Analog" as used herein refers to a compound that is structurally similar to a parent compound (e.g., a nucleic acid molecule), but differs slightly in composition (e.g., one atom or functional group is different, added, or removed). The analog may or may not have different chemical or physical properties than the original compound and may or may not have improved biological or chemical activity. For example, the analog may be more hydrophilic or it may have altered activity as compared to a parent compound. The analog may mimic the chemical or biological activity of the parent compound (i.e., it may have similar or identical activity), or, in some cases, may have increased or decreased activity. The analog may be a naturally or non-naturally occurring (e.g., chemically-modified or recombinant) variant of the original compound. An example of an RNA analog is an RNA molecule having a non-standard nucleotide, such as 5-methyuridine or 5-methylcytidine or 2-thioribothymidine, which may impart certain desirable properties (e.g., improve stability, bioavailability, minimize off-target effects or interferon response).

The term "pyrimidine" as used herein refers to conventional pyrimidine bases, including standard pyrimidine bases uracil and cytosine. In addition, the term pyrimidine is contemplated to embrace natural non-standard pyrimidine bases or acids, such as 5-methyluracil, 2-thio-5-methyluracil, 4-thiouracil, pseudouracil, dihydrouracil, orotate, 5-methylcytosine, or the like, as well as a chemically-modified bases or "universal bases," which can be used to substitute for a standard pyrimidine within nucleic acid molecules of this disclosure.

The term "purine" as used herein refers to conventional purine bases, including standard purine bases adenine and guanine. In addition, the term purine is contemplated to embrace natural non-standard purine bases or acids, such as N2-methylguanine, inosine, or the like, as well as a chemically-modified bases or "universal bases," which can be used to substitute for a standard purine within nucleic acid molecules of this disclosure.

As used herein, the term "universal base" refers to nucleotide base analogs that form base pairs with each of the standard DNA/RNA bases with little discrimination between them, and is recognized by intracellular enzymes (see, e.g., Loakes et al., *J. Mol. Bio.* 270:426-435, 1997). Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, e.g., Loakes, *Nucleic Acids Res.* 29:2437-2447, 2001).

The term "gene" as used herein, especially in the context of "target gene" or "gene target" for RNAi, means a nucleic acid molecule that encodes an RNA or a transcription product of such gene, including a messenger RNA (mRNA, also referred to as structural genes that encode for a polypeptide), an mRNA splice variant of such gene, a functional RNA (fRNA), or non-coding RNA (ncRNA), such as small temporal RNA (stRNA), microRNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for dsRNA mediated RNAi to alter the activity of fRNA or ncRNA involved in functional or regulatory cellular processes. A target gene can be a gene derived from a cell, such as an endogenous gene, a transgene, or exogenous gene, including genes from a pathogen (e.g., a viral gene) that is present in a cell after infection thereof. A cell containing a target gene can be derived from or contained in any organism, for example, a plant, animal, protozoan, virus, bacterium, or fungus.

Furthermore, one or more dsRNA may be used to knockdown expression of a target mRNA or a related mRNA splice variant. In this regard, it is noted that a target gene may be transcribed into two or more mRNA splice variants. In certain embodiments, knockdown of one target mRNA splice variant without affecting one or more other target mRNA splice variants may be desired, or vice versa. Alternatively, knockdown of all transcription products of one or more target family genes is contemplated herein.

As used herein, "gene silencing" refers to a partial or complete loss-of-function through targeted inhibition of gene expression in a cell, which may also be referred to as RNAi "knockdown," "inhibition," "down-regulation," or "reduction" of expression of a target gene. Depending on the circumstances and the biological problem to be addressed, it may be preferable to partially reduce gene expression. Alternatively, it might be desirable to reduce gene expression as much as possible. The extent of silencing may be determined by methods described herein and known in the art, some of which are summarized in PCT Publication No. WO 99/32619. Depending on the assay, quantification of gene expression permits detection of various amounts of inhibition that may be desired in certain embodiments of this disclosure, including prophylactic and therapeutic methods, which will be capable of knocking down target gene expression, in terms of mRNA level or protein level or activity, for example, by equal to or greater than 10%, 30%, 50%, 75% 90%, 95% or 99% of baseline (i.e., normal) or other control levels, including elevated expression levels as may be associated with particular disease states or other conditions targeted for therapy.

By "subject" is meant an organism, which is a donor or recipient of explanted cells or the cells themselves. "Subject" also refers to an organism to which the nucleic acid molecules of this disclosure can be administered. In one embodiment, a subject is a mammal or mammalian cell. In another embodiment, a subject is a human or human cell.

As used herein, the term "therapeutically effective amount" means an amount of dsRNA that is sufficient to result in a decrease in severity of disease symptoms, an increase in frequency or duration of disease symptom-free periods, or a prevention of impairment or disability due to the disease, in the subject (e.g., mammal or human) to which it is administered. For example, a therapeutically effective amount of dsRNA directed against a target mRNA, which effectively down-regulates the target-encoding mRNA and thereby reduces or prevents one or more target-associated disorders, such as an infection, inflammation, metabolic disorders, autoimmune condition(s), cancer, or the like. One of ordinary skill in the art would be able to determine such therapeutically effective amounts based on such factors as the subject's size, the severity of symptoms, and the particular composition or route of administration selected. For example, a therapeutically effective amount of a compound can decrease tumor size or otherwise ameliorate symptoms associated with a particular disorder in a subject. The dsRNA molecules of the instant disclosure, individually or in combination or in conjunction with other drugs, can be used to treat diseases or conditions discussed herein, by administering to a subject or by administering to particular cells under conditions suitable for treatment.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure. As described herein, all value ranges are inclusive over the indicated range. Thus, a range of $C_1$-$C_4$ will be understood to include the values of 1, 2, 3, and 4, such that $C_1$, $C_2$, $C_3$ and $C_4$ are included.

The term "alkyl" as used herein refers to saturated straight- or branched-chain aliphatic groups containing from 1-20 carbon atoms, preferably 1-8 carbon atoms and most preferably 1-4 carbon atoms. This definition applies as well to the alkyl portion of alkoxy, alkanoyl and aralkyl groups. The alkyl group may be substituted or unsubstituted. In certain embodiments, the alkyl is a ($C_1$-$C_4$) alkyl or methyl.

The term "cycloalkyl" as used herein refers to a saturated cyclic hydrocarbon ring system containing from 3 to 12 carbon atoms that may be optionally substituted. Exemplary embodiments include, but are not limited to, cyclopropyl, cyclobutyl, cyclopentyl and cyclohexyl. In certain embodiments, the cycloalkyl group is cyclopropyl. In another embodiment, the (cycloalkyl)alkyl groups contain from 3 to 12 carbon atoms in the cyclic portion and 1 to 6 carbon atoms in the alkyl portion. In certain embodiments, the (cycloalkyl) alkyl group is cyclopropylmethyl. The alkyl groups are optionally substituted with from one to three substituents selected from the group consisting of halogen, hydroxy and amino.

The terms "alkanoyl" and "alkanoyloxy" as used herein refer, respectively, to —C(O)-alkyl groups and —O—C(=O)— alkyl groups, each optionally containing 2 to 10 carbon atoms. Specific embodiments of alkanoyl and alkanoyloxy groups are acetyl and acetoxy, respectively.

The term "alkenyl" refers to an unsaturated branched, straight-chain or cyclic alkyl group having 2 to 15 carbon atoms and having at least one carbon-carbon double bond derived by the removal of one hydrogen atom from a single carbon atom of a parent alkene. The group may be in either the cis or trans conformation about the double bond(s). Certain embodiments include ethenyl, 1-propenyl, 2-propenyl, 1-methylethenyl, 1-butenyl, 2-butenyl, 3-butenyl, 2-methyl-2-propenyl, 1-pentenyl, 2-pentenyl, 4-pentenyl, 3-methyl-2-butenyl, 1-hexenyl, 2-hexenyl, 1-heptenyl, 2-heptenyl, 1-octenyl, 2-octenyl, 1,3-octadienyl, 2-nonenyl, 1,3-nonadienyl, 2-decenyl, etc., or the like. The alkenyl group may be substituted or unsubstituted.

The term "alkynyl" as used herein refers to an unsaturated branched, straight-chain, or cyclic alkyl group having 2 to 10 carbon atoms and having at least one carbon-carbon triple bond derived by the removal of one hydrogen atom from a single carbon atom of a parent alkyne. Exemplary alkynyls include ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, 2-decynyl, or the like. The alkynyl group may be substituted or unsubstituted.

The term "hydroxyalkyl" alone or in combination, refers to an alkyl group as previously defined, wherein one or several hydrogen atoms, preferably one hydrogen atom has been replaced by a hydroxyl group. Examples include hydroxymethyl, hydroxyethyl and 2-hydroxyethyl.

The term "aminoalkyl" as used herein refers to the group —NRR', where R and R' may independently be hydrogen or ($C_1$-$C_4$) alkyl.

The term "alkylaminoalkyl" refers to an alkylamino group linked via an alkyl group (i.e., a group having the general structure -alkyl-NH-alkyl or -alkyl-N(alkyl)(alkyl)). Such groups include, but are not limited to, mono- and di-($C_1$-$C_8$ alkyl)amino$C_1$-$C_8$ alkyl, in which each alkyl may be the same or different.

The term "dialkylaminoalkyl" refers to alkylamino groups attached to an alkyl group. Examples include, but are not limited to, N,N-dimethylaminomethyl, N,N-dimethylaminoethyl N,N-dimethylaminopropyl, and the like. The term dialkylaminoalkyl also includes groups where the bridging alkyl moiety is optionally substituted.

The term "haloalkyl" refers to an alkyl group substituted with one or more halo groups, for example, chloromethyl, 2-bromoethyl, 3-iodopropyl, trifluoromethyl, perfluoropropyl, 8-chlorononyl, or the like.

The term "carboxyalkyl" as used herein refers to the substituent —$R^Z$—COOH, wherein $R^{10}$ is alkylene; and carbalkoxyalkyl refers to —$R^{10}$—C(=O)O$R^{11}$, wherein $R^{10}$ and $R^{11}$ are alkylene and alkyl respectively. In certain embodiments, alkyl refers to a saturated straight- or branched-chain hydrocarbyl radical of 1 to 6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent.

The term "alkoxy" includes substituted and unsubstituted alkyl, alkenyl, and alkynyl groups covalently linked to an oxygen atom. In one embodiment, the alkoxy group contains 1 to about 10 carbon atoms. Embodiments of alkoxy groups include, but are not limited to, methoxy, ethoxy, isopropyloxy, propoxy, butoxy, and pentoxy groups. Embodiments of substituted alkoxy groups include halogenated alkoxy groups. In a further embodiment, the alkoxy groups can be substituted with groups such as alkenyl, alkynyl, halogen, hydroxyl, alkylcarbonyloxy, aryloxycarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Exemplary halogen substituted alkoxy groups include, but are not limited to, fluoromethoxy, difluoromethoxy, trifluoromethoxy, chloromethoxy, dichloromethoxy, and trichloromethoxy.

The term "alkoxyalkyl" refers to an alkylene group substituted with an alkoxy group. For example, methoxyethyl ($CH_3OCH_2CH_2$—) and ethoxymethyl ($CH_3CH_2OCH_2$—) are both $C_3$ alkoxyalkyl groups.

The term "aryl" as used herein refers to monocyclic or bicyclic aromatic hydrocarbon groups having from 6 to 12 carbon atoms in the ring portion, for example, phenyl, naphthyl, biphenyl and diphenyl groups, each of which may be substituted with, for example, one to four substituents such as alkyl; substituted alkyl as defined above, halogen, trifluoromethyl, trifluoromethoxy, hydroxy, alkoxy, cycloalkyloxy, alkanoyl, alkanoyloxy, amino, alkylamino, dialkylamino, nitro, cyano, carboxy, carboxyalkyl, carbamyl, carbamoyl and aryloxy. Specific embodiments of aryl groups in accordance with the present disclosure include phenyl, substituted phenyl, naphthyl, biphenyl, and diphenyl.

The term "aroyl" as used alone or in combination herein refers to an aryl radical derived from an aromatic carboxylic acid, such as optionally substituted benzoic or naphthoic acids.

The term "aralkyl" as used herein refers to an aryl group bonded to the 2-pyridinyl ring or the 4-pyridinyl ring through an alkyl group, preferably one containing 1 to 10 carbon atoms. A preferred aralkyl group is benzyl.

The term "carboxy" as used herein represents a group of the formula —C(=O)OH or —C(=O)O$^-$.

The term "carbonyl" as used herein refers to a group in which an oxygen atom is double-bonded to a carbon atom —C=O.

The term "trifluoromethyl" as used herein refers to —$CF_3$.

The term "trifluoromethoxy" as used herein refers to —$OCF_3$.

The term "hydroxyl" as used herein refers to —OH or —O$^-$.

The term "nitrile" or "cyano" as used herein refers to the group —CN.

The term "nitro" as used herein alone or in combination refers to a —$NO_2$ group.

The term "amino" as used herein refers to the group —$NR^9R^9$, wherein $R^9$ may independently be hydrogen, alkyl, aryl, alkoxy, or heteroaryl. The term "aminoalkyl" as used herein represents a more detailed selection as compared to "amino" and refers to the group —NR'R', wherein R' may independently be hydrogen or ($C_1$-$C_4$) alkyl. The term "dialkylamino" refers to an amino group having two attached alkyl groups that can be the same or different.

The term "alkanoylamino" refers to alkyl, alkenyl or alkynyl groups containing the group —C(=O)— followed by —N(H)—, for example, acetylamino, propanoylamino and butanoylamino and the like.

The term "carbonylamino" refers to the group —NR'—CO—$CH_2$—R', wherein R' is independently selected from hydrogen or ($C_1$-$C_4$) alkyl.

The term "carbamoyl" as used herein refers to —O—C(O)$NH_2$.

The term "carbamyl" as used herein refers to a functional group in which a nitrogen atom is directly bonded to a carbonyl, i.e., as in —NR'C(=O)R' or —C(=O)NR'R', wherein R' can be independently hydrogen, alkyl, substituted alkyl, alkenyl, substituted alkenyl, alkoxy, cycloalkyl, aryl, heterocyclo, or heteroaryl.

The term "alkylsulfonylamino" refers to refers to the group —NHS(O)$_2R^{12}$, wherein $R^{12}$ is alkyl.

The term "halogen" as used herein refers to bromine, chlorine, fluorine or iodine. In one embodiment, the halogen is fluorine. In another embodiment, the halogen is chlorine.

The term "heterocyclo" refers to an optionally substituted, unsaturated, partially saturated, or fully saturated, aromatic or nonaromatic cyclic group that is a 4 to 7 membered monocyclic, or 7 to 11 membered bicyclic ring system that has at least one heteroatom in at least one carbon atom-containing ring. The substituents on the heterocyclo rings may be selected from those given above for the aryl groups. Each ring of the heterocyclo group containing a heteroatom may have 1, 2, or 3 heteroatoms selected from nitrogen, oxygen or sulfur. Plural heteroatoms in a given heterocyclo ring may be the same or different.

Exemplary monocyclic heterocyclo groups include pyrrolidinyl, pyrrolyl, indolyl, pyrazolyl, imidazolyl, oxazolyl, isoxazolyl, thiazolyl, furyl, tetrahydrofuryl, thienyl, piperidinyl, piperazinyl, azepinyl, pyrimidinyl, pyridazinyl, tetrahydropyranyl, morpholinyl, dioxanyl, triazinyl and triazolyl. Preferred bicyclic heterocyclo groups include benzothiazolyl, benzoxazolyl, benzothienyl, quinolinyl, tetrahydroisoquinolinyl, benzimidazolyl, benzofuryl, indazolyl, benzisothiazolyl, isoindolinyl and tetrahydroquinolinyl. In more detailed embodiments heterocyclo groups may include indolyl, imidazolyl, furyl, thienyl, thiazolyl, pyrrolidyl, pyridyl and pyrimidyl.

"Substituted" refers to a group in which one or more hydrogen atoms are each independently replaced with the same or different substituent(s). Representative substituents include —X, —Rd, —O—, =O, —OR, —$SR^6$, —S—, =S, —$NR^6R^6$, =$NR^6$, —$CX_3$, —$CF_3$, —CN, —OCN, —SCN, —NO, —$NO_2$, =$N_2$, —$N_3$, —S(=O)$_2$O—, —S(=O)$_2$OH, —S(=O)$_2R^6$, —OS(=O)$_2$O—, —OS(=O)$_2$OH, —OS(=O)$_2R^6$, —P(=O)(O$^-$)$_2$, —P(=O)(OH)(O$^-$), —OP(=O)$_2$(O$^-$), —C(=O)$R^6$, —C(=S)$R^6$, —C(=O)OR$^6$, —C(=O)O$^-$, —C(=S)OR$^6$, —NR$^6$—C(=O)—N(R$^6$)$_2$, —NR$^6$—C(=S)—N(R$^6$)$_2$, and —C(=NR$^6$)NR$^6R^6$, wherein each X is independently a halogen; and each $R^6$ is independently hydrogen, halogen, alkyl, aryl, arylalkyl, arylaryl, arylheteroalkyl, heteroaryl, heteroarylalkyl, NR$^7R^7$, —C(=O)$R^7$, and —S(=O)$_2R^7$; and each $R^7$ is independently hydrogen, alkyl, alkanyl, alkynyl, aryl, arylalkyl, arylheteralkyl, arylaryl, heteroaryl or heteroarylalkyl. Aryl containing substituents, whether or not having one or more substitutions, may be attached in a para (p-), meta (m-) or ortho (o-) conformation, or any combination thereof.

Gapped or Nicked dsRNA Molecules

This disclosure provides compounds, compositions, and methods useful for altering expression or activity of a target gene by RNA interference (RNAi) using small nucleic acid molecules. In more detailed embodiments, this disclosure provides small nucleic acid molecules, such as short interfering nucleic acid (siNA), short interfering RNA (siRNA), double-stranded RNA (dsRNA), nicked double-stranded RNA (ndsRNA), gapped double-stranded RNA (gdsRNA), microRNA (miRNA), short hairpin RNA (shRNA) molecules, or any combination thereof, which have a at least one nick or gap and alter expression of a target gene or family of genes to prevent, treat, or alleviate symptoms of a disease or disorder in a subject (e.g., human). Within these and related therapeutic compositions and methods, the use of nicked or gapped dsRNAs (which have been optionally substituted or modified) will often improve properties of the dsRNA molecules in comparison to the properties of native dsRNA molecules, such as reduced off-target effects, reduced interferon response, increased resistance to nuclease degradation in vivo, improved cellular uptake, increased potency, or any combination thereof.

In particular embodiments, there are provided methods of treating or preventing diseases, disorders, or conditions related to gene expression, including those related, or responsive, to the level of a target nucleic acid molecule (e.g., mRNA) in a cell or tissue, by administering a gapped dsRNA (mdRNA) molecule of this disclosure, alone or in combination with an adjunctive therapy, in an amount sufficient to activate target gene-specific RNAi. In one embodiment, there is provided a method of treating or preventing a disease or disorder by administering a dsRNA molecule that is capable of target gene-specific RNAi, which dsRNA has at least one substitution or modification as described herein and has a reduced or minimal off-target effect.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

In one aspect, the instant disclosure provides a meroduplex ribonucleic acid (mdRNA) molecule, comprising a first strand that is complementary to a target mRNA, and a second strand and a third strand that is each complementary to non-overlapping regions of the first strand, wherein the second strand and third strands can anneal with the first strand to form at least two double-stranded regions separated by a gap of up to 10 nucleotides, and wherein (a) at least one double-stranded region comprises from about 5 base pairs to 13 base pairs, or (b) wherein the combined double-stranded regions total about 15 base pairs to about 40 base pairs and the mdRNA molecule comprises blunt ends; wherein at least one pyrimidine of the mdRNA is substituted with a pyrimidine nucleoside according to Formula I or II:

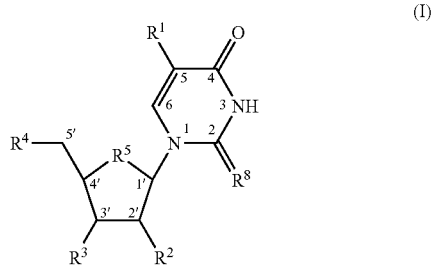

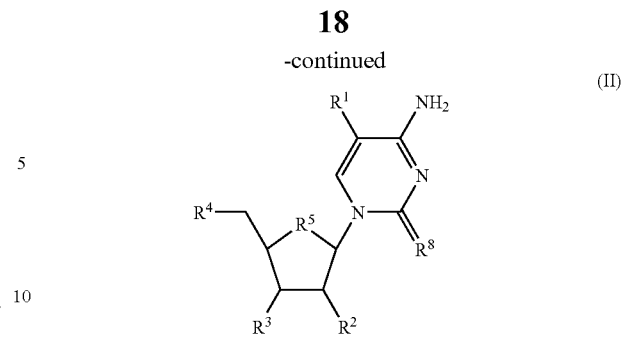

wherein $R^1$ and $R^2$ are each independently a —H, —OH, —OCH$_3$, —OCH$_2$OCH$_2$CH$_3$, —OCH$_2$CH$_2$OCH$_3$, halogen, substituted or unsubstituted C$_1$-C$_{10}$ alkyl, alkoxy, alkoxyalkyl, hydroxyalkyl, carboxyalkyl, alkylsulfonylamino, aminoalkyl, dialkylamino, alkylaminoalkyl, dialkylaminoalkyl, haloalkyl, trifluoromethyl, cycloalkyl, (cycloalkyl)alkyl, substituted or unsubstituted C$_2$-C$_{10}$ alkenyl, substituted or unsubstituted —O-allyl, —O—CH$_2$CH=CH$_2$, —O—CH=CHCH$_3$, substituted or unsubstituted C$_2$-C$_{10}$ alkynyl, carbamoyl, carbamyl, carboxy, carbonylamino, substituted or unsubstituted aryl, substituted or unsubstituted aralkyl, —NH$_2$, —NO$_2$, —C≡, or heterocyclo group; $R^3$ and $R^4$ are each independently a hydroxyl, a protected hydroxyl, a phosphate, or an internucleoside linking group; and $R^5$ and $R^8$ are independently O or S. In certain embodiments, at least one nucleoside is according to Formula I in which $R^1$ is methyl and $R^2$ is —OH, or $R^1$ is methyl, $R^2$ is —OH and $R^8$ is S.

In other embodiments, the internucleoside linking group covalently links from about 5 to about 40 nucleosides. In some embodiments, the gap comprises at least one unpaired nucleotide in the first strand positioned between the double-stranded regions formed by the second and third strands when annealed to the first strand, or the gap comprises a nick. In certain embodiments, the nick or gap is located about 10 nucleotides from the 5'-end of the first strand or at the Argonaute cleavage site. In another embodiment, the meroduplex nick or gap is positioned such that the thermal stability is maximized for the first and second strand duplex and for the first and third strand duplex as compared to the thermal stability of such meroduplexes having a nick or gap in a different position—that is, the nick or gap is located in a position wherein each of the two or more nicked or gapped strands has a maximal melting temperature when annealed to the first strand (i.e., $T_m$ or temperature at which 50% of one of the nicked or gapped strands is annealed to the first strand).

As provided herein, any of the aspects or embodiments disclosed herein would be useful in treating target gene associated diseases or disorders, such as hyperproliferative disease (e.g., cervical cancer, ovarian cancer), angiogenic disorders (e.g., tumor angiogenesis), or inflammatory disorders (e.g. rheumatoid arthritis, rheumatoid arthritis, chronic obstructive bowel disease, atherosclerosis), respiratory disease, pulmonary disease, cardiovascular disease, autoimmune disease, allergic disorders, neurologic disease, infectious disease (e.g., viral infection, such as influenza), renal disease, transplant rejection, or any other disease or condition that responds to modulation of a target gene or gene family. In certain embodiments of the instant disclosure, a single dsRNA can be used to knockdown mRNA expression of one or more target gene family member.

In some embodiments, the dsRNA comprises at least three strands in which the first strand comprises about 5 nucleotides to about 40 nucleotides, and the second and third strands include each, individually, about 5 nucleotides to about 20 nucleotides, wherein the combined length of the second and third strands is about 15 nucleotides to about 40 nucleotides. In other embodiments, the dsRNA comprises at least two or three strands in which the first strand comprises about 15 nucleotides to about 24 nucleotides or about 25 nucleotides to about 40 nucleotides. In further embodiments, the first strand will be complementary to a second strand or a second and third strand or to a plurality of strands. In further examples, the first strand and its complement(s) will be able to form a dsRNA or mdRNA molecules of this disclosure with about 19 to about 25 nucleotides of the first strand that is complementary to at least one target gene mRNA.

For example, a Dicer substrate dsRNA can have about 25 nucleotides to about 40 nucleotides with only 19 nucleotides of the antisense (first) strand being complementary to at least one target gene family mRNA. In further embodiments, the first strand can have complementarity with a target gene family mRNA in about 19 nucleotides to about 25 nucleotides and have one, two, or three mismatches, or any combination thereof, with a target gene family mRNA or any combination thereof, or the first strand of about 19 nucleotides to about 25 nucleotides (that, e.g., activates or is capable of loading into or associating with RISC) can have at least 80% identity with the corresponding nucleotides found in at least one target gene family mRNA, or any combination thereof.

Substituted and Modified Nicked or Gapped dsRNA Molecules

The introduction of substituted and modified nucleotides into mdRNA and dsRNA molecules of this disclosure provides a tool for overcoming potential limitations of in vivo stability and bioavailability inherent to native RNA molecules (i.e., having standard nucleotides) that are exogenously delivered. In certain embodiments, the use of substituted or modified dsRNA molecules of this disclosure can enable a lower dose of a particular nucleic acid molecule for a given therapeutic effect since of dsRNA molecules may be designed to have an increased melting temperature or half-life in a subject or biological samples (e.g., serum). Furthermore, certain substitutions or modifications can be used to improve the bioavailability of dsRNA by targeting particular cells or tissues or improving cellular uptake of the dsRNA molecules. Therefore, even if the activity of a dsRNA molecule of this disclosure is reduced as compared to a native RNA molecule, the overall activity of the substituted or modified dsRNA molecule can be greater than that of the native RNA molecule due to improved stability or delivery of the molecule. The mdRNA structure may result in a reduced interferon response, and substituted and modified dsRNA can also minimize the possibility of activating an interferon response in, for example, humans.

In certain embodiments, a dsRNA molecule of this disclosure has at least one uridine, at least three uridines, or each and every uridine (i.e., all uridines) of the first (antisense) strand of the dsRNA substituted or replaced with 5-methyluridine or 2-thioribothymidine. In a related embodiment, the dsRNA molecule or analog thereof of this disclosure has at least one uridine, at least three uridines, or each and every uridine of the second (sense) strand of the dsRNA substituted or replaced with 5-methyluridine or 2-thioribothymidine. In still another embodiment, the dsRNA molecule or analog thereof of this disclosure has at least one uridine, at least three uridines, or each and every uridine of both the first (antisense) and second (sense) strands of the dsRNA substituted or replaced with 5-methyluridine or 2-thioribothymidine. In some embodiments, the double-stranded region of a dsRNA molecule has at least three 5-methyluridines or 2-thioribothymidines. In certain embodiments, dsRNA molecules comprise ribonucleotides at about 5% to about 95% of the nucleotide positions in one strand, both strands, or any combination thereof.

In further embodiments, a dsRNA molecule that decreases expression of one or more target gene by RNAi according to the instant disclosure further comprises one or more natural or synthetic non-standard nucleoside. In related embodiments, the non-standard nucleoside is one or more deoxyuridine, L- or D-locked nucleic acid (LNA) molecule (e.g., a 5-methyluridine LNA) or substituted LNA (e.g., having a pyrene), or a universal-binding nucleotide, or a G clamp, or any combination thereof. In certain embodiments, the universal-binding nucleotide can be C-phenyl, C-naphthyl, inosine, azole carboxamide, 1-β-D-ribofuranosyl-4-nitroindole, 1-β-D-ribofuranosyl-5-nitroindole, 1-β-D-ribofuranosyl-6-nitroindole, or 1-β-D-ribofuranosyl-3-nitropyrrole.

Substituted or modified nucleotides present in dsRNA molecules, preferably in the antisense strand, but also optionally in the sense or both the antisense and sense strands, comprise modified or substituted nucleotides according to this disclosure having properties or characteristics similar to natural or standard ribonucleotides. For example, this disclosure features dsRNA molecules including nucleotides having a Northern conformation (e.g., Northern pseudorotation cycle, see, e.g., Saenger, *Principles of Nucleic Acid Structure*, Springer-Verlag ed., 1984). As such, chemically modified nucleotides present in dsRNA molecules of this disclosure, preferably in the antisense strand, but also optionally in the sense or both the antisense and sense strands, are resistant to nuclease degradation while at the same time maintaining the capacity to mediate RNAi. Exemplary nucleotides having a Northern configuration include locked nucleic acid (LNA) nucleotides (e.g., 2'O, 4'-C-methylene-(D-ribofuranosyl) nucleotides), 2'-methoxyethyl (MOE) nucleotides, 2' methyl-thio-ethyl, 2' deoxy-2' fluoro nucleotides, 2' deoxy-2' chloro nucleotides, 2' azido nucleotides, 5-methyluridines, or 2'O-methyl nucleotides. In certain embodiments, the LNA is a 5-methyluridine LNA or 2-thioribothymidine LNA. In any of these embodiments, one or more substituted or modified nucleotides can be a G clamp (e.g., a cytosine analog that forms an additional hydrogen bond to guanine, such as 9-(aminoethoxy)phenoxazine; see, e.g., Lin and Mateucci, *J. Am. Chem. Soc.* 120:8531, 1998).

As described herein, the first and one or more second strands of a dsRNA molecule or analog thereof provided by this disclosure can anneal or hybridize together (i.e., due to complementarity between the strands) to form at least one double-stranded region having a length of about 4 to about 10 base pairs, about 5 to about 13 base pairs, or about 15 to about 40 base pairs. In some embodiments, the dsRNA has at least one double-stranded region ranging in length from about 15 to about 24 base pairs or about 19 to about 23 base pairs. In other embodiments, the dsRNA has at least one double-stranded region ranging in length from about 26 to about 40 base pairs or about 27 to about 30 base pairs or about 30 to about 35 base pairs. In other embodiments, the two or more strands of a dsRNA molecule of this disclosure may optionally be covalently linked together by nucleotide or non-nucleotide linker molecules.

In certain embodiments, the dsRNA molecule or analog thereof comprises an overhang of one to four nucleotides on one or both 3'-ends of the dsRNA, such as an overhang comprising a deoxyribonucleotide or two deoxyribonucleotides (e.g., thymidine, adenine). In certain embodiments, the 3'-end comprising one or more deoxyribonucleotide is in an mdRNA molecule and is either in the gap, not in the gap, or any combination thereof. In some embodiments, dsRNA molecules or analogs thereof have a blunt end at one or both ends of the dsRNA. In certain embodiments, the 5'-end of the first or second strand is phosphorylated. In any of the embodiments of dsRNA molecules described herein, the 3'-terminal nucleotide overhangs can comprise ribonucleotides or deoxyribonucleotides that are chemically-modified at a nucleic acid sugar, base, or backbone. In any of the embodiments of dsRNA molecules described herein, the 3'-terminal nucleotide overhangs can comprise one or more universal base ribonucleotides. In any of the embodiments of dsRNA molecules described herein, the 3'-terminal nucleotide overhangs can comprise one or more acyclic nucleotides. In any of the embodiments of dsRNA molecules described herein, the dsRNA can further comprise a terminal phosphate group, such as a 5' phosphate (see Martinez et al., *Cell* 110:563, 2002; and Schwarz et al., *Molec. Cell* 10:537, 2002) or a 5'3' diphosphate.

As set forth herein, the terminal structure of dsRNAs of this disclosure that decrease expression of one or more target gene by, for example, RNAi may either have blunt ends or one or more overhangs. In certain embodiments, the overhang may be at the 3' end or the 5' end. The total length of dsRNAs having overhangs is expressed as the sum of the length of the paired double-stranded portion together with the overhanging nucleotides. For example, if a 19 base pair dsRNA has a two nucleotide overhang at both ends, the total length is expressed as 21-mer. Furthermore, since the overhanging sequence may have low specificity to one or more target gene, it is not necessarily complementary (antisense) or identical (sense) to a target gene sequence. In further embodiments, a dsRNA of this disclosure that decreases expression of one or more target gene by RNAi may further comprise a low molecular weight structure (e.g., a natural RNA molecule such as a tRNA, rRNA or viral RNA, or an artificial RNA molecule) at, for example, one or more overhanging portion of the dsRNA.

In further embodiments, a dsRNA molecule that decreases expression of one or more target gene by RNAi according to the instant disclosure comprises a 2'-sugar substitution, such as a 2'-deoxy, 2'-O-2-methoxyethyl, 2'-O-methoxyethyl, 2'-O-methyl, halogen, 2'-fluoro, 2'-O-allyl, or the like, or any combination thereof. In still further embodiments, a dsRNA molecule that decreases expression of one or more target gene by RNAi according to the instant disclosure further comprises a terminal cap substituent on one or both ends of the first strand or one or more second strands, such as an alkyl, abasic, deoxy abasic, glyceryl, dinucleotide, acyclic nucleotide, inverted deoxynucleotide moiety, or any combination thereof. In certain embodiments, at least one or two 5'-terminal ribonucleotides of the sense strand within the double-stranded region have a 2'-sugar substitution. In certain other embodiments, at least one or two 5'-terminal ribonucleotides of the antisense strand within the double-stranded region have a 2'-sugar substitution. In certain embodiments, at least one or two 5'-terminal ribonucleotides of the sense strand and the antisense strand within the double-stranded region have a 2'-sugar substitution.

In other embodiments, a dsRNA molecule that decreases expression of one or more target gene by RNAi according to the instant disclosure comprises one or more substitutions in the sugar backbone, including any combination of ribosyl, 2'-deoxyribosyl, a tetrofuranosyl (e.g., L-α-threofuranosyl), a hexopyranosyl (e.g., β-allopyranosyl, β-altropyranosyl, and β-glucopyranosyl), a pentopyranosyl (e.g., β-ribopyranosyl, α-lyxopyranosyl, β-xylopyranosyl, and α-arabinopyranosyl), a carbocyclic (carbon only ring) analog, a pyranose, a furanose, a morpholino, or analogs or derivatives thereof.

In yet other embodiments, a dsRNA molecule that decreases expression of one or more target gene by RNAi according to the instant disclosure comprises at least one modified internucleoside linkage, such as independently a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, boranophosphate linkage, or any combination thereof.

A modified internucleotide linkage, as described herein, can be present in one or more strands of a dsRNA molecule of this disclosure, for example, in the sense strand, the antisense strand, both strands, or a plurality of strands (e.g., in an mdRNA). The dsRNA molecules of this disclosure can comprise one or more modified internucleotide linkages at the 3' end, the 5' end, or both of the 3' and 5' ends of the sense strand or the antisense strand or both strands. In one embodiment, a dsRNA molecule capable of decreasing expression of one or more target gene by RNAi has one modified internucleotide linkage at the 3'-end, such as a phosphorothioate linkage. For example, this disclosure provides a dsRNA molecule capable of decreasing expression of one or more target gene by RNAi having about 1 to about 8 or more phosphorothioate internucleotide linkages in one dsRNA strand. In yet another embodiment, this disclosure provides a dsRNA molecule capable of decreasing expression of one or more target gene by RNAi having about 1 to about 8 or more phosphorothioate internucleotide linkages in both dsRNA strands. In other embodiments, an exemplary dsRNA molecule of this disclosure can comprise from about 1 to about 5 or more consecutive phosphorothioate internucleotide linkages at the 5' end of the sense strand, the antisense strand, both strands, or a plurality of strands. In another example, an exemplary dsRNA molecule of this disclosure can comprise one or more pyrimidine phosphorothioate internucleotide linkages in the sense strand, the antisense strand, two strands, or a plurality of strands. In yet another example, an exemplary dsRNA molecule of this disclosure can comprise one or more purine phosphorothioate internucleotide linkages in the sense strand, the antisense strand, two strands, or a plurality of strands.

Many exemplary modified nucleotide bases or analogs thereof useful in the dsRNA of the instant disclosure include 5-methylcytosine; 5-hydroxymethylcytosine; xanthine; hypoxanthine; 2-aminoadenine; 6-methyl, 2-propyl, or other alkyl derivatives of adenine and guanine; 8-substituted adenines and guanines (such as 8-aza, 8-halo, 8-amino, 8-thiol, 8-thioalkyl, 8-hydroxyl, or the like); 7-methyl, 7-deaza, and 3-deaza adenines and guanines; 2-thiouracil; 2-thiothymine; 2-thiocytosine; 5-methyl, 5-propynyl, 5-halo (such as 5-bromo or 5-fluoro), 5-trifluoromethyl, or other 5-substituted uracils and cytosines; and 6-azouracil. Further useful nucleotide bases can be found in Kurreck, *Eur. J. Biochem.* 270:1628, 2003; Herdewijn, *Antisense Nucleic Acid Develop.* 10:297, 2000; Concise Encyclopedia of Polymer Science and Engineering, pages 858-859, Kroschwitz, J. I., ed. John Wiley & Sons, 1990; U.S. Pat. No. 3,687,808, and similar references.

Certain nucleotide base moieties are particularly useful for increasing the binding affinity of the dsRNA molecules of this disclosure to complementary targets. These include 5-substituted pyrimidines; 6-azapyrimidines; and N-2, N-6, or O-6 substituted purines (including 2-aminopropyladenine, 5-propynyluracil and 5-propynylcytosine). Further, for example, 5-methyluridine and 5-methylcytosine substitutions are known to increase nucleic acid duplex stability, which can be combined with 2'-sugar modifications (such as 2'-methoxy or 2'-methoxyethyl) or internucleoside linkages (e.g., phosphorothioate) that provide the desired nuclease resistance to the modified or substituted dsRNA.

In another aspect of the instant disclosure, there is provided a dsRNA that decreases expression of one or more target gene, comprising a first strand that is complementary to a target gene mRNA, or any combination thereof, and a second strand that is complementary to the first strand, wherein the first and second strands form a double-stranded region of about 15 to about 40 base pairs; wherein at least one pyrimidine of the dsRNA is substituted with a pyrimidine nucleoside according to Formula I or II:

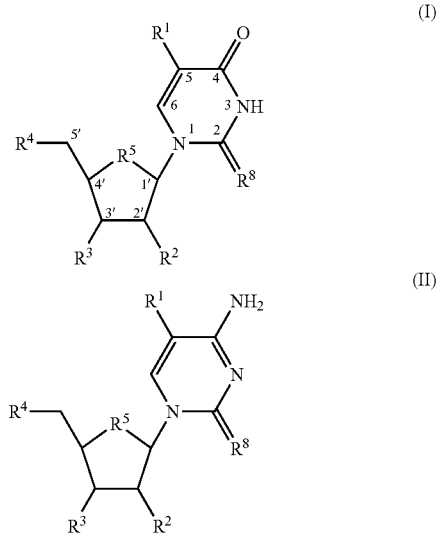

wherein $R^1$ and $R^2$ are each independently a —H, —OH, —OCH$_3$, —OCH$_2$OCH$_2$CH$_3$, —OCH$_2$CH$_2$OCH$_3$, halogen, substituted or unsubstituted $C_1$-$C_{10}$ alkyl, alkoxy, alkoxyalkyl, hydroxyalkyl, carboxyalkyl, alkylsulfonylamino, aminoalkyl, dialkylamino, alkylaminoalkyl, dialkylaminoalkyl, haloalkyl, trifluoromethyl, cycloalkyl, (cycloalkyl)alkyl, substituted or unsubstituted $C_2$-$C_{10}$ alkenyl, substituted or unsubstituted —O-allyl, —O—CH$_2$CH=CH$_2$, —O—CH=CHCH$_3$, substituted or unsubstituted $C_2$-$C_{10}$ alkynyl, carbamoyl, carbamyl, carboxy, carbonylamino, substituted or unsubstituted aryl, substituted or unsubstituted aralkyl, —NH$_2$, —NO$_2$, —C≡, or heterocyclo group; $R^3$ and $R^4$ are each independently a hydroxyl, a protected hydroxyl, or an internucleoside linking group; and $R^5$ and $R^8$ are independently O or S. In certain embodiments, at least one nucleoside is according to Formula I in which $R^1$ is methyl and $R^2$ is —OH or $R^1$ is methyl, $R^2$ is —OH, and $R^8$ is S. In other embodiments, the internucleoside linking group covalently links from about 5 to about 40 nucleosides.

In certain embodiments, the first and one or more second strands of a dsRNA, which decreases expression of one or more target gene by RNAi and has at least one pyrimidine substituted with a pyrimidine nucleoside according to Formula I or II, can anneal or hybridize together (i.e., due to complementarity between the strands) to form at least one double-stranded region having a length or a combined length of about 15 to about 40 base pairs. In some embodiments, the dsRNA has at least one double-stranded region ranging in length from about 4 base pairs to about 10 base pairs or about 5 to about 13 base pairs or about 15 to about 25 base pairs or about 19 to about 23 base pairs. In other embodiments, the dsRNA has at least one double-stranded region ranging in length from about 26 to about 40 base pairs or about 27 to about 30 base pairs or about 30 to about 35 base pairs. In certain embodiments, the dsRNA molecule or analog thereof has an overhang of one to four nucleotides on one or both 3'-ends, such as an overhang comprising a deoxyribonucleotide or two deoxyribonucleotides (e.g., thymidine). In some embodiments, dsRNA molecule or analog thereof has a blunt end at one or both ends of the dsRNA. In certain embodiments, the 5'-end of the first or second strand is phosphorylated.

In certain embodiments, at least one $R^1$ is a $C_1$-$C_5$ alkyl, such as methyl or ethyl. Within other exemplary embodiments of this disclosure, compounds of Formula I are a 5-alkyluridine (i.e., $R^1$ is alkyl, $R^2$ is —OH, and $R^3$, $R^4$, and $R^5$ are as defined herein) or compounds of Formula II are a 5-alkylcytidine (i.e., $R^1$ is alkyl, $R^2$ is —OH, and $R^3$, $R^4$, and $R^5$ are as defined herein). In related embodiments, the 5-alkyluridine is a 5-methyluridine (also referred to as ribothymidine or 't' or 'T'"—i.e., $R^1$ is methyl and $R^2$ is —OH), and the 5-alkylcytidine is a 5-methylcytidine. In other embodiments, at least one, at least three, or all uridines of the first strand of the dsRNA are replaced with 5-methyluridine, or at least one, at least three, or all uridines of the second strand of the dsRNA are replaced with 5-methyluridine, or any combination thereof (e.g., such changes are made on both strands). In certain embodiments, at least one pyrimidine nucleoside of Formula I or Formula II has an $R^5$ that is S or $R^8$ that is S.

In further embodiments, at least one pyrimidine nucleoside of the dsRNA is a locked nucleic acid (LNA) in the form of a bicyclic sugar, wherein $R^2$ is oxygen, and the 2'O and 4'C form an oxymethylene bridge on the same ribose ring. In a related embodiment, the LNA comprises a base substitution, such as a 5-methyluridine LNA or 2-thio-5-methyluridine LNA. In other embodiments, at least one, at least three, or all uridines of the first strand of the dsRNA are replaced with 5-methyluridine or 2-thioribothymidine or 5-methyluridine LNA or 2-thio-5-methyluridine LNA, or at least one, at least three, or all uridines of the second strand of the dsRNA are replaced with 5-methyluridine, 2-thioribothymidine, 5-methyluridine LNA, 2-thio-5-methyluridine LNA, or any combination thereof (e.g., such changes are made on both strands, or some substitutions include 5-methyluridine only, 2-thioribothymidine only, 5-methyluridine LNA only, 2-thio-5-methyluridine LNA only, or one or more 5-methyluridine or 2-thioribothymidine with one or more 5-methyluridine LNA or 2-thio-5-methyluridine LNA).

In further embodiments, a ribose of the pyrimidine nucleoside or the internucleoside linkage can be optionally modified. For example, compounds of Formula I or II are provided wherein $R^2$ is alkoxy, such as a 2'O-methyl substitution (e.g., which may be in addition to a 5-alkyluridine or a 5-alkylcytidine, respectively). In certain embodiments, $R^2$ is selected from 2'O—($C_1$-$C_5$) alkyl, 2'O-methyl, 2'OCH$_2$OCH$_2$CH$_3$, 2'OCH$_2$CH$_2$OCH$_3$, 2'O-allyl, or 2'-fluoro. In further embodiments, one or more of the pyrimidine nucleosides are according to Formula I in which $R^1$ is methyl and $R^2$ is a 2'O—($C_1$-$C_5$) alkyl (e.g., 2'O-methyl), or in which $R^1$ is methyl, $R^2$ is a 2'O—($C_1$-$C_5$) alkyl (e.g., 2'O-methyl), and $R^5$ or $R^8$ is S, or any combination thereof. In other embodiments, one or more, or at least two, pyrimidine nucleosides according to Formula I or II have an $R^2$ that is not —H or —OH and is incorporated at a 3' end or 5' end and not within the gap of one or more strands within the double-stranded region of the dsRNA molecule.

In further embodiments, a dsRNA molecule or analog thereof comprising a pyrimidine nucleoside according to Formula I or Formula II in which $R^2$ is not —H or —OH and an overhang, further comprises at least two of pyrimidine nucleosides that are incorporated either at a 3' end or a 5' end or both of one strand or two strands within the double-stranded region of the dsRNA molecule. In a related embodiment, at least one of the at least two pyrimidine nucleosides in which $R^2$ is not —H or —OH is located at a 3' end or a 5' end within the double-stranded region of at least one strand of the dsRNA molecule, and wherein at least one of the at least two pyrimidine nucleosides in which $R^2$ is not —H or —OH is located internally within a strand of the dsRNA molecule. In still further embodiments, a dsRNA molecule or analog thereof that has an overhang has a first of the two or more pyrimidine nucleosides in which $R^2$ is not —H or —OH that is incorporated at a 5' end within the double-stranded region of the sense strand of the dsRNA molecule and a second of the two or more pyrimidine nucleosides is incorporated at a 5' end within the double-stranded region of the antisense strand of the dsRNA molecule. In any of these embodiments, one or more substituted or modified nucleotides can be a G clamp (e.g., a cytosine analog that forms an additional hydrogen bond to guanine, such as 9-(aminoethoxy)phenoxazine; see, e.g., Lin and Mateucci, 1998). In any of these embodiments, provided the one or more pyrimidine nucleosides are not within the gap.

In yet other embodiments, a dsRNA molecule or analog thereof of Formula I or II according to the instant disclosure that has an overhang comprises four or more independent pyrimidine nucleosides or four or more independent pyrimidine nucleosides in which $R^2$ is not —H or —OH, wherein (a) a first pyrimidine nucleoside is incorporated into a 3' end within the double-stranded region of the sense (second) strand of the dsRNA, (b) a second pyrimidine nucleoside is incorporated into a 5' end within the double-stranded region of the sense (second) strand, (c) a third pyrimidine nucleoside is incorporated into a 3' end within the double-stranded region of the antisense (first) strand of the dsRNA, and (d) a fourth pyrimidine nucleoside is incorporated into a 5' end within the double-stranded region of the antisense (first) strand. In any of these embodiments, provided the one or more pyrimidine nucleosides are not within the gap.

In further embodiments, a dsRNA molecule or analog thereof comprising a pyrimidine nucleoside according to Formula I or Formula II in which $R^2$ is not —H or —OH and is blunt-ended, further comprises at least two of pyrimidine nucleosides that are incorporated either at a 3' end or a 5' end or both of one strand or two strands of the dsRNA molecule. In a related embodiment, at least one of the at least two pyrimidine nucleosides in which $R^2$ is not —H or —OH is located at a 3' end or a 5' end of at least one strand of the dsRNA molecule, and wherein at least one of the at least two pyrimidine nucleosides in which $R^2$ is not —H or —OH is located internally within a strand of the dsRNA molecule. In still further embodiments, a dsRNA molecule or analog thereof that is blunt-ended has a first of the two or more pyrimidine nucleosides in which $R^2$ is not —H or —OH that is incorporated at a 5' end of the sense strand of the dsRNA molecule and a second of the two or more pyrimidine nucleosides is incorporated at a 5' end of the antisense strand of the dsRNA molecule. In any of these embodiments, provided the one or more pyrimidine nucleosides are not within the gap.

In yet other embodiments, a dsRNA molecule comprising a pyrimidine nucleoside according to Formula I or II and that is blunt-ended comprises four or more independent pyrimidine nucleosides or four or more independent pyrimidine nucleosides in which $R^2$ is not —H or —OH, wherein (a) a first pyrimidine nucleoside is incorporated into a 3' end within the double-stranded region of the sense (second) strand of the dsRNA, (b) a second pyrimidine nucleoside is incorporated into a 5' end within the double-stranded region of the sense (second) strand, (c) a third pyrimidine nucleoside is incorporated into a 3' end within the double-stranded region of the antisense (first) strand of the dsRNA, and (d) a fourth pyrimidine nucleoside is incorporated into a 5' end within the double-stranded region of the antisense (first) strand. In any of these embodiments, provided the one or more pyrimidine nucleosides are not within the gap.

In still further embodiments, a dsRNA molecule or analog thereof of Formula I or II according to the instant disclosure further comprises a terminal cap substituent on one or both ends of the first strand or second strand, such as an alkyl, abasic, deoxy abasic, glyceryl, dinucleotide, acyclic nucleotide, inverted deoxynucleotide moiety, or any combination thereof. In further embodiments, one or more internucleoside linkage can be optionally modified. For example, a dsRNA molecule or analog thereof of Formula I or II according to the instant disclosure wherein at least one internucleoside linkage is modified to a phosphorothioate, chiral phosphorothioate, phosphorodithioate, phosphotriester, aminoalkylphosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, aminoalkylphosphoramidate, thionophosphoramidate, thionoalkylphosphonate, thionoalkylphosphotriester, selenophosphate, boranophosphate linkage, or any combination thereof.

In still another embodiment, provided is a nicked or gapped dsRNA molecule (ndsRNA or gdsRNA, respectively) that decreases expression of one or more target gene by RNAi, which comprises a first strand that is complementary to a target gene mRNA, or any combination thereof, and two or more second strands that are complementary to the first strand, wherein the first and at least one of the second strands form a non-overlapping double-stranded region of about 5 to about 13 base pairs. Any of the aforementioned substitutions or modifications is contemplated within this embodiment as well.

In another exemplary of this disclosure, the dsRNAs comprise at least two or more substituted pyrimidine nucleosides can each be independently selected wherein $R^1$ comprises any chemical modification or substitution as contemplated herein, for example, an alkyl (e.g., methyl), halogen, hydroxy, alkoxy, nitro, amino, trifluoromethyl, cycloalkyl, (cycloalkyl)alkyl, alkanoyl, alkanoyloxy, aryl, aroyl, aralkyl, nitrile, dialkylamino, alkenyl, alkynyl, hydroxyalkyl, aminoalkyl, alkylaminoalkyl, dialkylaminoalkyl, haloalkyl, carboxyalkyl, alkoxyalkyl, carboxy, carbonyl, alkanoylamino, carbamoyl, carbonylamino, alkylsulfonylamino, or heterocyclo group. When two or more modified ribonucleotides are present, each modified ribonucleotide can be independently modified to have the same, or different, modification or substitution at $R^1$ or $R^2$.

In other detailed embodiments, one or more substituted pyrimidine nucleosides according to Formula I or II can be located at any ribonucleotide position, or any combination of ribonucleotide positions, on either or both of the sense and antisense strands of a dsRNA molecule of this disclosure, including at one or more multiple terminal positions as noted above, or at any one or combination of multiple non-terminal ("internal") positions. In this regard, each of the sense and antisense strands can incorporate about 1 to about 6 or more of the substituted pyrimidine nucleosides.

In certain embodiments, when two or more substituted pyrimidine nucleosides are incorporated within a dsRNA of this disclosure, at least one of the substituted pyrimidine nucleosides will be at a 3' or 5' end of one or both strands, and in certain embodiments at least one of the substituted pyrimidine nucleosides will be at a 5' end of one or both strands. In other embodiments, the substituted pyrimidine nucleosides are located at a position corresponding to a position of a pyrimidine in an unmodified dsRNA that is constructed as a homologous sequence for targeting a cognate mRNA, as described herein.

In addition, the terminal structure of the dsRNAs of this disclosure may have a stem-loop structure in which ends of one side of the dsRNA molecule are connected by a linker nucleic acid, e.g., a linker RNA. The length of the double-stranded region (stem-loop portion) can be, for example, about 15 to about 49 basepairs (bp), about 15 to about 35 bp, or about 21 to about 30 bp long. Alternatively, the length of the double-stranded region that is a final transcription product of dsRNAs to be expressed in a target cell may be, for example, approximately about 15 to about 49 bp, about 15 to about 35 bp, or about 21 to about 30 bp long. When linker segments are employed, there is no particular limitation in the length of the linker as long as it does not hinder pairing of the stem portion. For example, for stable pairing of the stem portion and suppression of recombination between DNAs coding for this portion, the linker portion may have a cloverleaf tRNA structure. Even if the linker has a length that would hinder pairing of the stem portion, it is possible, for example, to construct the linker portion to include introns so that the introns are excised during processing of a precursor RNA into mature RNA, thereby allowing pairing of the stem portion. In the case of a stem-loop dsRNA, either end (head or tail) of RNA with no loop structure may have a low molecular weight RNA. As described above, these low molecular weight RNAs may include a natural RNA molecule, such as tRNA, rRNA or viral RNA, or an artificial RNA molecule.

A dsRNA molecule may be comprised of a circular nucleic acid molecule, wherein the dsRNA is about 38 to about 70 nucleotides in length having from about 18 to about 23 base pairs (e.g., about 19 to about 21) wherein the circular oligonucleotide forms a dumbbell shaped structure having about 19 base pairs and two loops. In certain embodiments, a circular dsRNA molecule contains two loop motifs, wherein one or both loop portions of the dsRNA molecule is biodegradable. For example, a circular dsRNA molecule of this disclosure is designed such that degradation of the loop portions of the dsRNA molecule in vivo can generate a double-stranded dsRNA molecule with 3' terminal overhangs, such as 3' terminal nucleotide overhangs comprising from about 1 to about 4 (unpaired) nucleotides.

Substituting pyrimidine nucleosides into a dsRNA according to this disclosure can be chosen to increase resistance to enzymatic degradation, such as exonucleolytic degradation, including 5' exonucleolytic or 3' exonucleolytic degradation. As such, the dsRNAs described herein will exhibit significant resistance to enzymatic degradation compared to a corresponding dsRNA having standard nucleotides, and will thereby possess greater stability, increased half-life, and greater bioavailability in physiological environments (e.g., when introduced into a eukaryotic target cell). In addition to increasing resistance of the substituted or modified dsRNAs to exonucleolytic degradation, the incorporation of one or more pyrimidine nucleosides according to Formula I or II will render dsRNAs can make these molecules more stable and bioavailable than otherwise identical dsRNAs that do not include the substitutions or modifications. In related aspects of this disclosure, dsRNA substitutions or modifications described herein are chosen to improve stability of a modified dsRNA for use within research, diagnostic and treatment methods wherein the modified dsRNA is contacted with a biological sample, for example, a mammalian cell, intracellular compartment, serum or other extracellular fluid, tissue, or other in vitro or in vivo physiological compartment or environment. In one embodiment, diagnosis is performed on an isolated biological sample. In another embodiment, the diagnostic method is performed in vitro. In a further embodiment, the diagnostic method is not performed (directly) on a human or animal body.

In addition to increasing stability of substituted or modified dsRNAs, incorporation of one or more pyrimidine nucleosides according to Formula I or II in a dsRNA designed for gene silencing can be used to yield additional desired functional results, including increasing a melting point of a substituted or modified dsRNA compared to a corresponding, unmodified dsRNA. By thus increasing a dsRNA melting point, the subject substitutions or modifications will often block or reduce the occurrence or extent of partial dehybridization of the substituted or modified dsRNA (that would ordinarily occur and render the unmodified dsRNA more vulnerable to degradation by certain exonucleases), thereby increasing the stability of the substituted or modified dsRNA.

In another aspect of this disclosure, the mdRNA structure can be used to reduce off-target effects, which can be improved with substitutions or modifications described herein, when the mdRNA are contacted with a biological sample (e.g., when introduced into a target eukaryotic cell having specific, and non-specific mRNA species present as potential specific and non-specific targets). Similarly, the mdRNA structure can be used to reduce interferon activation, which can be improved with substitutions or modifications described herein, when the mdRNA is contacted with a biological sample, for example, when introduced into a eukaryotic cell. Hence, substituted or modified dsRNAs (mdRNAs) according to this disclosure are employed in methods of gene silencing, wherein the substituted or modified dsRNAs exhibit reduced or undetectable off-target effects or reduced interferon response compared to a corresponding dsRNA lack a nick or gap or modification.

In further embodiments, dsRNAs of this disclosure can comprise one or more sense (second) strand that is homologous or corresponds to a sequence of a target gene and an antisense (first) strand that is complementary to the sense strand and a sequence of the target gene. In exemplary embodiments, at least one strand of the dsRNA incorporates one or more pyrimidines substituted according to Formula I or II (e.g., wherein the pyrimidine is replaced by one or more 5-methyluridines or 2-thioribothymidines, the ribose is modified to incorporate one or more 2'-O-methyl substitutions, or any combination thereof). These and other multiple substitutions or modifications according to Formula I or II can be introduced into one or more pyrimidines, or into any combination and up to all pyrimidines present in one or both strands of a dsRNA, so long as the dsRNA retains RNAi activity.

In any of the embodiments described herein, the dsRNA may include multiple modifications. For example, a dsRNA having at least one ribothymidine or 2-thioribothymidine may further comprise at least one LNA, 2'-methoxy, 2'-fluoro, 2'-deoxy, phosphorothioate linkage, an inverted base terminal cap, or any combination thereof. In certain embodiments, a dsRNA will have from one to all uridines substituted with ribothymidine and have up to about 75% LNA substitutions. In other embodiments, a dsRNA will have from one to all uridines substituted with ribothymidine and have up to about 75% 2'-methoxy substitutions (and not at the Argonaute cleavage site). In still other embodiments, a dsRNA will have from one to all uridines substituted with ribothymidine and have up to about 100% 2'-fluoro substitutions. In further embodiments, a dsRNA will have from one to all uridines substituted with ribothymidine and have up to about 75% 2'-deoxy substitutions. In further embodiments, a dsRNA will have up to about 75% LNA substitutions and have up to about 75% 2'-methoxy substitutions. In still other embodiments, a dsRNA will have up to about 75% LNA substitutions and have up to about 100% 2'-fluoro substitutions. In further embodiments, a dsRNA will have up to about 75% LNA substitutions and have up to about 75% 2'-deoxy substitutions. In further embodiments, a dsRNA will have up to about 75% 2'-methoxy substitutions and have up to about 100% 2'-fluoro substitutions. In further embodiments, a dsRNA will have up to about 75% 2'-methoxy substitutions and have up to about 75% 2'-deoxy substitutions. In further embodiments, a dsRNA will have up to about 100% 2'-fluoro substitutions and have up to about 75% 2'-deoxy substitutions.

In further multiple modification embodiments, a dsRNA will have from one to all uridines substituted with ribothymidine, up to about 75% LNA substitutions, and up to about 75% 2'-methoxy substitutions. In still further embodiments, a dsRNA will have from one to all uridines substituted with ribothymidine, up to about 75% LNA substitutions, and up to about 100% 2'-fluoro substitutions. In further embodiments, a dsRNA will have from one to all uridines substituted with ribothymidine, up to about 75% LNA substitutions, and up to about 75% 2'-deoxy substitutions. In further embodiments, a dsRNA will have from one to all uridines substituted with ribothymidine, up to about 75% 2'-methoxy substitutions, and up to about 75% 2'-fluoro substitutions. In further embodiments, a dsRNA will have from one to all uridines substituted with ribothymidine, up to about 75% 2'-methoxy substitutions, and up to about 75% 2'-deoxy substitutions. In further embodiments, a dsRNA will have from one to all uridines substituted with ribothymidine, up to about 100% 2'-fluoro substitutions, and up to about 75% 2'-deoxy substitutions. In yet further embodiments, a dsRNA will have from one to all uridines substituted with ribothymidine, up to about 75% LNA substitutions, up to about 75% 2'-methoxy, up to about 100% 2'-fluoro, and up to about 75% 2'-deoxy substitutions. In other embodiments, a dsRNA will have up to about 75% LNA substitutions, up to about 75% 2'-methoxy substitutions, and up to about 100% 2'-fluoro substitutions. In further embodiments, a dsRNA will have up to about 75% LNA substitutions, up to about 75% 2'-methoxy substitutions, and up to about 75% 2'-deoxy substitutions. In further embodiments, a dsRNA will have up to about 75% LNA substitutions, up to about 100% 2'-fluoro substitutions, and up to about 75% 2'-deoxy substitutions. In still further embodiments, a dsRNA will have up to about 75% 2'-methoxy, up to about 100% 2'-fluoro, and up to about 75% 2'-deoxy substitutions.

In any of these multiple modification embodiments, the dsRNA may further comprise up to 100% phosphorothioate internucleoside linkages, from one to ten or more inverted base terminal caps, or any combination thereof. Additionally, any of these multiple modification embodiments may have these multiple modifications on one strand, two strands, three strands, a plurality of strand, or all strands. Finally, in any of these multiple modification dsRNA, the dsRNA must retain gene silencing activity.

Within certain aspects, the present disclosure provides dsRNA that decreases expression of one or more target gene by RNAi, and compositions comprising one or more dsRNA, wherein at least one dsRNA comprises one or more universal-binding nucleotide(s) in the first, second or third position in the anti-codon of the antisense strand of the dsRNA duplex and wherein the dsRNA is capable of specifically binding to one or more target sequence, such as an RNA expressed by a target cell. In cases wherein the sequence of a target RNA includes one or more single nucleotide substitutions, dsRNA comprising a universal-binding nucleotide retains its capacity to specifically bind a target RNA, thereby mediating gene silencing and, as a consequence, overcoming escape of the target from dsRNA-mediated gene silencing. Non-limiting examples of universal-binding nucleotides that may be suitably employed in the compositions and methods disclosed herein include inosine, 1-β-D-ribofuranosyl-5-nitroindole, and 1-β-D-ribofuranosyl-3-nitropyrrole. For the purpose of the present disclosure, a universal-binding nucleotide is a nucleotide that can form a hydrogen bonded nucleotide pair with more than one nucleotide type.

Non-limiting examples for the above compositions includes modifying the anti-codons for tyrosine (AUA) or phenylalanine (AAA or GAA), cysteine (ACA or GCA), histidine (AUG or GUG), asparagine (AUU or GUU), isoleucine (UAU) and aspartate (AUC or GUC) within the anti-codon of the antisense strand of the dsRNA molecule.

For example, within certain embodiments, the isoleucine anti-codon UAU, for which AUA is the cognate codon, may be modified such that the third-position uridine (U) nucleotide is substituted with the universal-binding nucleotide inosine I to create the anti-codon UAI. Inosine is an exemplary universal-binding nucleotide that can pair with an adenosine (A), uridine (U), and cytidine (C) nucleotide, but not guanosine (G). This modified anti-codon UAI increases the specific-binding capacity of the dsRNA molecule and thus permits the dsRNA to pair with mRNAs having any one of AUA, UUA, and CUA in the corresponding position of the coding strand thereby expanding the number of available RNA degradation targets to which the dsRNA may specifically bind.

Alternatively, the anti-codon AUA may also or alternatively be modified by substituting a universal-binding nucleotide in the third or second position of the anti-codon such that the anti-codon(s) represented by UAI (third position substitution) or UIU (second position substitution) to generate dsRNA that are capable of specifically binding to AUA, CUA and UUA and AAA, ACA and AUA.

In certain aspects, dsRNA disclosed herein can include between about 1 universal-binding nucleotide and about 10 universal-binding nucleotides. Within certain aspects, the presently disclosed dsRNA may comprise a sense strand that is homologous to a sequence of one or more target gene and an antisense strand that is complementary to the sense strand, with the proviso that at least one nucleotide of the antisense strand of the otherwise complementary dsRNA duplex is replaced by one or more universal-binding nucleotide.

By way of background, within the silencing complex, the dsRNA molecule is positioned so that it can interact or bind to a target RNA. The RISC will encounter thousands of different RNAs that are in a typical cell at any given moment. But, the dsRNA loaded in RISC will specifically anneal with a target RNA that has close complementarity with the antisense of the dsRNA molecule. So, unlike an interferon response to a viral infection, the silencing complex is highly selective in identifying a target RNA. RISC cleaves the captured target RNA strand and releases the two pieces of the RNA (now rendered incapable of directing protein synthesis) and moves on. RISC itself stays intact and is capable of finding and cleaving additional target RNA molecules.

It will be understood that, regardless of the position at which the one or more universal-binding nucleotide is substituted, the dsRNA molecule is capable of binding to a target gene and one or more variant(s) thereof thereby facilitating the degradation of the target gene or variant thereof via Dicer or RISC. Thus, the dsRNA of the present disclosure are suitable for introduction into cells to mediate targeted post-transcriptional gene silencing of one or more target gene or variants thereof. When a dsRNA is inserted into a cell, the dsRNA duplex is then unwound, and the antisense strand anneals with mRNA to form a Dicer substrate or the antisense strand is loaded into an assembly of proteins to form the RNA-induced silencing complex (RISC).

Synthesis of Gapped or Nicked dsRNA Molecules

Exemplary molecules of the instant disclosure are recombinantly produced, chemically synthesized, or a combination thereof. Oligonucleotides (e.g., certain modified oligonucleotides or portions of oligonucleotides lacking ribonucleotides) are synthesized using protocols known in the art, for example, as described in Caruthers et al., *Methods in Enzymol.* 211:3, 1992; Thompson et al., PCT Publication No. WO 99/54459, Wincott et al., *Nucleic Acids Res.* 23:2677, 1995; Wincott et al., *Methods Mol. Bio.* 74:59, 1997; Brennan et al., *Biotechnol Bioeng.* 61:33-45, 1998; and Brennan, U.S. Pat. No. 6,001,311. Synthesis of RNA, including certain dsRNA molecules and analogs thereof of this disclosure, can be made using the procedure as described in Usman et al., *J. Am. Chem. Soc.* 109:7845, 1987; Scaringe et al., *Nucleic Acids Res.* 18:5433, 1990; and Wincott et al., *Nucleic Acids Res.* 23:2677-2684, 1995; Wincott et al., *Methods Mol. Bio.* 74:59, 1997.

In certain embodiments, the nucleic acid molecules of the present disclosure can be synthesized separately and joined together post-synthetically, for example, by ligation (Moore et al., *Science* 256:9923, 1992; Draper et al., PCT Publication No. WO 93/23569; Shabarova et al., *Nucleic Acids Res.* 19:4247, 1991; Bellon et al., *Nucleosides & Nucleotides* 16:951, 1997; Bellon et al., *Bioconjugate Chem.* 8:204, 1997), or by hybridization following synthesis or deprotection.

In further embodiments, dsRNAs of this disclosure that decrease expression of one or more target family gene by RNAi can be made as single or multiple transcription products expressed by a polynucleotide vector encoding one or more dsRNAs and directing their expression within host cells. In these embodiments the double-stranded portion of a final transcription product of the dsRNAs to be expressed within the target cell can be, for example, about 5 to about 40 bp, about 15 to about 24 bp, or about 25 to about 40 bp long. Within exemplary embodiments, double-stranded portions of dsRNAs, in which two or more strands pair up, are not limited to completely paired nucleotide segments, and may contain non-pairing portions due to a mismatch (the corresponding nucleotides are not complementary), bulge (lacking in the corresponding complementary nucleotide on one strand), overhang, or the like. Non-pairing portions can be contained to the extent that they do not interfere with dsRNA formation and function. In certain embodiments, a "bulge" may comprise 1 to 2 non-pairing nucleotides, and the double-stranded region of dsRNAs in which two strands pair up may contain from about 1 to 7, or about 1 to 5 bulges. In addition, "mismatch" portions contained in the double-stranded region of dsRNAs may include from about 1 to 7, or about 1 to 5 mismatches. In other embodiments, the double-stranded region of dsRNAs of this disclosure may contain both bulge and mismatched portions in the approximate numerical ranges specified herein.

A dsRNA or analog thereof of this disclosure may be further comprised of a nucleotide, non-nucleotide, or mixed nucleotide/non-nucleotide linker that joins the sense region of the dsRNA to the antisense region of the dsRNA. In one embodiment, a nucleotide linker can be a linker of more than about 2 nucleotides length up to about 10 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287: 820, 2000; and Jayasena, *Clinical Chem.* 45:1628, 1999).

A non-nucleotide linker may be comprised of an abasic nucleotide, polyether, polyamine, polyamide, peptide, carbohydrate, lipid, polyhydrocarbon, or other polymeric compounds (e.g., polyethylene glycols such as those having between 2 and 100 ethylene glycol units). Specific examples include those described by Seela and Kaiser, *Nucleic Acids Res.* 18:6353, 1990; Seela and Kaiser, *Nucleic Acids Res.* 15:3113, 1987; Cload and Schepartz, *J. Am. Chem. Soc.* 113: 6324, 1991; Richardson and Schepartz, *J. Am. Chem. Soc.* 113:5109, 1991; Ma et al., *Nucleic Acids Res.* 21:2585, 1993; Ma et al., *Biochemistry* 32:1751, 1993; Durand et al., *Nucleic Acids Res.* 18:6353, 1990; McCurdy et al., *Nucleosides & Nucleotides* 10:287, 1991; Jaschke et al., *Tetrahedron Lett.* 34:301, 1993; Ono et al., *Biochemistry* 30:9914, 1991; Arnold et al., International Publication No. WO 89/02439; Usman et al., PCT Publication No. WO 95/06731; Dudycz et al., PCT Publication No. WO 95/11910; and Ferentz and Verdine, *J. Am. Chem. Soc.* 113:4000, 1991. The synthesis of a dsRNA molecule of this disclosure, which can be further modified, comprises: (a) synthesis of two complementary strands of the dsRNA molecule; and (b) annealing the two complementary strands together under conditions suitable to obtain a dsRNA molecule. In another embodiment, synthesis of the two complementary strands of a dsRNA molecule is by solid phase oligonucleotide synthesis. In yet another embodiment, synthesis of the two complementary strands of a dsRNA molecule is by solid phase tandem oligonucleotide synthesis.

Chemically synthesizing nucleic acid molecules with substitutions or modifications (base, sugar, phosphate, or any combination thereof) can prevent their degradation by serum ribonucleases, which may lead to increased potency. See, for example, Eckstein et al., PCT Publication No. WO 92/07065; Perrault et al., *Nature* 344:565, 1990; Pieken et al., *Science* 253:314, 1991; Usman and Cedergren, *Trends in Biochem. Sci.* 17:334, 1992; Usman et al., *Nucleic Acids Symp. Ser.*

31:163, 1994; Beigelman et al., *J. Biol. Chem.* 270:25702, 1995; Burgin et al., *Biochemistry* 35:14090, 1996; Burlina et al., *Bioorg. Med. Chem.* 5:1999-2010, 1997; Thompson et al., Karpeisky et al., *Tetrahedron Lett.* 39:1131, 1998; Earnshaw and Gait, *Biopolymers (Nucleic Acid Sciences)* 48:39-55, 1998; Verma and Eckstein, *Annu. Rev. Biochem.* 67:99-134, 1998; Herdewijn, *Antisense Nucleic Acid Drug Dev.* 10:297, 2000; Kurreck, *Eur. J. Biochem.* 270:1628, 2003; Dorsett and Tuschl, *Nature Rev. Drug Discov.* 3:318, 2004; Rossi et al., PCT Publication No. WO 91/03162; Usman et al., PCT Publication No. WO 93/15187; Beigelman et al., PCT Publication No. WO 97/26270; Woolf et al., PCT Publication No. WO 98/13526; Sproat, U.S. Pat. No. 5,334,711; Usman et al., U.S. Pat. No. 5,627,053; Beigelman et al., U.S. Pat. No. 5,716,824; Ötvös et al., U.S. Pat. No. 5,767,264; Gold et al., U.S. Pat. No. 6,300,074. Each of the above references discloses various substitutions and chemical modifications to the base, phosphate, or sugar moieties of nucleic acid molecules, which can be used in the dsRNAs described herein. For example, oligonucleotides can be modified at the sugar moiety to enhance stability or prolong biological activity by increasing nuclease resistance. Representatives of such sugar modifications include 2' amino, 2'C-allyl, 2'-fluoro, 2'-O-methyl, 2'-O-allyl, or 2'-deoxy. Hence, dsRNA molecules of the instant disclosure can be modified to increase nuclease resistance or duplex stability while substantially retaining or having enhanced RNAi activity as compared to unmodified dsRNA.

There are several examples in the art describing sugar, base and phosphate modifications that can be introduced into nucleic acid molecules with significant enhancement in their nuclease stability and efficacy. For example, oligonucleotides are modified to enhance stability or enhance biological activity by modification with nuclease resistant groups, for example, 2' amino, 2'C-allyl, 2' fluoro, 2'O-methyl, 2'O-allyl, 2'-H, nucleotide base modifications. For a review, see Usman and Cedergren, *TIBS* 17:34, 1992; Usman et al., *Nucleic Acids Symp. Ser.* 31:163, 1994; Burgin et al., *Biochemistry* 35:14090, 1996. Sugar modification of nucleic acid molecules have been extensively described in the art (see Eckstein et al., PCT Publication No. WO 92/07065; Perrault et al., *Nature* 344:565-568, 1990; Pieken et al., *Science* 253:314-317, 1991; Usman and Cedergren, *Trends in Biochem. Sci.* 17:334-339, 1992; Usman et al., PCT Publication No. WO 93/15187; Sproat, U.S. Pat. No. 5,334,711 and Beigelman et al., *J. Biol. Chem.* 270:25702, 1995; Beigelman et al., PCT Publication No. WO 97/26270; Beigelman et al., U.S. Pat. No. 5,716,824; Usman et al., U.S. Pat. No. 5,627,053; Woolf et al., PCT Publication No. WO 98/13526; Thompson et al., Karpeisky et al., *Tetrahedron Lett.* 39:1131, 1998; Earnshaw and Gait, *Biopolymers (Nucleic Acid Sciences)* 48:39-55, 1998; Verma and Eckstein, *Annu. Rev. Biochem.* 67:99-134, 1998; and Burlina et al., *Bioorg. Med. Chem.* 5:1999-2010, 1997. Such publications describe general methods and strategies to determine the location of incorporation of sugar, base or phosphate modifications and the like into nucleic acid molecules without modulating catalysis. In view of such teachings, similar modifications can be used as described herein to modify the dsRNA molecules of the instant disclosure so long as the ability of dsRNA molecules to promote RNAi in cells is not significantly inhibited.

In one embodiment, this disclosure features substituted or modified dsRNA molecules, such as phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, or alkylsilyl, substitutions. For a review of oligonucleotide backbone modifications, see Hunziker and Leumann, *Nucleic Acid Analogues: Synthesis and Properties, in Modern Synthetic Methods, VCH,* 331-417, 1995; and Mesmaeker et al., *ACS,* 24-39, 1994.

In another embodiment, a conjugate molecule can be optionally attached to a dsRNA or analog thereof that decreases expression of one or more target gene by RNAi. For example, such conjugate molecules may be polyethylene glycol, human serum albumin, or a ligand for a cellular receptor that can, for example, mediate cellular uptake. Examples of specific conjugate molecules contemplated by the instant disclosure that can be attached to a dsRNA or analog thereof of this disclosure are described in Vargeese et al., U.S. Patent Application Publication No. 2003/0130186, published Jul. 10, 2003, and U.S. Patent Application Publication No. 2004/0110296, published Jun. 10, 2004. In another embodiment, a conjugate molecule is covalently attached to a dsRNA or analog thereof that decreases expression of one or more target gene by RNAi via a biodegradable linker. In certain embodiments, a conjugate molecule can be attached at the 3' end of either the sense strand, the antisense strand, or both strands of a dsRNA molecule provided herein. In another embodiment, a conjugate molecule can be attached at the 5' end of either the sense strand, the antisense strand, or both strands of the dsRNA or analog thereof. In yet another embodiment, a conjugate molecule is attached both the 3' end and 5' end of either the sense strand, the antisense strand, or both strands of a dsRNA molecule, or any combination thereof. In further embodiments, a conjugate molecule of this disclosure comprises a molecule that facilitates delivery of a dsRNA or analog thereof into a biological system, such as a cell. A person of skill in the art can screen dsRNA of this disclosure having various conjugates to determine whether the dsRNA-conjugate complex possesses improved properties (e.g., pharmacokinetic profile, bioavailability, stability) while maintaining the ability to mediate RNAi in, for example, an animal model as described herein or generally known in the art.

Methods for Selecting dsRNA Molecules Specific for a Target Sequence

As indicated above, the present disclosure also provides methods for selecting dsRNA and analogs thereof capable of specifically binding to one or more target gene while being not specifically binding or minimally binding to non-target genes. The selection process disclosed herein is useful, for example, in eliminating dsRNA analogs that are cytotoxic due to non-specific binding to, and subsequent degradation of, one or more non-target genes.

Methods of the present disclosure do not require a priori knowledge of the nucleotide sequence of every possible gene variant targeted by the dsRNA or analog thereof. In one embodiment, the nucleotide sequence of the dsRNA is selected from a conserved region or consensus sequence of one or more target gene. In another embodiment, the nucleotide sequence of the dsRNA may be selectively or preferentially targeted to a certain sequence contained within an mRNA splice variant of a target gene.

In certain embodiments, methods are provided for selecting one or more dsRNA molecule that decreases expression of one or more target gene by RNAi, comprising a first strand that is complementary to a target gene mRNA, or any combination thereof, and a second strand that is complementary to the first strand, wherein the first and second strands form a double-stranded region of about 15 to about 40 base pairs, and wherein at least one uridine of the dsRNA molecule is replaced with a 5-methyluridine or 2-thioribothymidine, which methods employ "off-target" profiling whereby one or more dsRNA provided herein is contacted with a cell, either in vivo or in vitro, and total target mRNA is collected for use in probing a microarray comprising oligonucleotides having one or more nucleotide sequence from a panel of known genes, including non-target genes (e.g., interferon). The "off-target" profile of the dsRNA provided herein is quantified by determining the number of non-target genes having reduced expression levels in the presence of the candidate dsRNAs. The existence of "off target" binding indicates a dsRNA provided herein that is capable of specifically binding to one or more non-target gene messages. In certain embodiments, a dsRNA as provided herein applicable to therapeutic use will exhibit a greater stability, minimal interferon response, and little or no "off-target" binding.

Still further embodiments provide methods for selecting more efficacious dsRNA by using one or more reporter gene constructs comprising a constitutive promoter, such as a cytomegalovirus (CMV) or phosphoglycerate kinase (PGK) promoter, operably fused to, and capable of altering the expression of one or more reporter genes, such as a luciferase, chloramphenicol (CAT), or β-galactosidase, which, in turn, is operably fused in-frame with a dsRNA (such as one having a length between about 15 base-pairs and about 40 base-pairs or from about 5 nucleotides to about 24 nucleotides, or about 25 nucleotides to about 40 nucleotides) that contains one or more target sequence, as provided herein.

Individual reporter gene expression constructs may be co-transfected with one or more dsRNA or analog thereof. The capacity of a given dsRNA to reduce the expression level of a target gene may be determined by comparing the measured reporter gene activity in cells transfected with or without a dsRNA molecule of interest.

Certain embodiments disclosed herein provide methods for selecting one or more modified dsRNA molecule(s) that employ the step of predicting the stability of a dsRNA duplex. In some embodiments, such a prediction is achieved by employing a theoretical melting curve wherein a higher theoretical melting curve indicates an increase in dsRNA duplex stability and a concomitant decrease in cytotoxic effects. Alternatively, stability of a dsRNA duplex may be determined empirically by measuring the hybridization of a single RNA analog strand as described herein to a complementary target gene within, for example, a polynucleotide array. The melting temperature (i.e., the $T_m$ value) for each modified RNA and complementary RNA immobilized on the array can be determined, and from this $T_m$ value, the relative stability of a substituted or modified RNA pairing with a complementary RNA molecule can be determined.

For example, for universal-binding nucleotide, Kawase et al. (*Nucleic Acids Res.* 14:7727, 1986) have described an analysis of the nucleotide-pairing properties of Di(inosine) to A, C, G, and T, which was achieved by measuring the hybridization of oligonucleotides (ODNs) with Di in various positions to complementary sets of ODNs made as an array. The relative strength of nucleotide-pairing is I-C>I-A>I-G≈I-T. Generally, Di containing duplexes showed lower $T_m$ values when compared to the corresponding WC nucleotide pair. The stabilization of Di by pairing was in order of Dc>Da>Dg>Dt>Du. From the thermodynamic values calculated using Van't Hoff plots according to a two state model, Kawase et al. conclude that the sequence of purine-pyrimidine is favored in double strand formation due to nucleotide stacking. For instance the duplex formation of XY=AT is a more favored formation than an XY=CG and TA. As a person of skill in the art would understand, although universal-binding nucleotides are used herein as an example of determining stability (i.e., the $T_m$ value), other nucleotide substitutions (e.g., 5-methyluridine for uridine) or further modifications (e.g., a ribose modification at the 2'-position) can also be evaluated by these or similar methods.

Within certain embodiments, methods disclosed herein comprise the steps of (a) designing or synthesizing a suitable dsRNA for RNAi gene silencing of one or more target gene, wherein the dsRNA comprises at least three strands and optionally at least one modification or substitution (such as a 5-methyluridine, LNA, 2'-methoxy, 2'-fluoro, phosphorothioate, or any combination thereof); and (b) contacting a cell expressing one or more target protein with the dsRNA, wherein the dsRNA is capable of specifically binding to one or more target mRNA or gene, thereby reducing expression of one or more target members.

Any of these methods of identifying dsRNA of interest can also be used to examine a dsRNA that decreases expression of one or more target gene by RNA interference, comprising a first strand that is complementary to a target mRNA, or any combination thereof, and a second and third strand that have non-overlapping complementarity to the first strand, wherein the first and at least one of the second or third strand form a double-stranded region of about 5 to about 13 base pairs; wherein at least one pyrimidine of the dsRNA comprises a pyrimidine nucleoside according to Formula I or II:

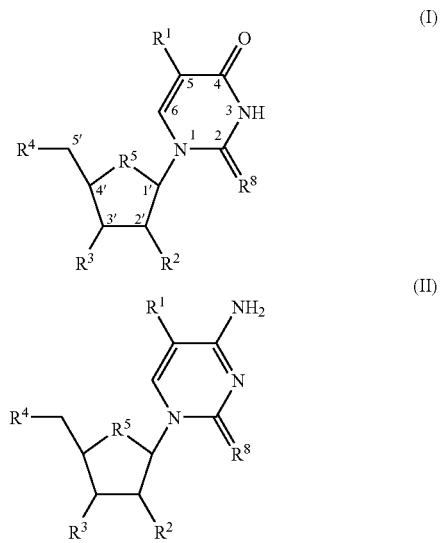

wherein $R^1$ and $R^2$ are each independently a —H, —OH, —OCH$_3$, —OCH$_2$OCH$_2$CH$_3$, —OCH$_2$CH$_2$OCH$_3$, halogen, substituted or unsubstituted C$_1$-C$_{10}$ alkyl, alkoxy, alkoxyalkyl, hydroxyalkyl, carboxyalkyl, alkylsulfonylamino, aminoalkyl, dialkylamino, alkylaminoalkyl, dialkylaminoalkyl, haloalkyl, trifluoromethyl, cycloalkyl, (cycloalkyl)alkyl, substituted or unsubstituted C$_2$-C$_{10}$ alkenyl, substituted or unsubstituted —O-allyl, —O—CH$_2$CH=CH$_2$, —O—CH=CHCH$_3$, substituted or unsubstituted C$_2$-C$_{10}$ alkynyl, carbamoyl, carbamyl, carboxy, carbonylamino, substituted or unsubstituted aryl, substituted or unsubstituted aralkyl, —NH$_2$, —NO$_2$, —C≡N, or heterocyclo group; $R^3$ and $R^4$ are each independently a hydroxyl, a protected hydroxyl, or an internucleoside linking group; and $R^5$ and $R^8$ are independently O or S. In certain embodiments, at least one nucleoside is according to Formula I in which $R^1$ is methyl and $R^2$ is —OH, or $R^1$ is methyl, $R^2$ is —OH, and $R^8$ is S. In other embodiments, the internucleoside linking group covalently links from about 5 to about 40 nucleosides.

Compositions and Methods of Use

As set forth herein, dsRNA of the instant disclosure are designed to target one or more target gene (including one or more mRNA splice variants thereof) that is expressed at an elevated level or continues to be expressed when it should not, and is a causal or contributing factor associated with, for example, a hyperproliferative, angiogenic, or inflammatory disease, state, or adverse condition. In this context, a dsRNA or analog thereof of this disclosure will effectively down regulate expression of one or more target gene to levels that prevent, alleviate, or reduce the severity or recurrence of one or more associated disease symptoms. Alternatively, for various distinct disease models in which expression of one or more target gene is not necessarily elevated as a consequence or sequel of disease or other adverse condition, down regulation of one or more target gene will nonetheless result in a therapeutic result by lowering gene expression. Furthermore, dsRNAs of this disclosure may be targeted to reduce expression of one or more target gene, which can result in upregulation of a "downstream" gene whose expression is negatively regulated, directly or indirectly, by one or more target protein. The dsRNA molecules of the instant disclosure comprise useful reagents and can be used in methods for a variety of therapeutic, diagnostic, target validation, genomic discovery, genetic engineering, and pharmacogenomic applications.

In certain embodiments, aqueous suspensions contain dsRNA of this disclosure in admixture with suitable excipients, such as suspending agents or dispersing or wetting agents. Exemplary suspending agents include sodium carboxymethylcellulose, methylcellulose, hydropropyl-methylcellulose, sodium alginate, polyvinylpyrrolidone, gum tragacanth and gum acacia. Representative dispersing or wetting agents include naturally-occurring phosphatides (e.g., lecithin), condensation products of an alkylene oxide with fatty acids (e.g., polyoxyethylene stearate), condensation products of ethylene oxide with long chain aliphatic alcohols (e.g., heptadecaethyleneoxycetanol), condensation products of ethylene oxide with partial esters derived from fatty acids and hexitol (e.g., polyoxyethylene sorbitol monooleate), or condensation products of ethylene oxide with partial esters derived from fatty acids and hexitol anhydrides (e.g., polyethylene sorbitan monooleate). In certain embodiments, the aqueous suspensions can optionally contain one or more preservatives (e.g., ethyl or n-propyl-p-hydroxybenzoate), one or more coloring agents, one or more flavoring agents, or one or more sweetening agents (e.g., sucrose, saccharin). In additional embodiments, dispersible powders and granules suitable for preparation of an aqueous suspension by the addition of water provide dsRNA of this disclosure in admixture with a dispersing or wetting agent, suspending agent and optionally one or more preservative, coloring agent, flavoring agent, or sweetening agent.

The present disclosure includes dsRNA compositions prepared for storage or administration that include a pharmaceutically effective amount of a desired compound in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co., A. R. Gennaro edit., 21$^{st}$ Edition, 2005. In certain embodiments, pharmaceutical compositions of this disclosure can optionally include preservatives, antioxidants, stabilizers, dyes, flavoring agents, or any combination thereof. Exemplary preservatives include sodium benzoate, esters of p-hydroxybenzoic acid, and sorbic acid.

The dsRNA compositions of the instant disclosure can be effectively employed as pharmaceutically-acceptable formulations. Pharmaceutically-acceptable formulations prevent, alter the occurrence or severity of, or treat (alleviate one or more symptom(s) to a detectable or measurable extent) a disease state or other adverse condition in a subject. A pharmaceutically acceptable formulation includes salts of the above compounds, for example, acid addition salts, such as salts of hydrochloric acid, hydrobromic acid, acetic acid, or benzene sulfonic acid. A pharmaceutical composition or formulation refers to a composition or formulation in a form suitable for administration into a cell, or a subject such as a human (e.g., systemic administration). The formulations of the present disclosure, having an amount of dsRNA sufficient to treat or prevent a disorder associated with target gene expression are, for example, suitable for topical (e.g., creams, ointments, skin patches, eye drops, ear drops) application or administration. Other routes of administration include oral, parenteral, sublingual, bladder wash-out, vaginal, rectal, enteric, suppository, nasal, and inhalation. The term parenteral, as used herein, includes subcutaneous, intravenous, intramuscular, intraarterial, intraabdominal, intraperitoneal, intraarticular, intraocular or retrobulbar, intraaural, intrathecal, intracavitary, intracelial, intraspinal, intrapulmonary or transpulmonary, intrasynovial, and intraurethral injection or infusion techniques. The pharmaceutical compositions of the present disclosure are formulated to allow the dsRNA contained therein to be bioavailable upon administration to a subject.

In further embodiments, dsRNA of this disclosure can be formulated as oily suspensions or emulsions (e.g., oil-in-water) by suspending dsRNA in, for example, a vegetable oil (e.g., arachis oil, olive oil, sesame oil or coconut oil) or a mineral oil (e.g., liquid paraffin). Suitable emulsifying agents can be naturally-occurring gums (e.g., gum acacia or gum tragacanth), naturally-occurring phosphatides (e.g., soy bean, lecithin, esters or partial esters derived from fatty acids and hexitol), anhydrides (e.g., sorbitan monooleate), or condensation products of partial esters with ethylene oxide (e.g., polyoxyethylene sorbitan monooleate). In certain embodiments, the oily suspensions or emulsions can optionally contain a thickening agent, such as beeswax, hard paraffin or cetyl alcohol. In related embodiments, sweetening agents and flavoring agents can optionally be added to provide palatable oral preparations. In yet other embodiments, these compositions can be preserved by the optionally adding an anti-oxidant, such as ascorbic acid.

In further embodiments, dsRNA of this disclosure can be formulated as syrups and elixirs with sweetening agents (e.g., glycerol, propylene glycol, sorbitol, glucose or sucrose). Such formulations can also contain a demulcent, preservative, flavoring, coloring agent, or any combination thereof. In other embodiments, pharmaceutical compositions comprising dsRNA of this disclosure can be in the form of a sterile, injectable aqueous or oleaginous suspension. The sterile injectable preparation can also be a sterile, injectable solution or suspension in a non-toxic parenterally acceptable diluent or solvent (e.g., as a solution in 1,3-butanediol). Among the exemplary acceptable vehicles and solvents useful in the compositions of this disclosure is water, Ringer's solution, or isotonic sodium chloride solution. In addition, sterile, fixed oils may be employed as a solvent or suspending medium for the dsRNA of this disclosure. For this purpose, any bland fixed oil can be employed including synthetic mono- or diglycerides. In addition, fatty acids such as oleic acid find use in the preparation of parenteral formulations.

Within certain embodiments of this disclosure, pharmaceutical compositions and methods are provided that feature the presence or administration of one or more dsRNA or analogs thereof of this disclosure, combined, complexed, or conjugated with a polypeptide, optionally formulated with a pharmaceutically-acceptable carrier, such as a diluent, stabilizer, buffer, or the like. The negatively charged dsRNA molecules of this disclosure may be administered to a patient by any standard means, with or without stabilizers, buffers, or the like, to form a composition suitable for treatment. When it is desired to use a liposome delivery mechanism, standard protocols for formation of liposomes can be followed. The compositions of the present disclosure may also be formulated and used as a tablet, capsule or elixir for oral administration, suppository for rectal administration, sterile solution, or suspension for injectable administration, either with or without other compounds known in the art. Thus, dsRNAs of the present disclosure may be administered in any form, such as nasally, transdermally, parenterally, or by local injection.

In accordance with this disclosure herein, dsRNA molecules (optionally substituted or modified or conjugated), compositions thereof, and methods for inhibiting expression of one or more target gene in a cell or organism are provided. In certain embodiments, this disclosure provides methods and dsRNA compositions for treating a subject, including a human cell, tissue or individual, having a disease or at risk of developing a disease caused by or associated with the expression of one or more target gene. In one embodiment, the method includes administering a dsRNA of this disclosure or a pharmaceutical composition containing the dsRNA to a cell or an organism, such as a mammal, such that expression of the target gene is silenced. Subjects (e.g., mammalian, human) amendable for treatment using the dsRNA molecules (optionally substituted or modified or conjugated), compositions thereof, and methods of the present disclosure include those suffering from one or more disease or condition mediated, at least in part, by overexpression or inappropriate expression of one or more target gene, or which are amenable to treatment by reducing expression of one or more target protein, including a hyperproliferative (e.g., cancer), angiogenic, metabolic, or inflammatory (e.g., arthritis) disease or disorder or condition.

Compositions and methods disclosed herein are useful in the treatment of a wide variety of target viruses, including retrovirus, such as human immunodeficiency virus (HIV), Hepatitis C Virus, Hepatitis B Virus, Coronavirus, as well as respiratory viruses (including human Respiratory Syncytial Virus, human Metapneumovirus, human Parainfluenza virus Rhinovirus and Influenza virus.

In other examples, the compositions and methods of this disclosure are useful as therapeutic tools to regulate expression of one or more target gene to treat or prevent symptoms of, for example, hyperproliferative disorders. Exemplary hyperproliferative disorders include neoplasms, carcinomas, sarcomas, tumors, or cancer. More exemplary hyperproliferative disorders include oral cancer, throat cancer, laryngeal cancer, esophageal cancer, pharyngeal cancer, nasopharyngeal cancer, oropharyngeal cancer, gastrointestinal tract cancer, gastrointestinal stromal tumors (GIST), small intestine cancer, colon cancer, rectal cancer, colorectal cancer, anal cancer, pancreatic cancer, breast cancer, cervical cancer, uterine cancer, vulvar cancer, vaginal cancer, urinary tract cancer, bladder cancer, kidney cancer, adrenocortical cancer, islet cell carcinoma, gallbladder cancer, stomach cancer, prostate cancer, ovarian cancer, endometrial cancer, trophoblastic tumor, testicular cancer, penial cancer, bone cancer, osteosarcoma, liver cancer, extrahepatic bile duct cancer, skin cancer, basal cell carcinoma (BCC), lung cancer, small cell lung cancer, non-small cell lung cancer (NSCLC), brain cancer, melanoma, Kaposi's sarcoma, eye cancer, head and neck cancer, squamous cell carcinoma of head and neck, tymoma, thymic carcinoma, thyroid cancer, parathyroid cancer, Hippel-Lindau syndrome, leukemia, acute myeloid leukemia, chronic myelogenous leukemia, acute lymphoblastic leukemia, hairy cell leukemia, lymphoma, non-Hodgkin's lymphoma, Burkitt's lymphoma, T-cell lymphoma, multiple myeloma, malignant pleural mesothelioma, Barrett's adenocarcinoma, Wilm's tumor, or the like.

In other examples, the compositions and methods of this disclosure are useful as therapeutic tools to regulate expression of one or more target gene to treat or prevent symptoms of, for example, inflammatory disorders. Exemplary inflammatory disorders include diabetes mellitus, rheumatoid arthritis, pannus growth in inflamed synovial lining, collagen-induced arthritis, spondylarthritis, ankylosing spondylitis, multiple sclerosis, encephalomyelitis, inflammatory bowel disease, Chron's disease, psoriasis or psoriatic arthritis, myasthenia gravis, systemic lupus erythematosis, graft-versus-host disease, atherosclerosis, and allergies.

Other exemplary disorders that can be treated with dsRNA of the instant disclosure include metabolic disorders, cardiac disease, pulmonary disease, neovascularization, ischemic disorders, age-related macular degeneration, diabetic retinopathy, glomerulonephritis, diabetes, asthma, chronic obstructive pulmonary disease, chronic bronchitis, lymphangiogenesis, and atherosclerosis.

In any of the methods disclosed herein, there may be used one or more dsRNA, or substituted or modified dsRNA as described herein, which comprises a first strand that is complementary to a target mRNA and is fully complementary, with up to three mismatches, to at least one other human target family mRNA, or vice-versa, and a second strand and a third strand that is each complementary to non-overlapping regions of the first strand, wherein the second strand and third strands can anneal with the first strand to form at least two double-stranded regions separated by a gap of up to 10 nucleotides, and wherein at least one double-stranded region is from about 5 base pairs up to 13 base pairs. In other embodiments, subjects can be effectively treated, prophylactically or therapeutically, by administering an effective amount of one or more dsRNA having a first strand that is complementary to a target mRNA and is fully complementary, with up to three mismatches, to at least one other target family mRNA, or vice-versa, and a second strand and a third strand that is each complementary to non-overlapping regions of the first strand, wherein the second strand and third strands can anneal with the first strand to form at least two double-stranded regions separated by a gap of up to 10 nucleotides, and wherein at least one double-stranded region is from about 5 base pairs up to 13 base pairs and at least one pyrimidine of the mdRNA is substituted with a pyrimidine nucleoside according to Formula I or II:

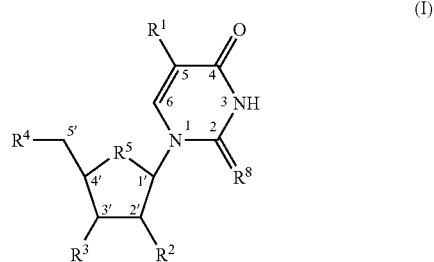

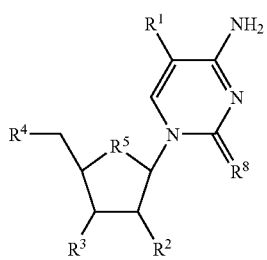

(II)

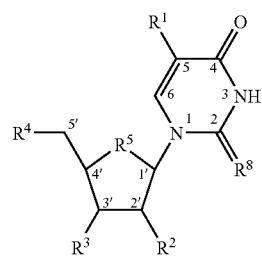

(I)

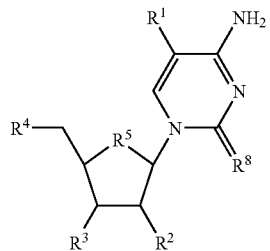

(II)

wherein R¹ and R² are each independently a —H, —OH, —OCH₃, —OCH₂OCH₂CH₃, —OCH₂CH₂OCH₃, halogen, substituted or unsubstituted $C_1$-$C_{10}$ alkyl, alkoxy, alkoxyalkyl, hydroxyalkyl, carboxyalkyl, alkylsulfonylamino, aminoalkyl, dialkylamino, alkylaminoalkyl, dialkylaminoalkyl, haloalkyl, trifluoromethyl, cycloalkyl, (cycloalkyl)alkyl, substituted or unsubstituted $C_2$-$C_{10}$ alkenyl, substituted or unsubstituted —O-allyl, —O—CH₂CH═CH₂, —O—CH═CHCH₃, substituted or unsubstituted $C_2$-$C_{10}$ alkynyl, carbamoyl, carbamyl, carboxy, carbonylamino, substituted or unsubstituted aryl, substituted or unsubstituted aralkyl, —NH₂, —NO₂, —C≡N, or heterocyclo group; R³ and R⁴ are each independently a hydroxyl, a protected hydroxyl, or an internucleoside linking group; and R⁵ and R⁸ are independently O or S. In certain embodiments, at least one nucleoside is according to Formula I in which R¹ is methyl and R² is —OH, or R¹ is methyl, R² is —OH, and R⁸ is S. In other embodiments, the internucleoside linking group covalently links from about 5 to about 40 nucleosides.

In further embodiments, subjects can be effectively treated, prophylactically or therapeutically, by administering an effective amount of one or more dsRNA, or substituted or modified dsRNA as described herein, having a first strand that is complementary to a target mRNA and is fully complementary, with up to three mismatches, to at least one other target gene mRNA, or vice-versa, and a second strand and a third strand that is each complementary to non-overlapping regions of the first strand, wherein the second strand and third strands can anneal with the first strand to form at least two double-stranded regions separated by a gap of up to 10 nucleotides, and wherein the combined double-stranded regions total about 15 base pairs to about 40 base pairs and the mdRNA molecule comprises blunt ends. In still further embodiments, methods disclosed herein there may be used with one or more dsRNA that comprises a first strand that is complementary to a target gene mRNA and is fully complementary, with up to three mismatches, to at least one other target family mRNA, or vice-versa, and a second strand and a third strand that is each complementary to non-overlapping regions of the first strand, wherein the second strand and third strands can anneal with the first strand to form at least two double-stranded regions separated by a gap of up to 10 nucleotides, and wherein at least one double-stranded region is from about 5 base pairs up to 13 base pairs, the mdRNA molecule comprises blunt ends, and at least one pyrimidine of the mdRNA is substituted with a pyrimidine nucleoside according to Formula I or II:

wherein R¹ and R² are each independently a —H, —OH, —OCH₃, —OCH₂OCH₂CH₃, —OCH₂CH₂OCH₃, halogen, substituted or unsubstituted $C_1$-$C_{10}$ alkyl, alkoxy, alkoxyalkyl, hydroxyalkyl, carboxyalkyl, alkylsulfonylamino, aminoalkyl, dialkylamino, alkylaminoalkyl, dialkylaminoalkyl, haloalkyl, trifluoromethyl, cycloalkyl, (cycloalkyl)alkyl, substituted or unsubstituted $C_2$-$C_{10}$ alkenyl, substituted or unsubstituted —O-allyl, —O—CH₂CH═CH₂, —O—CH═CHCH₃, substituted or unsubstituted $C_2$-$C_{10}$ alkynyl, carbamoyl, carbamyl, carboxy, carbonylamino, substituted or unsubstituted aryl, substituted or unsubstituted aralkyl, —NH₂, —NO₂, —C≡N, or heterocyclo group; R³ and R⁴ are each independently a hydroxyl, a protected hydroxyl, or an internucleoside linking group; and R⁵ and R⁸ are independently O or S. In certain embodiments, at least one nucleoside is according to Formula I in which R¹ is methyl and R² is —OH, or R¹ is methyl, R² is —OH, and R⁸ is S. In other embodiments, the internucleoside linking group covalently links from about 5 to about 40 nucleosides.

Within additional aspects of this disclosure, combination formulations and methods are provided comprising an effective amount of one or more dsRNA of the present disclosure in combination with one or more secondary or adjunctive active agents that are formulated together or administered coordinately with the dsRNA of this disclosure to control one or more target gene-associated disease or condition as described herein. Useful adjunctive therapeutic agents in these combinatorial formulations and coordinate treatment methods include, for example, enzymatic nucleic acid molecules, allosteric nucleic acid molecules, antisense, decoy, or aptamer nucleic acid molecules, antibodies such as monoclonal antibodies, small molecules and other organic or inorganic compounds including metals, salts and ions, and other drugs and active agents indicated for treating one or more target gene-associated disease or condition, including chemotherapeutic agents used to treat cancer, steroids, non-steroidal anti-inflammatory drugs (NSAIDs), or the like.

Exemplary chemotherapeutic agents include alkylating agents (e.g., cisplatin, oxaliplatin, carboplatin, busulfan, nitrosoureas, nitrogen mustards, uramustine, temozolomide), antimetabolites (e.g., aminopterin, methotrexate, mercaptopurine, fluorouracil, cytarabine), taxanes (e.g., paclitaxel, docetaxel), anthracyclines (e.g., doxorubicin, daunorubicin, epirubicin, idaruicin, mitoxantrone, valrubicin), bleomycin, mytomycin, actinomycin, hydroxyurea, topoisomerase inhibitors (e.g., camptothecin, topotecan, irinotecan, etoposide, teniposide), monoclonal antibodies (e.g., alemtuzumab, bevacizumab, cetuximab, gemtuzumab, panitumumab, rituximab, tositumomab, trastuzumab), vinca alkaloids (e.g., vincristine, vinblastine, vindesine, vinorelbine), cyclophosphamide, prednisone, leucovorin, oxaliplatin.

To practice the coordinate administration methods of this disclosure, a dsRNA is administered simultaneously or sequentially in a coordinated treatment protocol with one or more secondary or adjunctive therapeutic agents described herein or known in the art. The coordinate administration may be done in either order, and there may be a time period while only one or both (or all) active therapeutic agents, individually or collectively, exert their biological activities. A distinguishing aspect of all such coordinate treatment methods is that the dsRNA present in a composition elicits some favorable clinical response, which may or may not be in conjunction with a secondary clinical response provided by the secondary therapeutic agent. For example, the coordinate administration of the dsRNA with a secondary therapeutic agent as contemplated herein can yield an enhanced (e.g., synergistic) therapeutic response beyond the therapeutic response elicited by either or both the purified dsRNA or secondary therapeutic agent alone.

In another embodiment, a dsRNA of this disclosure can include a conjugate member on one or more of the nucleotides of a dsRNA (e.g., terminal). The conjugate member can be, for example, a lipophile, a terpene, a protein binding agent, a vitamin, a carbohydrate, or a peptide. For example, the conjugate member can be naproxen, nitroindole (or another conjugate that contributes to stacking interactions), folate, ibuprofen, or a C5 pyrimidine linker. In other embodiments, the conjugate member is a glyceride lipid conjugate (e.g., a dialkyl glyceride derivatives), vitamin E conjugates, or thiocholesterols. Additional conjugate members include peptides that function, when conjugated to a modified dsRNA of this disclosure, to facilitates delivery of the dsRNA into a target cell, or otherwise enhance delivery, stability, or activity of the dsRNA when contacted with a biological sample. Exemplary peptide conjugate members for use within these aspects of this disclosure, include peptides PN27, PN28, PN29, PN58, PN61, PN73, PN158, PN159, PN173, PN182, PN202, PN204, PN250, PN361, PN365, PN404, PN453, and PN509 are described, for example, in U.S. Patent Application Publication Nos. 2006/0040882 and 2006/0014289, and U.S. Provisional Patent Application No. 60/939,578, which are all incorporated herein by reference. In certain embodiments, when peptide conjugate partners are used to enhance delivery of dsRNA or analogs thereof of this disclosure, the resulting dsRNA formulations and methods will often exhibit further reduction of an interferon response in target cells as compared to dsRNAs delivered in combination with alternate delivery vehicles, such as lipid delivery vehicles (e.g., Lipofectamine™).

In still another embodiment, a dsRNA or analog thereof of this disclosure may be conjugated to the polypeptide and admixed with one or more non-cationic lipids or a combination of a non-cationic lipid and a cationic lipid to form a composition that enhances intracellular delivery of the dsRNA as compared to delivery resulting from contacting the target cells with a naked dsRNA. In more detailed aspects of this disclosure, the mixture, complex or conjugate comprising a dsRNA and a polypeptide can be optionally combined with (e.g., admixed or complexed with) a cationic lipid, such as Lipofectine™. To produce these compositions comprised of a polypeptide, dsRNA and a cationic lipid, the dsRNA and peptide may be mixed together first in a suitable medium such as a cell culture medium, after which the cationic lipid is added to the mixture to form a dsRNA/delivery peptide/cationic lipid composition. Optionally, the peptide and cationic lipid can be mixed together first in a suitable medium such as a cell culture medium, followed by the addition of the dsRNA to form the dsRNA/delivery peptide/cationic lipid composition.

This disclosure also features the use of dsRNA compositions comprising surface-modified liposomes containing poly(ethylene glycol) lipids (PEG-modified, or long-circulating liposomes or stealth liposomes). These formulations offer a method for increasing the accumulation of drugs in target tissues (Lasic et al., Chem. Rev. 95:2601, 1995; Ishiwata et al., Chem. Pharm. Bull. 43:1005, 1995). Such liposomes have been shown to accumulate selectively in tumors, presumably by extravasation and capture in the neovascularized target tissues (Lasic et al., Science 267:1275, 1995; Oku et al., Biochim. Biophys. Acta 1238:86, 1995). The long-circulating liposomes enhance the pharmacokinetics and pharmacodynamics of nucleic acid molecules as compared to conventional cationic liposomes, which are known to accumulate in tissues of the mononuclear phagocytic system (MPS) (Liu et al., J. Biol. Chem. 42:24864, 1995; Choi et al., PCT Publication No. WO 96/10391; Ansell et al., PCT Publication No. WO 96/10390; Holland et al., PCT Publication No. WO 96/10392). Long-circulating liposomes may also provide additional protection from nuclease degradation as compared to cationic liposomes in theory due to avoiding accumulation in metabolically aggressive MPS tissues, such as the liver and spleen.

In one embodiment, this disclosure provides compositions suitable for administering dsRNA molecules of this disclosure to specific cell types, such as hepatocytes. For example, the asialoglycoprotein receptor (ASGPr) (Wu and Wu, J. Biol. Chem. 262:4429, 1987) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (Baenziger and Fiete, Cell 22: 611, 1980; Connolly et al., J. Biol. Chem. 257:939, 1982). Lee and Lee (Glycoconjugate J. 4:317, 1987) obtained this high specificity through the use of N-acetyl-D-galactosamine as the carbohydrate moiety, which has higher affinity for the receptor compared to galactose. This "clustering effect" has also been described for the binding and uptake of mannosyl-terminating glycoproteins or glycoconjugates (Ponpipom et al., J. Med. Chem. 24:1388, 1981). The use of galactose and galactosamine based conjugates to transport exogenous compounds across cell membranes can provide a targeted delivery approach to the treatment of liver disease. The use of bioconjugates can also provide a reduction in the required dose of therapeutic compounds required for treatment. Furthermore, therapeutic bioavailability, pharmacodynamics, and pharmacokinetic parameters can be modulated through the use of dsRNA bioconjugates of this disclosure.

The present disclosure also features a method for preparing dsRNA nanoparticles. A first solution containing melamine derivatives is dissolved in an organic solvent such as dimethyl sulfoxide, or dimethyl formamide to which an acid such as HCl has been added. The concentration of HCl would be about 3.3 moles of HCl for every mole of the melamine derivative. The first solution is then mixed with a second solution, which includes a nucleic acid dissolved or suspended in a polar or hydrophilic solvent (e.g., an aqueous buffer solution containing, for instance, ethylenediaminetraacetic acid (EDTA), or tris(hydroxymethyl)aminomethane (TRIS), or combinations thereof. The mixture forms a first emulsion. The mixing can be done using any standard technique such as, for example, sonication, vortexing, or in a microfluidizer. This causes complexing of the nucleic acids with the melamine derivative forming a trimeric nucleic acid complex. While not being bound to theory or mechanism, it is believed that three nucleic acids are complexed in a circular fashion about one melamine derivative moiety, and that a number of the melamine derivative moieties can be complexed with the three nucleic acid molecules depending on the size of the number of nucleotides that the nucleic acid has. The concentration should be from about 1 to about 7 moles of the melamine derivative for every mole of a double-stranded nucleic acid having about 20 nucleotide pairs, more if the double-stranded nucleic acid is larger. The resultant nucleic acid particles can be purified and the organic solvent removed using size-exclusion chromatography or dialysis or both.

The complexed nucleic acid nanoparticles can then be mixed with an aqueous solution containing either polyarginine or a Gln-Asn polymer, or both, in an aqueous solution. A preferred molecular weight of each polymer is about 5000 to about 15,000 Daltons. This forms a solution containing nanoparticles of nucleic acid complexed with the melamine derivative and the polyarginine and the Gln-Asn polymers. The mixing steps are carried out in a manner that minimizes shearing of the nucleic acid while producing nanoparticles on average smaller than about 200 nanometers in diameter. While not wishing to be bound by theory, it is believed that the polyarginine complexes with the negative charge of the phosphate groups within the minor groove of the nucleic acid, and the polyarginine wraps around the trimeric nucleic acid complex. At either terminus of the polyarginine other moieties, such as the TAT polypeptide, mannose or galactose, can be covalently bound to the polymer to direct binding of the nucleic acid complex to specific tissues, such as to the liver when galactose is used. While not being bound to theory, it is believed that the Gln-Asn polymer complexes with the nucleic acid complex within the major groove of the nucleic acid through hydrogen bonding with the bases of the nucleic acid. The polyarginine and the Gln-Asn polymer should be present at a concentration of 2 moles per every mole of nucleic acid having 20 base pairs. The concentration should be increased proportionally for a nucleic acid having more than 20 base pairs. For example, if the nucleic acid has 25 base pairs, the concentration of the polymers should be 2.5-3 moles per mole of double-stranded nucleic acid. An example of is a polypeptide operatively linked to an N-terminal protein transduction domain from HIV TAT. The HIV TAT construct for use in such a protein is described in detail in Vocero-Akbani et al., *Nature Med.* 5:23, 1999. See also, U.S. Patent Application Publication No. 2004/0132161, published on Jul. 8, 2004. The resultant nanoparticles can be purified by standard means such as size exclusion chromatography followed by dialysis. The purified complexed nanoparticles can then be lyophilized using techniques well known in the art.

One embodiment of the present disclosure provides nanoparticles less than 100 nanometers (nm) comprising dsRNA that decreases expression of one or more target gene by RNAi. More specifically, the dsRNA is less than about 30 base pairs in length, or is from about 20 to about 25 base pairs in length.

A pharmaceutically effective dose is that dose required to prevent, inhibit the occurrence, or treat (alleviate a symptom to some extent, preferably all of the symptoms) a disease state. The pharmaceutically effective dose depends on the type of disease, the composition used, the route of administration, the type of subject being treated, the physical characteristics of the specific subject under consideration for treatment, concurrent medication, and other factors that those skilled in the medical arts will recognize. For example, an amount between 0.1 mg/kg and 100 mg/kg body weight/day of active ingredients may be administered depending on the potency of a dsRNA of this disclosure.

Dosage levels in the order of about 0.1 mg to about 140 mg per kilogram of body weight per day can be useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy. Following administration of dsRNA according to the formulations and methods of this disclosure, test subjects will exhibit about a 10% up to about a 99% reduction in one or more symptoms associated with the disease or disorder being treated, as compared to placebo-treated or other suitable control subjects.

Nucleic acid molecules and polypeptides can be administered to cells by a variety of methods known to those of skill in the art, including administration within formulations that comprise the dsRNA and polypeptide alone, or that further comprise one or more additional components, such as a pharmaceutically acceptable carrier, diluent, excipient, adjuvant, emulsifier, buffer, stabilizer, preservative, or the like. In certain embodiments, the dsRNA or the polypeptide can be encapsulated in liposomes, administered by iontophoresis, or incorporated into other vehicles, such as hydrogels, cyclodextrins, biodegradable nanocapsules, bioadhesive microspheres, or proteinaceous vectors (see, e.g., PCT Publication No. WO 00/53722). Alternatively, a nucleic acid/peptide/vehicle combination can be locally delivered by direct injection or by use of an infusion pump. Direct injection of the nucleic acid molecules of this disclosure, whether subcutaneous, intramuscular, or intradermal, can take place using standard needle and syringe methodologies, or by needle-free technologies, such as those described in Conroy et al., *Clin. Cancer Res.* 5:2330, 1999, and PCT Publication No. WO 99/31262.

The dsRNAs can also be administered in the form of suppositories, for example, for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

Further methods for delivery of nucleic acid molecules, such as the dsRNAs of this disclosure, are described, for example, in Boado et al., *J. Pharm. Sci.* 87:1308, 1998; Tyler et al., *FEBS Lett.* 421:280, 1999; Pardridge et al., *Proc. Nat'l Acad. Sci. USA* 92:5592, 1995; Boado, *Adv. Drug Delivery Rev.* 15:73, 1995; Aldrian-Herrada et al., *Nucleic Acids Res.* 26:4910, 1998; Tyler et al., *Proc. Nat'l Acad. Sci. USA* 96:7053, 1999; Akhtar et al., *Trends Cell Bio.* 2:139, 1992; "Delivery Strategies for Antisense Oligonucleotide Therapeutics," ed. Akhtar, 1995, Maurer et al., *Mol. Membr. Biol.* 16:129, 1999; Hofland and Huang, *Handb. Exp. Pharmacol.* 137:165, 1999; and Lee et al., *ACS Symp. Ser.* 752:184, 2000. Sullivan et al. (PCT Publication No. WO 94/02595) further describe general methods for delivery of enzymatic nucleic acid molecules, which methods can be used to supplement or complement delivery of dsRNA contemplated within this disclosure.

In addition to in vivo gene inhibition, a skilled artisan will appreciate that the dsRNAs of the present disclosure are useful in a wide variety of in vitro applications, such as in scientific and commercial research (e.g., elucidation of physiological pathways, drug discovery and development), and medical and veterinary diagnostics. In general, the method involves the introduction of the dsRNA agent into a cell using known techniques (e.g., absorption through cellular processes, or by auxiliary agents or devices, such as electroporation, lipofection, or through the use of peptide conjugates), then maintaining the cell for a time sufficient to obtain degradation of one or more target mRNA.

All U.S. patents, U.S. patent application publications, U.S. patent applications, foreign patents, foreign patent applications, non-patent publications, figures, and websites referred to in this specification are expressly incorporated herein by reference, in their entirety.

EXAMPLES

Example 1

Knockdown of β-Galactosidase Activity by Gapped dsRNA Dicer Substrate

The activity of a Dicer substrate dsRNA containing a gap in the double-stranded structure in silencing LacZ mRNA as compared to the normal Dicer substrate dsRNA (i.e., not having a gap) was examined.
Nucleotide Sequences of dsRNA and mdRNA Targeting LacZ mRNA The nucleic acid sequence of the one or more sense strands, and the antisense strand of the dsRNA and gapped dsRNA (also referred to herein as a meroduplex or mdRNA) are shown below and were synthesized using standard techniques. The RISC activator LacZ dsRNA comprises a 21 nucleotide sense strand and a 21 nucleotide antisense strand, which can anneal to form a double-stranded region of 19 base pairs with a two deoxythymidine overhang on each strand (referred to as 21/21 dsRNA).
LacZ dsRNA (21/21)—RISC Activator

```
                                      (SEQ ID NO: 1)
Sense       5'-CUACACAAAUCAGCGAUUUdTdT-3'

(SEQ ID NO: 2)
Antisense   3'-dTdTGAUGUGUUUAGUCGCUAAA-5'
```

The Dicer substrate LacZ dsRNA comprises a 25 nucleotide sense strand and a 27 nucleotide antisense strand, which can anneal to form a double-stranded region of 25 base pairs with one blunt end and a cytidine and uridine overhang on the other end (referred to as 25/27 dsRNA).
LacZ dsRNA (25/27)—Dicer Substrate

```
                                      (SEQ ID NO: 3)
Sense       5'-CUACACAAAUCAGCGAUUUCCAUdGdT-3'

(SEQ ID NO: 4)
Antisense   3'-CUGAUGUGUUUAGUCGCUAAAGGUA C A-5'
```

The LacZ mdRNA comprises two sense strands of 13 nucleotides (5'-portion) and 11 nucleotides (3'-portion) and a 27 nucleotide antisense strand, which three strands can anneal to form two double-stranded regions of 13 and 11 base pairs separated by a single nucleotide gap (referred to as a 13, 11/27 mdRNA). The 5'-end of the 11 nucleotide sense strand fragment may be optionally phosphorylated. The "*" indicates a gap—in this case, a single nucleotide gap (i.e., a cytidine is missing).
LacZ mdRNA (13, 11/27)—Dicer Substrate

```
                                      (SEQ ID NOS: 5, 6)
Sense       5'-CUACACAAAUCAG*GAUUUCCAUdGdT-3'

(SEQ ID NO: 4)
Antisense   3'-CUGAUGUGUUUAGUCGCUAAAGGUA C A-5'
```

Each of the LacZ dsRNA or mdRNA was used to transfect 9lacZ/R cells.
Transfection Six well collagen-coated plates were seeded with 5×10⁵ 9lacZ/R cells/well in a 2 ml volume per well, and incubated overnight at 37° C./5% CO$_2$ in DMEM/high glucose media. Preparation for transfection: 250 μl of OPTIMEM media without serum was mixed with 5 μl of 20 pmol/μl dsRNA and 5 μl of HIPERFECT transfection solution (Qiagen) was mixed with another 250 μl OPTIMEM media. After both mixtures were allowed to equilibrate for 5 minutes, the RNA and transfection solutions were combined and left at room temperature for 20 minutes to form transfection complexes. The final concentration of HIPERFECT was 50 μM, and the dsRNAs were tested at 0.05 nM, 0.1 nM, 0.2 nM, 0.5 nM, 1 nM, 2 nM, 5 nM, and 10 nM, while the mdRNA was tested at 0.2 nM, 0.5 nM, 1 nM, 2 nM, 5 nM, 10 nM, 20 nM, and 50 nM. Complete media was removed, the cells were washed with incomplete OPTIMEM, and then 500 transfection mixture was applied to the cells, which were incubated with gentle shaking at 37° C. for 4 hours. After transfecting, the transfection media was removed, cells were washed once with complete DMEM/high glucose media, fresh media added, and the cells were then incubated for 48 hours at 37° C., 5% CO$_2$.
β-Galactosidase Assay Transfected cells were washed with PBS, and then detached with 0.5 ml trypsin/EDTA. The detached cells were suspended in 1 ml complete DMEM/high glucose and transferred to a clean tube. The cells were harvested by centrifugation at 250×g for 5 minutes, and then resuspended in 50 μl 1× lysis buffer at 4° C. The lysed cells were subjected to two freeze-thaw cycles on dry ice and a 37° C. water bath. The lysed samples were centrifuged for 5 minutes at 4° C. and the supernatant was recovered. For each sample, 1.5 μl and 10 μl of lysate was transferred to a clean tube and sterile water added to a final volume of 30 μl followed by the addition of 70 μl o-nitrophenyl-β-D-galactopyranose (ONPG) and 200 μl 1× cleavage buffer with β-mercaptoethanol. The samples were mixed briefly, incubated for 30 minutes at 37° C., and then 500 μl stop buffer was added (final volume 800 μl). β-Galactosidase activity for each sample was measured in disposable cuvettes at 420 nm. Protein concentration was determined by the BCA (bicinchoninic acid) method. For the purpose of the instant example, the level of measured LacZ activity was correlated with the quantity of LacZ transcript within 9L/LacZ cells. Thus, a reduction in β-galactosidase activity after dsRNA transfection, absent a negative impact on cell viability, was attributed to a reduction in the quantity of LacZ transcripts resulting from targeted degradation mediated by the LacZ dsRNA.

Results

Knockdown activity in transfected and untransfected cells was normalized to a Qneg control dsRNA and presented as a normalized value of the Qneg control (i.e., Qneg represented 100% or "normal" gene expression levels). Both the lacZ RISC activator and Dicer substrate dsRNAs molecule showed good knockdown of β-galactosidase activity at concentration as low as 0.1 nM (FIG. 1), while the Dicer substrate antisense strand alone (single stranded 27mer) had no silencing effect. Surprisingly, a gapped mdRNA showed good knockdown although somewhat lower than that of intact RISC activator and Dicer substrate dsRNAs (FIG. 1). The presence of the gapmer cytidine (i.e., the missing nucleotide) at various concentrations (0.1 μM to 50 μM) had no effect on the activity of the mdRNA (data not shown). None of the dsRNA or mdRNA solutions showed any detectable toxicity in the transfected 9L/LacZ cells. The $IC_{50}$ of the lacZ mdRNA was calculated to be 3.74 nM, which is about 10 fold lower than what had been previously measured for lacZ dsRNA 21/21 (data not shown). These results show that a meroduplex (gapped dsRNA) is capable of inducing gene silencing.

Example 2

Knockdown of Influenza Gene Expression by Nicked dsRNA

The activity of a nicked dsRNA (21/21) in silencing influenza gene expression as compared to a normal dsRNA (i.e., not having a nick) was examined.

Nucleotide Sequences of dsRNA and mdRNA Targeting Influenza mRNA

The dsRNA and nicked dsRNA (another form of meroduplex, referred to herein as ndsRNA) are shown below and were synthesized using standard techniques. The RISC activator influenza G1498 dsRNA comprises a 21 nucleotide sense strand and a 21 nucleotide antisense strand, which can anneal to form a double-stranded region of 19 base pairs with a two deoxythymidine overhang on each strand.

G1498-wt dsRNA (21/21)

```
                                          (SEQ ID NO: 7)
Sense      5'-GGAUCUUAUUUCUUCGGAGdTdT-3'

(SEQ ID NO: 8)
Antisense  3'-dTdTCCUAGAAUAAAGAAGCCUC-5'
```

The RISC activator influenza G1498 dsRNA was nicked on the sense strand after nucleotide 11 to produce a ndsRNA having two sense strands of 11 nucleotides (5'-portion, italic) and 10 nucleotides (3'-portion) and a 21 nucleotide antisense strand, which three strands can anneal to form two double-stranded regions of 11 (shown in italics) and 10 base pairs separated by a one nucleotide gap (which may be referred to as G1498 11, 10/21 ndsRNA-wt). The 5'-end of the 10 nucleotide sense strand fragment may be optionally phosphorylated, as depicted by a "p" preceding the nucleotide (e.g., pC).

G1498 ndsRNA-wt (11, 10/21)

```
                                       (SEQ ID NO: 9, 10)
Sense      5'-GGAUCUUAUUUCUUCGGAGdTdT-3'

(SEQ ID NO: 8)
Antisense  3'-dTdTCCUAGAAUAAAGAAGCCU C-5'
```

G1498 ndsRNA-wt (11, 10/21)

```
                                     (SEQ ID NOS: 9, 10)
Sense      5'-GGAUCUUAUUUpCUUCGGAGdTdT-3'

(SEQ ID NO: 8)
Antisense  3'-dTdTCCUAGAAUAAAGAAGCCUC-5'
```

In addition, each of these G1498 dsRNAs were made with each U substituted with a 5-methyluridine (ribothymidine) and are referred to as G1498 dsRNA-rT. Each of the G1498 dsRNA or ndsRNA (meroduplex), with or without the 5-methyluridine substitution, was used to transfect HeLa S3 cells having an influenza target sequence associated with a luciferase gene. Also, the G1498 antisense strand alone or the antisense strand annealed to the 11 nucleotide sense strand portion alone or the 10 nucleotide sense strand portion alone were examined for activity.

Transfection and Dual Luciferase Assay

The reporter plasmid psiCHECK™-2 (Promega, Madison, Wis.), which constitutively expresses both firefly luc2 (*Photinus pyralis*) and *Renilla* (*Renilla reniformis*, also known as sea pansy) luciferases, was used to clone in a portion of the influenza NP gene downstream of the *Renilla* translational stop codon that results in a *Renilla*-influenza NP fusion mRNA. The firefly luciferase in the psiCHECK™-2 vector is used to normalize *Renilla* luciferase expression and serves as a control for transfection efficiency.

Multi-well plates were seeded with HeLa S3 cells/well in 100 μl Ham's F12 medium and 10% fetal bovine serum, and incubated overnight at 37° C./5% $CO_2$. Using essentially the same transfection procedure as described in Example 1, the HeLa S3 cells were transfected with the psiCHECK™-influenza plasmid (75 ng) and G1498 dsRNA or ndsRNA (final concentration of 10 nM or 100 nM) formulated in Lipofectamine™ 2000 and OPTIMEM reduced serum medium. The transfection mixture was incubated with the HeLa S3 cells with gentle shaking at 37° C. for about 18 to 20 hours.

After transfecting, firefly luciferase reporter activity was measured first by adding Dual-Glo™ Luciferase Reagent (Promega, Madison, Wis.) for 10 minutes with shaking, and then quantitating the luminescent signal using a VICTOR³™ 1420 Multilabel Counter (PerkinElmer, Waltham, Mass.). After measuring the firefly luminescence, Stop & Glo® Reagent (Promega, Madison, Wis.) was added for 10 minutes with shaking to simultaneously quench the firefly reaction and initiate the *Renilla* luciferase reaction, and then the *Renilla* luciferase luminescent signal was quantitated VICTOR³™ 1420 Multilabel Counter (PerkinElmer, Waltham, Mass.).

Results

Figure 2:
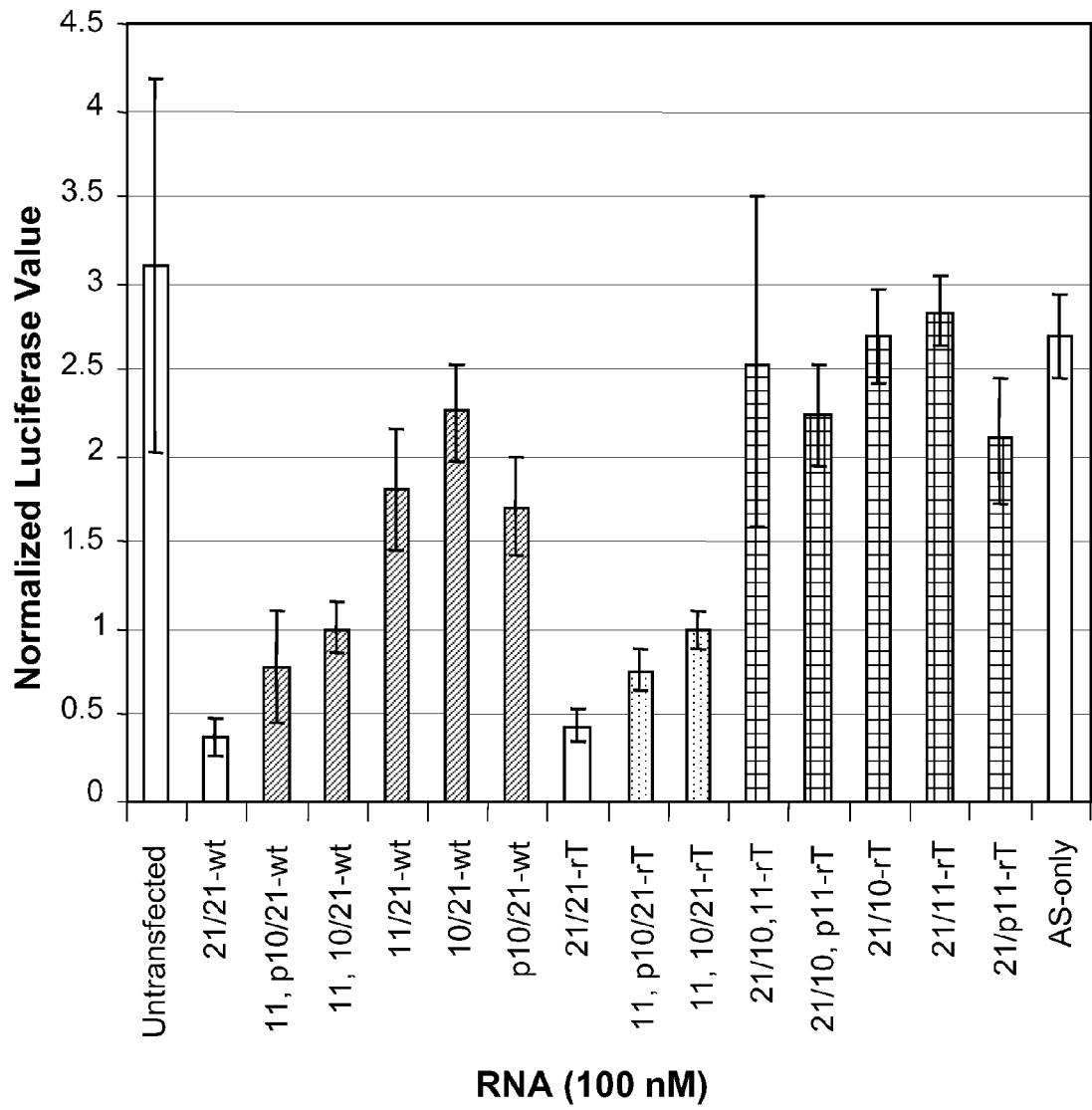
FIG. 2 shows knockdown activity of a RISC activator influenza dsRNA G1498 (21/21) and nicked dsRNA (10, 11/21) at 100 nM. The "wt" designation indicates an unsubstituted RNA molecule; "rT" indicates RNA having each uridine substituted with a ribothymidine; and "p" indicates that the 5'-nucleotide of that strand was phosphorylated. The 21 nucleotide sense and antisense strands of G1498 were individually nicked between the nucleotides 10 and 11 as measured from the 5'-end, and is referred to as 11, 10/21 and 21/10, 11, respectively. The G1498 single stranded 21 nucleotide antisense strand alone (designated AS-only) was used as a control.

Knockdown activity in transfected and untransfected cells was normalized to a Qneg control dsRNA and presented as a normalized value of the Qneg control (i.e., Qneg represented 100% or "normal" gene expression levels). Thus, a smaller value indicates a greater knockdown effect. The G1498 dsRNA-wt and dsRNA-rT showed similar good knockdown at a 100 nM concentration (FIG. 2). Surprisingly, the G1498 ndsRNA-rT, whether phosphorylated or not, showed good knockdown although somewhat lower than the G1498 dsRNA-wt (FIG. 2). Similar results were obtained with dsRNA or ndsRNA at 10 nM (data not shown). None of the G1498 dsRNA or ndsRNA solutions showed any detectable toxicity in HeLa S3 cells at either 10 nM or 100 nM. Even the presence of only half a nicked sense strand (an 11 nucleotide or 10 nucleotide strand alone) with a G1498 antisense strand showed some detectable activity. These results show that a nicked-type meroduplex dsRNA molecule is unexpectedly capable of promoting gene silencing.

Example 3

Knockdown Activity of mdRNA Having a Nick in Different Positions

In this example, the activity of a dicer substrate LacZ dsRNA of Example 1 having a sense strand with a nick at various positions was examined. In addition, a dideoxy nucleotide (i.e., ddG) was incorporated at the 5'-end of the 3'-most strand of a sense sequence having a nick or a single nucleotide gap to determine whether the in vivo ligation of the nicked sense strand is "rescuing" activity. The ddG is not a substrate for ligation. Also examined was the influenza dicer substrate dsRNA of Example 6 having a sense strand with a nick at one of positions 8 to 14. The "p" designation indicates that the 5'-end of the 3'-most strand of the nicked sense influenza sequence was phosphorylated. The "L" designation indicates that the G at position 2 of the 5'-most strand of the nicked sense influenza sequence was substituted for a locked nucleic acid G. The Qneg is a negative control dsRNA.

Figure 3:
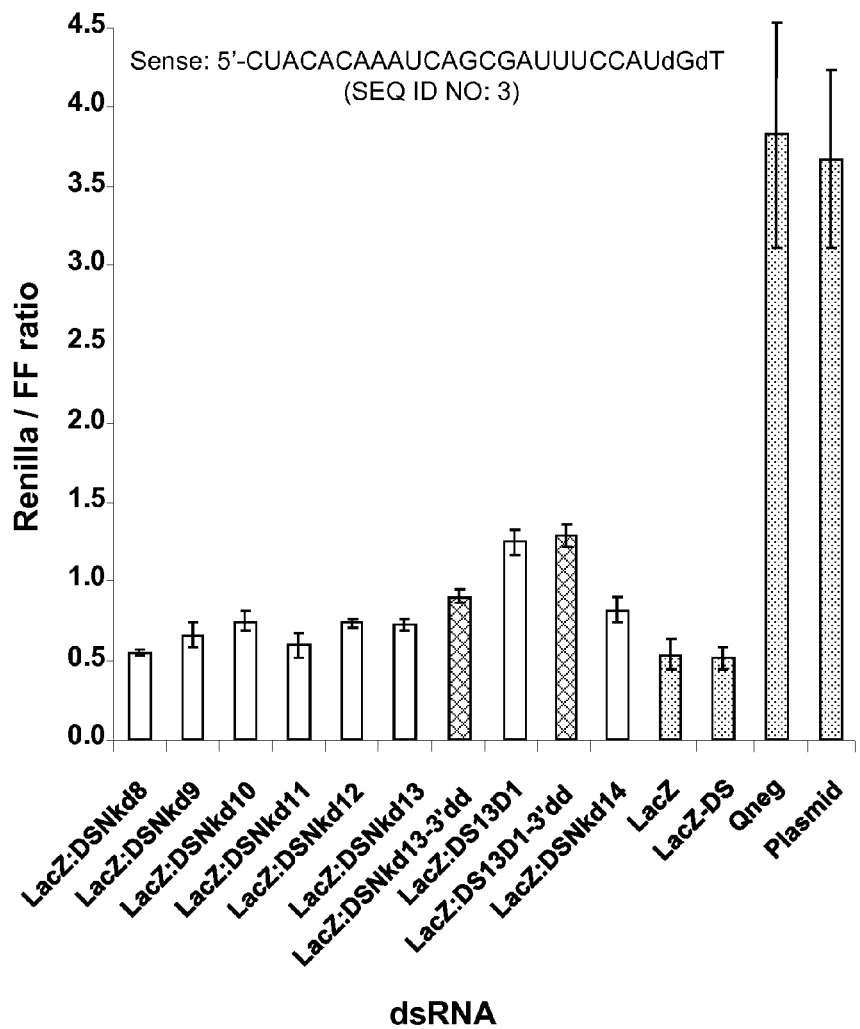
FIG. 3 shows knockdown activity of a lacZ dicer substrate (25/27) having a nick in one of each of positions 8 to 14 and a one nucleotide gap at position 13 of the sense strand (counted from the 5'-end). A dideoxy guanosine (ddG) was incorporated at the 5'-end of the 3'-most strand of the nicked or gapped sense sequence at position 13.
Figure 4:
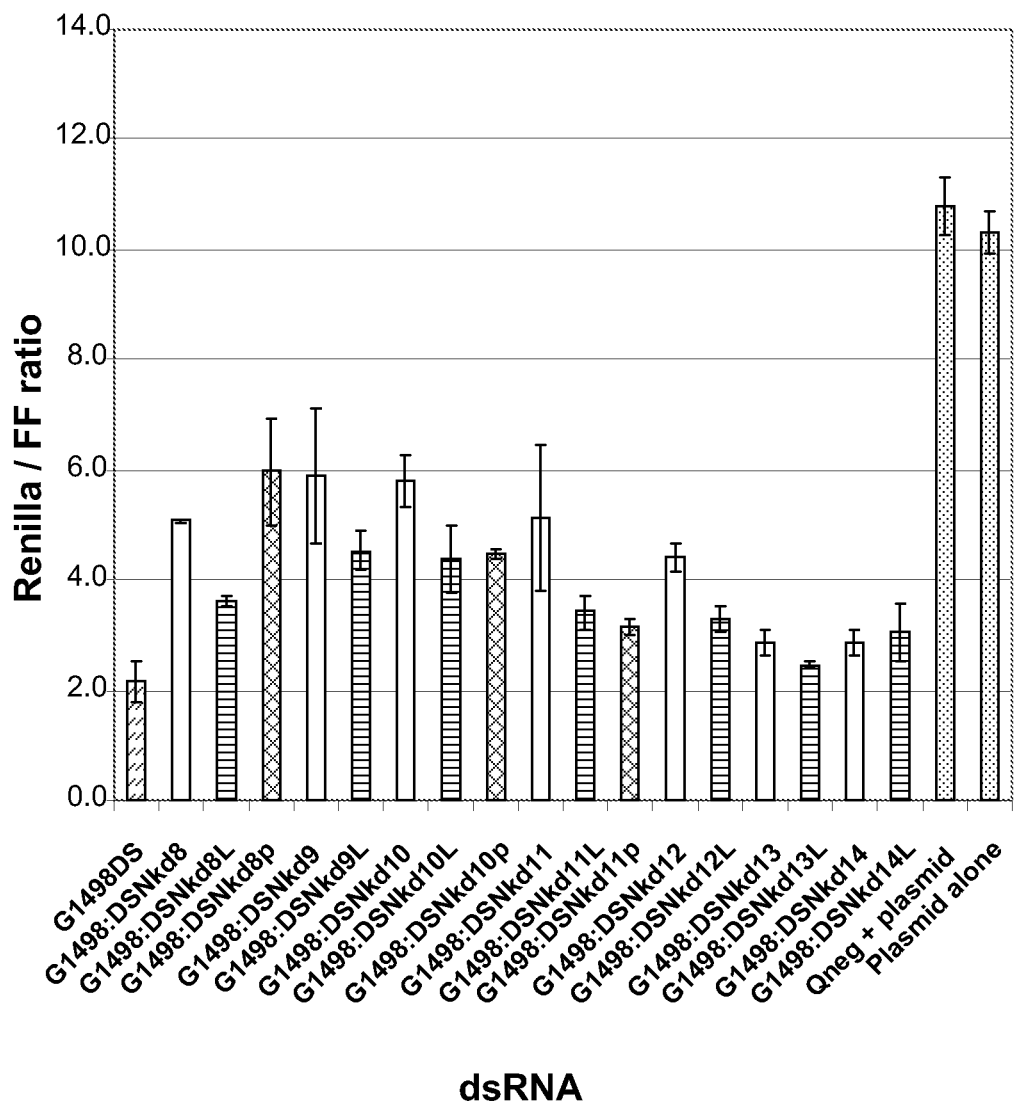
FIG. 4 shows knockdown activity of a dicer substrate influenza dsRNA G1498DS (25/27) and this sequence nicked at one of each of positions 8 to 14 of the sense strand, and shows the activity of these nicked molecules that are also phosphorylated or have a locked nucleic acid substitution.

The dual fluorescence assay of Example 2 was used to measure knockdown activity with 5 nM of the LacZ sequences and 0.5 nM of the influenza sequences. The lacZ dicer substrate (25/27, LacZ-DS) and lacZ RISC activator (21/21, LacZ) are equally active, and the LacZ-DS can be nicked in any position between 8 and 14 without affecting activity (FIG. 3). In addition, the inclusion of a ddG on the 5'-end of the 3'-most LacZ sense sequence having a nick (LacZ:DSNkd13-3' dd) or a one nucleotide gap (LacZ: DSNkd13D1-3' dd) was essentially as active as the unsubstituted sequence (FIG. 3). The influenza dicer substrate (G1498DS) nicked at any one of positions 8 to 14 was also highly active (FIG. 4). Phosphorylation of the 5'-end of the 3'-most strand of the nicked sense influenza sequence had essentially no effect on activity, but addition of a locked nucleic acid appears to improve activity.

Example 4

Mean Inhibitory Concentration of mdRNA

Figure 5:
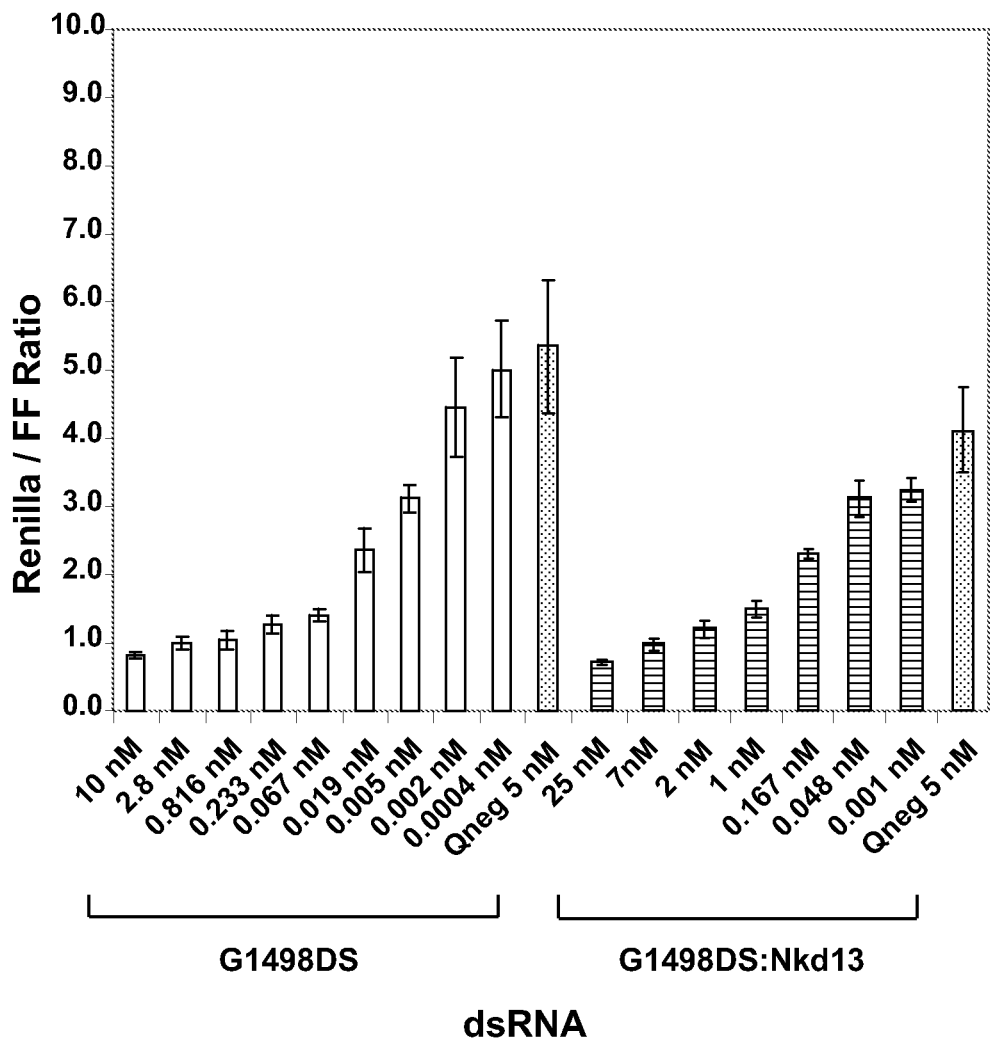
FIG. 5 shows a dose dependent knockdown activity a dicer substrate influenza dsRNA G1498DS (25/27) and this sequence nicked at position 13 of the sense strand.

In this example, a dose response assay was performed to measure the mean inhibitory concentration ($IC_{50}$) of the influenza dicer substrate dsRNA of Example 7 having a sense strand with a nick at position 12, 13, or 14, including or not a locked nucleic acid. The dual luciferase assay of Example 2 was used. The influenza dicer substrate dsRNA (G1498DS) was tested at 0.0004 nM, 0.002 nM, 0.005 nM, 0.019 nM, 0.067 nM, 0.233 nM, 0.816 nM, 2.8 nM, and 10 nM, while the mdRNA with a nick at position 13 (G1498DS:Nkd13) was tested at 0.001 nM, 0.048 nM, 0.167 nM, 1 nM, 2 nM, 7 nM, and 25 nM (see FIG. 5). Also tested were RISC activator molecules (21/21) with or without a nick at various positions, G1498DS:Nkd12, and G1498DS:Nkd14, each of the nicked versions with a locked nucleic acid as described above (data not shown). The Qneg is a negative control dsRNA.

The $IC_{50}$ of the RISC activator G1498 was calculated to be about 22 pM, while the dicer substrate G1498DS $IC_{50}$ was calculated to be about 6 pM. The $IC_{50}$ of RISC and Dicer mdRNAs range from about 200 pM to about 15 nM. The inclusion of a single locked nucleic acid reduced the $IC_{50}$ of Dicer mdRNAs by up 4 fold (data not shown). These results show that a meroduplex dsRNA having a nick or gap in any position is capable of inducing gene silencing.

Example 5

Knockdown Activity of mdRNA Having a Gap of Different Sizes and Positions

The activity of an influenza dicer substrate dsRNA having a sense strand with a gap of differing sizes and positions was examined. The influenza dicer substrate dsRNA of Example 7 was generated with a sense strand having a gap of 0 to 6 nucleotides at position 8, a gap of 4 nucleotides at position 9, a gap of 3 nucleotides at position 10, a gap of 2 nucleotides at position 11, and a gap of 1 nucleotide at position 12 (see Table 3). The Qneg is a negative control dsRNA. Each of the mdRNAs were tested at a concentration of 5 nM (data not shown) and 10 nM. The mdRNAs have the following antisense strand 5'-CAUUGUCUCCGAAGAAAUAAGAUC-CUU (SEQ ID NO:11) and nicked or gapped sense strands as shown in Table 3.

TABLE 3

| mdRNA | 5' Sense* (SEQ ID NO.) | 3' Sense (SEQ ID NO.) | Gap Pos | Gap Size | % KD |
|---|---|---|---|---|---|
| G1498:DSNkd8 | GGAUCUUA (12) | UUUCUUCGGAGACAAdTdG (13) | 8 | 0 | 67.8 |
| G1498:DSNkd8D1 | GGAUCUUA (12) | UUCUUCGGAGACAAdTdG (14) | 8 | 1 | 60.9 |
| G1498:DSNkd8D2 | GGAUCUUA (12) | UCUUCGGAGACAAdTdG (15) | 8 | 2 | 48.2 |
| G1498:DSNkd8D3 | GGAUCUUA (12) | CUUCGGAGACAAdTdG (16) | 8 | 3 | 44.1 |
| G1498:DSNkd8D4 | GGAUCUUA (12) | UUCGGAGACAAdTdG (17) | 8 | 4 | 30.8 |
| G1498:DSNkd8D5 | GGAUCUUA (12) | UCGGAGACAAdTdG (18) | 8 | 5 | 10.8 |
| G1498:DSNkd8D6 | GGAUCUUA (12) | CGGAGACAAdTdG (19) | 8 | 6 | 17.9 |
| G1498:DSNkd9D4 | GGAUCUUAU (20) | UCGGAGACAAdTdG (18) | 9 | 4 | 38.9 |

TABLE 3-continued

| mdRNA | 5' Sense* (SEQ ID NO.) | 3' Sense (SEQ ID NO.) | Gap Pos | Gap Size | % KD |
|---|---|---|---|---|---|
| G1498:DSNkd10D3 | GGAUCUUAUU (21) | UCGGAGACAAdTdG (18) | 10 | 3 | 38.4 |
| G1498:DSNkd11D2 | GGAUCUUAUUU (22) | UCGGAGACAAdTdG (18) | 11 | 2 | 46.2 |
| G1498:DSNkd12D1 | GGAUCUUAUUUC (23) | UCGGAGACAAdTdG (18) | 12 | 1 | 49.6 |
| Plasmid | — | — | — | — | 5.3 |

*G indicates a locked nucleic acid G in the 5' sense strand.

Figure 6:
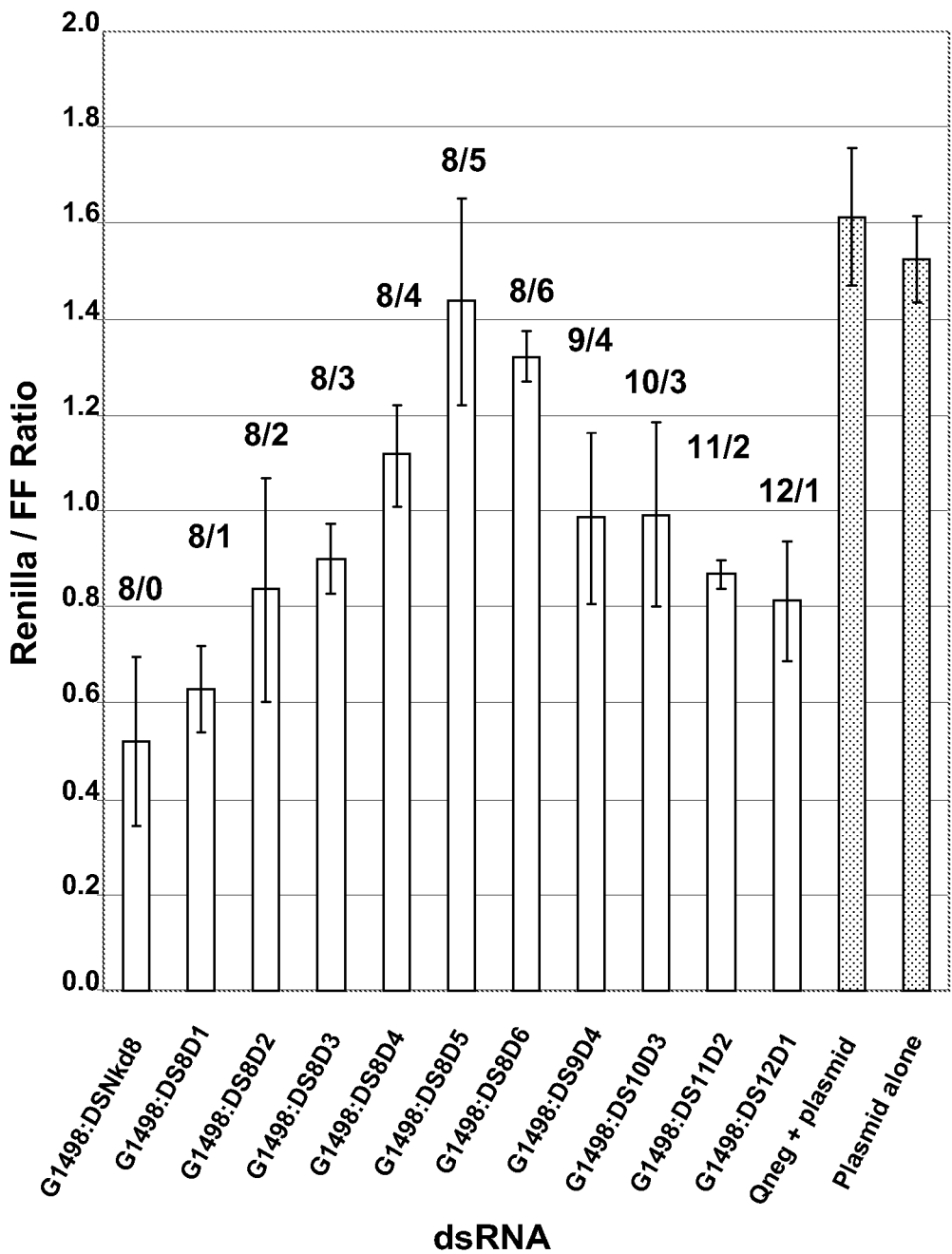
FIG. 6 shows knockdown activity of a dicer substrate influenza dsRNA G1498DS having a nick or a gap of one to six nucleotides that begins at any one of positions 8 to 12 of the sense strand.

The dual fluorescence assay of Example 2 was used to measure knockdown activity. Similar results were obtained at both the 5 nM and 10 nM concentrations. These data show that an mdRNA having a gap of up to 6 nucleotides still has activity, although having four or fewer missing nucleotides shows the best activity (see, also, FIG. 6). Thus, mdRNA having various sizes gaps that are in various different positions have knockdown activity.

To examine the general applicability of a sequence having a sense strand with a gap of differing sizes and positions, a different dsRNA sequence was tested. The lacZ RISC dsRNA of Example 1 was generated with a sense strand having a gap of 0 to 6 nucleotides at position 8, a gap of 5 nucleotides at position 9, a gap of 4 nucleotides at position 10, a gap of 3 nucleotides at position 11, a gap of 2 nucleotides at position 12, a gap of 1 nucleotide at position 12, and a nick (gap of 0) at position 14 (see Table 4). The Qneg is a negative control dsRNA. Each of the mdRNAs was tested at a concentration of 5 nM (data not shown) and 25 nM. The lacZ mdRNAs have the following antisense strand 5'-AAAUCGCUGAUUUGU-GUAGdTdTUAAA (SEQ ID NO:2) and nicked or gapped sense strands as shown in Table 4.

Figure 7:
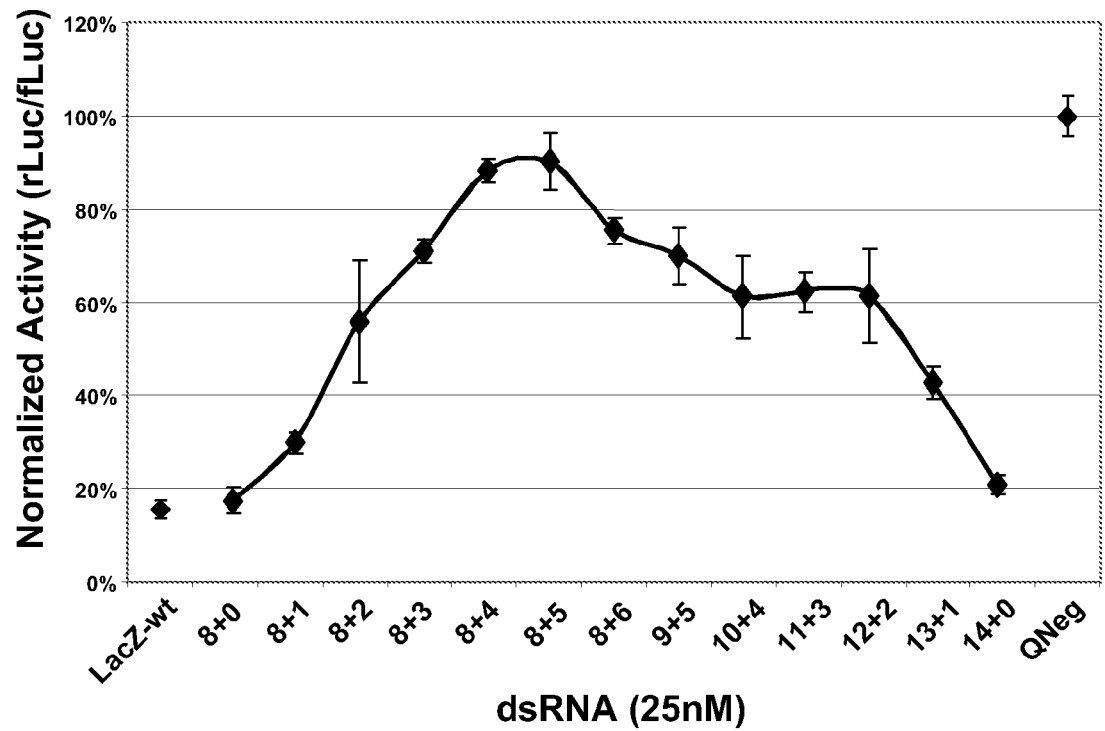
FIG. 7 shows knockdown activity of a LacZ RISC dsRNA having a nick or a gap of one to six nucleotides that begins at any one of positions 8 to 14 of the sense strand.

The dual fluorescence assay of Example 2 was used to measure knockdown activity. FIG. 7 shows that an mdRNA having a gap of up to 6 nucleotides has substantial activity and the position of the gap may affect the potency of knockdown. Thus, mdRNA having various sizes gaps that are in various different positions and in different mdRNA sequences have knockdown activity.

Example 6

Knockdown Activity of Substituted mdRNA

The activity of an influenza dsRNA RISC sequences having a nicked sense strand and the sense strands having locked nucleic acid substitutions were examined. The influenza RISC sequence G1498 of Example 2 was generated with a sense strand having a nick at positions 8 to 14 counting from the 5'-end. Each sense strand was substituted with one or two locked nucleic acids as shown in Table 5. The Qneg and Plasmid are negative controls. Each of the mdRNAs was tested at a concentration of 5 nM. The antisense strand used was 5'-CUCCGAAGAAAUAAGAUCCdTdT (SEQ ID NO:8).

TABLE 4

| mdRNA | 5' Sense* (SEQ ID NO.) | 3' Sense* (SEQ ID NO.) | Gap Pos | Gap Size |
|---|---|---|---|---|
| LacZ:Nkd8 | CUACACAA (24) | AUCAGCGAUUUdTdT (25) | 8 | 0 |
| LacZ:Nkd8D1 | CUACACAA (24) | UCAGCGAUUUdTdT (26) | 8 | 1 |
| LacZ:Nkd8D2 | CUACACAA (24) | CAGCGAUUUdTdT (27) | 8 | 2 |
| LacZ:Nkd8D3 | CUACACAA (24) | AGCGAUUUdTdT (28) | 8 | 3 |
| LacZ:Nkd8D4 | CUACACAA (24) | GCGAUUUdTdT (29) | 8 | 4 |
| LacZ:Nkd8D5 | CUACACAA (24) | CGAUUUdTdT (30) | 8 | 5 |
| LacZ:Nkd8D6 | CUACACAA (24) | GAUUUdTdT (31) | 8 | 6 |
| LacZ:Nkd9D5 | CUACACAAA (32) | GAUUUdTdT (31) | 9 | 5 |
| LacZ:Nkd10D4 | CUACACAAAU (33) | GAUUUdTdT (31) | 10 | 4 |
| LacZ:Nkd11D3 | CUACACAAAUC (34) | GAUUUdTdT (31) | 11 | 3 |
| LacZ:Nkd12D2 | CUACACAAAUCA (35) | GAUUUdTdT (31) | 12 | 2 |
| LacZ:Nkd13D1 | CUACACAAAUCAG (36) | GAUUUdTdT (31) | 13 | 1 |
| LacZ:Nkd14 | CUACACAAAUCAGC (37) | GAUUUdTdT (31) | 14 | 0 |

*A indicates a locked nucleic acid A in each sense strand.

TABLE 5

| mdRNA | 5' Sense* (SEQ ID NO.) | 3' Sense* (SEQ ID NO.) | Nick Pos | % KD |
|---|---|---|---|---|
| G1498-wt | GGAUCUUAUUUCUUCGGAGdTdT (7) | — | — | 85.8 |
| G1498-L | GGAUCUUAUUUCUUCGGAGdTdT (61) | — | — | 86.8 |
| G1498:Nkd8-1 | GGAUCUUA (12) | UUUCUUCGGAGdTdT (47) | 8 | 36.0 |
| G1498:Nkd8-2 | GGAUCUUA (40) | UUUCUUCGGAGdTdT (54) | 8 | 66.2 |
| G1498:Nkd9-1 | GGAUCUUAU (20) | UUCUUCGGAGdTdT (48) | 9 | 60.9 |
| G1498:Nkd9-2 | GGAUCUUAU (41) | UUCUUCGGAGdTdT (55) | 9 | 64.4 |
| G1498:Nkd10-1 | GGAUCUUAUU (21) | UCUUCGGAGdTdT (49) | 10 | 58.2 |
| G1498:Nkd10-2 | GGAUCUUAUU (42) | UCUUCGGAGdTdT (56) | 10 | 68.5 |
| G1498:Nkd11-1 | GGAUCUUAUUU (22) | CUUCGGAGdTdT (50) | 11 | 75.9 |
| G1498:Nkd11-2 | GGAUCUUAUUU (43) | CUUCGGAGdTdT (57) | 11 | 67.1 |
| G1498:Nkd12-1 | GGAUCUUAUUUC (23) | UUCGGAGdTdT (51) | 12 | 59.9 |
| G1498:Nkd12-2 | GGAUCUUAUUUC (44) | UUCGGAGdTdT (58) | 12 | 72.8 |
| G1498:Nkd13-1 | GGAUCUUAUUUCU (38) | UCGGAGdTdT (52) | 13 | 37.1 |
| G1498:Nkd13-2 | GGAUCUUAUUUCU (45) | UCGGAGdTdT (59) | 13 | 74.3 |
| G1498:Nkd14-1 | GGAUCUUAUUUCUU (39) | CGGAGdTdT (53) | 14 | 29.0 |
| G1498:Nkd14-2 | GGAUCUUAUUUCUU (46) | CGGAGdTdT (60) | 14 | 60.2 |
| Qneg | — | — | — | 0 |
| Plasmid | — | — | — | 3.6 |

*Nucleotides that are bold and underlined are locked nucleic acids.

Figure 8:
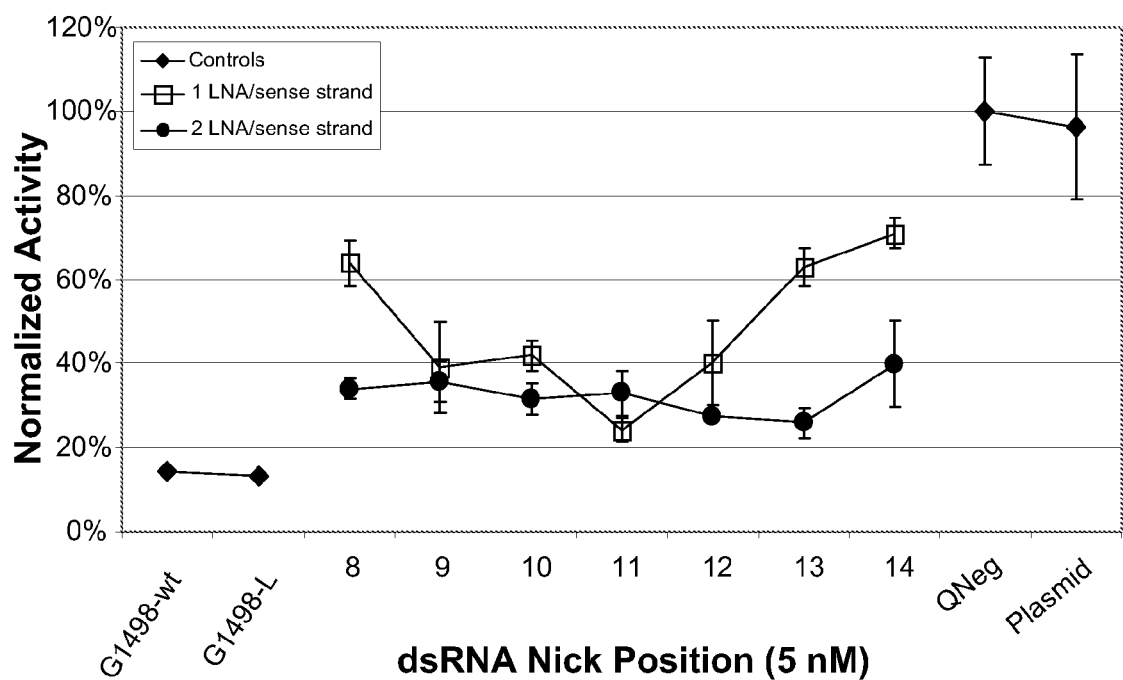
FIG. 8 shows knockdown activity of an influenza RISC dsRNA having a nick at any one of positions 8 to 14 of the sense strand and further having one or two locked nucleic acids per sense strand.

The dual fluorescence assay of Example 2 was used to measure knockdown activity. These data show that increasing the number of locked nucleic acid substitutions tends to increase activity of an mdRNA having a nick at any of a number of positions. The single locked nucleic acid per sense strand is most active when the nick is at position 11 (see FIG. 8). But, multiple locked nucleic acids on each sense strand make mdRNA having a nick at any position as active as the most optimal nick position with a single substitution (i.e., position 11) (FIG. 8). Thus, mdRNA having duplex stabilizing modifications make mdRNA essentially equally active regardless of the nick position.

Figure 9:
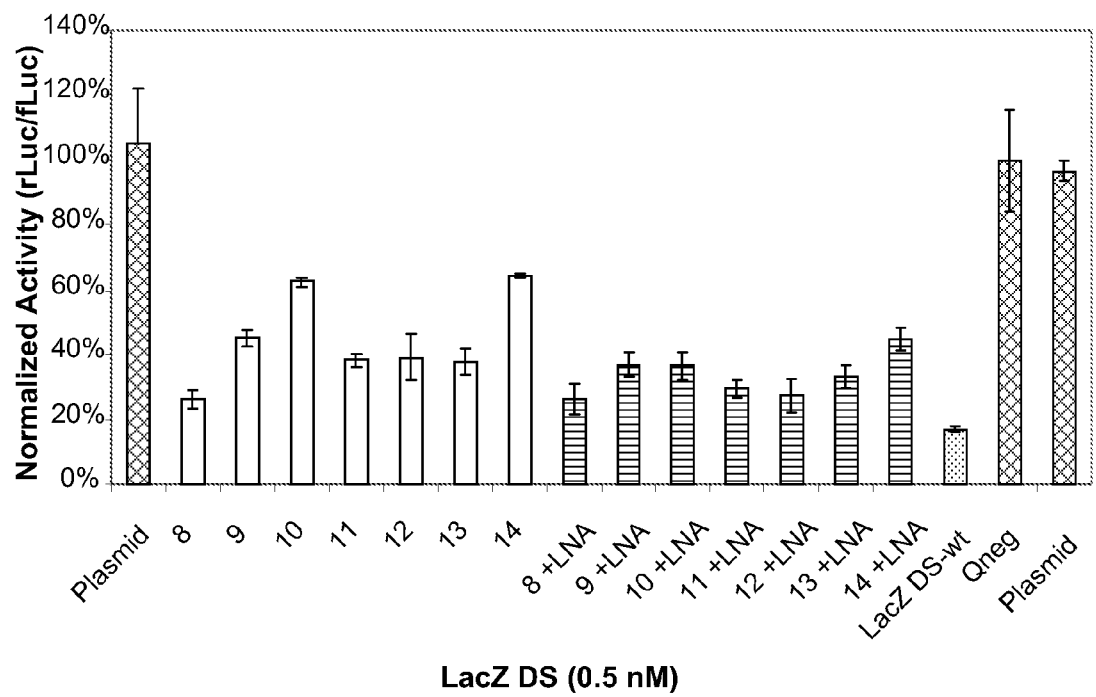
FIG. 9 shows knockdown activity of a LacZ dicer substrate dsRNA having a nick at any one of positions 8 to 14 of the sense strand as compared to the same nicked dicer substrates but having a locked nucleic acid substitution.

Similar results were observed when locked nucleic acid substitutions were made in the LacZ dicer substrate mdRNA of Example 1 (SEQ ID NOS:3 and 4). The lacZ dicer was nicked at positions 8 to 14, and a duplicate set of nicked LacZ dicer molecules were made with the exception that the A at position 3 (from the 5'-end) of the 5' sense strand was substituted for a locked nucleic acid A (LNA-A). As is evident from FIG. 11, most of the nicked lacZ dicer molecules containing LNA-A were as potent in knockdown activity as the unsubstituted lacZ dicer (see FIG. 9).

Example 7 mdRNA Knockdown of Influenza Virus Titer

The activity of a dicer substrate nicked dsRNA in reducing influenza virus titer as compared to a wild-type dsRNA (i.e., not having a nick) was examined. The influenza dicer substrate sequence (25/27) is as follows:

```
                                        (SEQ ID NO: 62)
Sense       5'-GGAUCUUAUUUCUUCGGAGACAAdTdG (SEQ ID NO: 11)
Antisense   5'-CAUUGUCUCCGAAGAAAUAAGAUCCUU
```

These mdRNA sequences are nicked after position 12, 13, and 14, respectively, as counted from the 5'-end, and each sense strand also has a G at position 2 substituted with locked nucleic acid G.

For the viral infectivity assay, Vero cells were seeded at 6.5×10⁴ cells/well the day before transfection in 500 µA 10% FBS/DMEM media per well. Samples of 100, 10, 1, 0.1, and 0.01 nM stock of each dsRNA were complexed with 1.0 µl (1 mg/ml stock) of Lipofectamine™ 2000 (Invitrogen, Carlsbad, Calif.) and incubated for 20 minutes at room temperature in 150 µl OPTIMEM (total volume) (Gibco, Carlsbad, Calif.). Vero cells were washed with OPTIMEM, and 150 µl of the transfection complex in OPTIMEM was then added to each well containing 150 µl of OPTIMEM media. Triplicate wells were tested for each condition. An additional control well with no transfection condition was prepared. Three hours post transfection, the media was removed. Each well was washed once with 200 µl *PBS containing* 0.3% BSA and 10 mM HEPES/PS. Cells in each well were infected with WSN strain of influenza virus at an MOI 0.01 in 200 µl of infection media containing 0.3% BSA/10 mM HEPES/PS and 4 µg/ml trypsin. The plate was incubated for 1 hour at 37° C. Unadsorbed virus was washed off with the 200 µl of infection media and discarded, then 400 µl *DMEM containing* 0.3% BSA/10 mM HEPES/PS and 4 µg/ml trypsin was added to each well. The plate was incubated at 37° C., 5% $CO_2$ for 48 hours, then 50 µl supernatant from each well was tested in duplicate by $TCID_{50}$ assays (Tissue-Culture Infective Dose 50, WHO protocol) in MDCK cells and titers were estimated using the Spearman and Karber formula.

Figure 10:
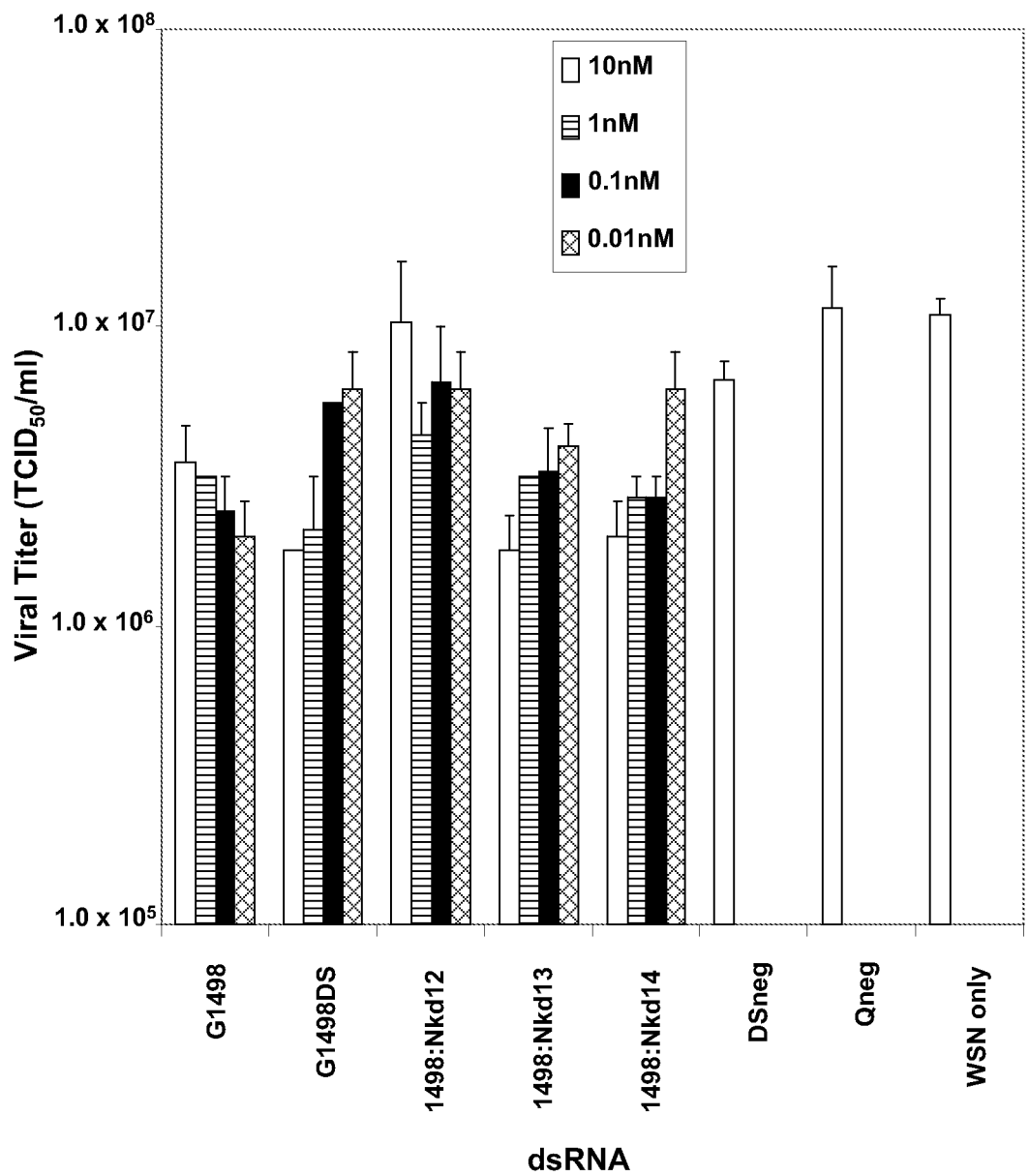
FIG. 10 shows the dose-dependent reduction in WSN influenza viral titers using influenza specific mdRNA as measured by $TCID_{50}$.
Figure 11:
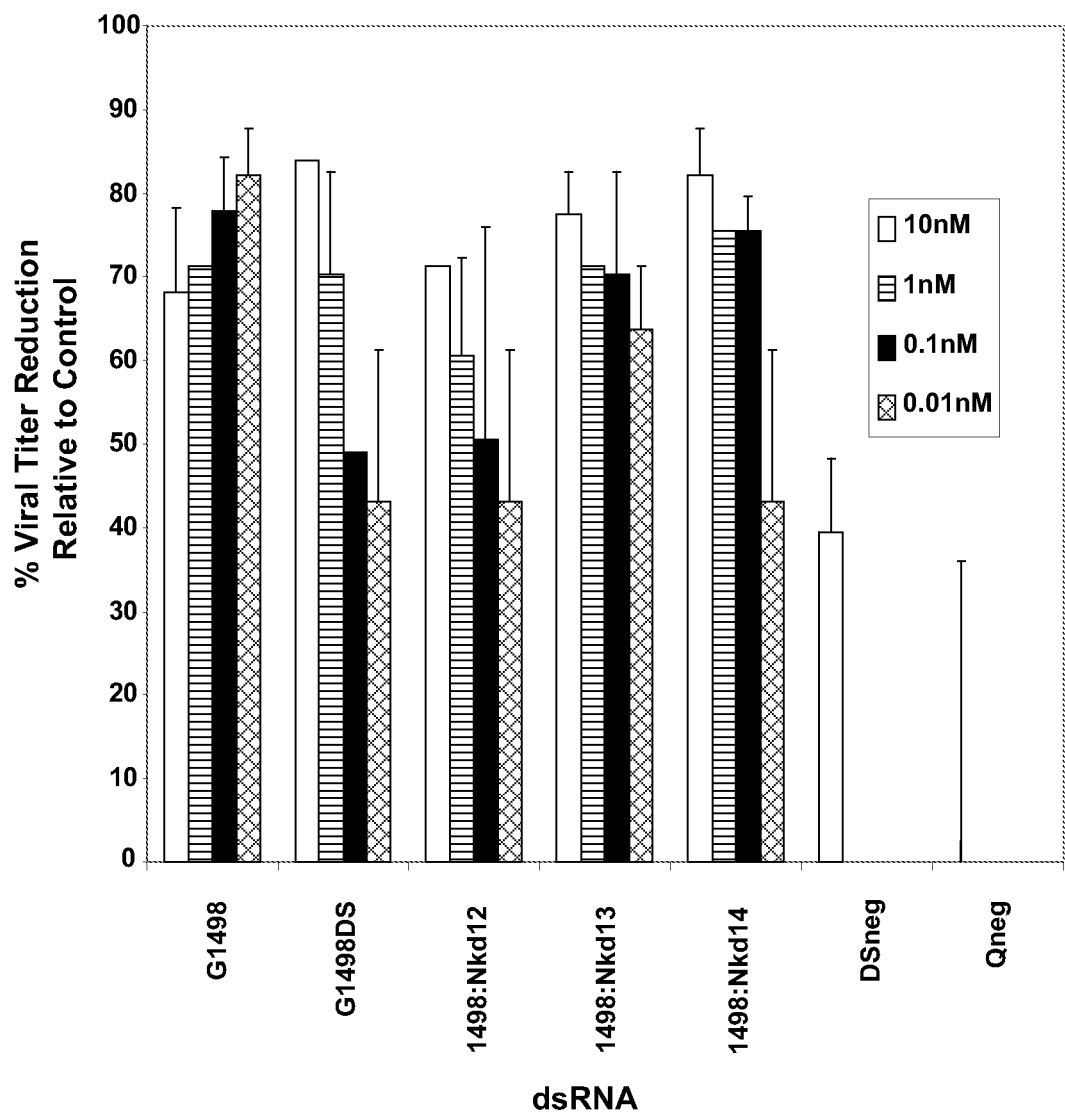
FIG. 11 shows the percent knockdown in influenza viral titers using influenza specific mdRNA against influenza strain WSN.

The results show that all of the G1498 nicked mdRNAs caused a 10-fold reduction in influenza viral titers (FIG. 10). That is, these mdRNAs show about a 50% to 60% viral titer knockdown, even at a concentration as low as 10 µM (FIG. 11).

Figure 12:
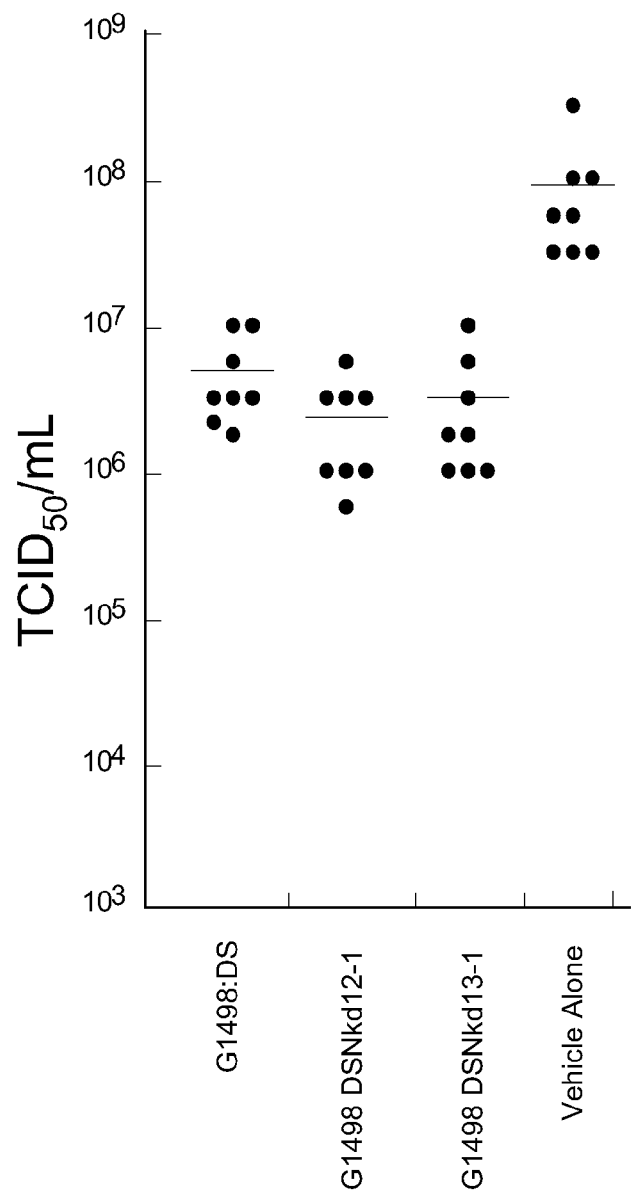
FIG. 12 shows the in vivo reduction in PR8 influenza viral titers using influenza specific mdRNA as measured by $TCID_{50}$.

An in vivo influenza mouse model was also used to examine the activity of a dicer substrate nicked dsRNA in reducing influenza virus titer as compared to a wild-type dsRNA (i.e., not having a nick). Female BALB/c mice (age 8-10 weeks with 5-10 mice per group) were dosed intranasally with 120 nmol/kg/day dsRNA (formulated in C12-norArg($NH_3$+ C—)-C12/DSPE-PEG2000/DSPC/cholesterol at a ratio of 30:1:20:49) for three consecutive days before intranasal challenge with influenza strain PR8 (20 PFU/mouse). Two days after infection, whole lungs are harvested from each mouse and placed in a solution of PBS/0.3% BSA with antibiotics, homogenize, and measure the viral titer ($TCID_{50}$). Doses were well tolerated by the mice, indicated by less than 2% body weight reduction in any of the dose groups. The mdRNAs tested exhibit similar, if not slightly greater, virus reduction in vivo as compared to unmodified and unnicked G1498 dicer substrate (see FIG. 12). Hence, mdRNA are active in vivo.

Example 8

Effect of mdRNA on Cytokine Induction

The effect of the mdRNA structure on cytokine induction in vivo was examined Female BALB/c mice (age 7-9 weeks) were dosed intranasally with about 50 µM dsRNA (formulated in C12-norArg($NH_3$+Cl—)-C12/DSPE-PEG2000/DSPC/cholesterol at a ratio of 30:1:20:49) or with 605 nmol/kg/day naked dsRNA for three consecutive days. About four hours after the final dose is administered, the mice were sacrificed to collect bronchoalveolar fluid (BALF), and collected blood is processed to serum for evaluation of the cytokine response. Bronchial lavage was performed with 0.5 mL ice-cold 0.3% BSA in saline two times for a total of 1 mL. BALF was spun and supernatants collected and frozen until cytokine analysis. Blood was collected from the vena cava immediately following euthanasia, placed into serum separator tubes, and allowed to clot at room temperature for at least 20 minutes. The samples were processed to serum, aliquoted into Millipore ULTRAFREE 0.22 µm filter tubes, spun at 12,000 rpm, frozen on dry ice, and then stored at –70° C. until analysis. Cytokine analysis of BALF and plasma were performed using the Procarta™ mouse 10-Plex Cytokine Assay Kit (Panomics, Fremont, Calif.) on a Bio-Plex™ array reader. Toxicity parameters were also measured, including body weights prior to the first dose on day 0 and again on day 3, just prior to euthanasia. Spleens were harvested, weighed, and weights were normalized to final body weights. The results are provided in Table 6.

TABLE 6

In vivo Cytokine Induction by Naked mdRNA

| Cytokine | | G1498 | G1498:Nkd 11-1 | G1498:DS | G1498:DSNkd 12-1 | G1498:DSNkd 13-1 | G1498:DSNkd 14-1 |
|---|---|---|---|---|---|---|---|
| IL-6 | Conc (pg/mL) | 90.68 | 10.07 | 77.35 | 17.17 | 18.21 | 38.59 |
| | Fold decrease | — | 9 | — | 5 | 4 | 2 |
| IL-12 (p40) | Conc (pg/mL) | 661.48 | 20.32 | 1403.61 | 25.07 | 37.70 | 57.02 |
| | Fold decrease | — | 33 | — | 56 | 37 | 25 |
| TNFα | Conc (pg/mL) | 264.49 | 25.59 | 112.95 | 20.52 | 29.00 | 64.93 |
| | Fold decrease | — | 10 | — | 6 | 4 | 2 |

The mdRNA (RISC or dicer sized) induced cytokines to lesser extent than the intact (i.e., not nicked) parent molecules. The decrease in cytokine induction was greatest when looking at IL-12 (p40), the cytokine with consistently the highest levels of induction of the 10 cytokine multiplex assay. For the mdRNA, the decrease in IL-12 (p40) ranges from 25- to 56-fold, while the reduction in either IL-6 or TNFα induction was more modest (the decrease in these two cytokines ranges from 2- to 10-fold). Thus, the mdRNA structure appears to provide an advantage in vivo in that cytokine induction is minimized compared to unmodified dsRNA.

Similar results were obtained with the formulated mdRNA, although the reduction in induction was not as prominent. In addition, the presence or absence of a locked nucleic acid has no effect on cytokine induction. These results are shown in Table 7.

TABLE 7

In vivo Cytokine Induction by Formulated mdRNA

| Cytokine | | G1498:DS | G1498:Nkd 12-1 | G1498:Nkd 13-1 | G1498:DSNkd 14-1 | G1498:DSNkd 13 |
|---|---|---|---|---|---|---|
| IL-6 | Conc (pg/mL) | 29.04 | 52.95 | 10.28 | 7.79 | 44.29 |
| | Fold decrease | — | –1.8 | 3 | 4 | –1.5 |
| IL-12 (p40) | Conc (pg/mL) | 298.93 | 604.24 | 136.45 | 126.71 | 551.49 |
| | Fold decrease | — | 0 | 2 | 2 | 1 |
| TNFα | Conc (pg/mL) | 13.49 | 21.35 | 3.15 | 3.15 | 18.69 |
| | Fold decrease | — | –1.6 | 4 | 4 | 1.4 |

The teachings of all of references cited herein including patents, patent applications and journal articles are incorporated herein in their entirety by reference. Although the foregoing disclosure has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. It is noted, however, that the various publications discussed herein are incorporated solely for their disclosure prior to the filing date of the present application, and the inventors reserve the right to antedate such disclosure by virtue of prior invention.

What is claimed is:

1. A ribonucleic acid comprising an A strand, which is complementary to a target RNA, the A strand having a length from 15 to 30 nucleotides, an S1 strand having a length from 5 to 25 nucleotides, and an S2 strand having a length from 5 to 25 nucleotides, wherein:
   (a) the S1 strand and the A strand anneal to form a first double-stranded region from 5 to 13 base pairs in length;
   (b) the S2 strand and the A strand anneal to form a second double-stranded region from 6 to 25 base pairs in length;
   (c) the sum of the lengths of the first double-stranded region and the second double-stranded region is from 19 to 30 base pairs;
   (d) the first double-stranded region is separated from the second double stranded region by a gap, the gap being from 1 to 10 unpaired nucleotides of the A strand, and the gap is between the first double-stranded region and the second double-stranded region; and
   (e) the ribonucleic acid has 0, 1, or 2 overhangs, wherein the overhangs are not in the gap and each are independently from 1 to 5 nucleotides in length.

2. A ribonucleic acid comprising an A strand, an S1 strand, and an S2 strand, wherein:
   the A strand is an antisense strand having a length from 18 to 25 nucleotides;
   the S1 strand has a length from 5 to 15 nucleotides;
   the S2 strand has a length from 3 to 13 nucleotides;
   the sum of the lengths of the S1 strand and the S2 strand is from 18 to 25 nucleotides;
   the A strand, S1 strand, and S2 strand form a first double-stranded region and a second double-stranded region;
   the first double-stranded region is spaced apart from the second double stranded region by a gap, the gap being a single-stranded region of the A strand between the first double-stranded region and the second double-stranded region, wherein the gap is from 1 to 10 nucleotides in length; and
   the ribonucleic acid has 0, 1, or 2 overhangs, wherein the overhangs are not in the gap and each are independently from 1 to 4 nucleotides in length.

3. A ribonucleic acid comprising an A strand, which is complementary to a target RNA, the A strand having a length from 16 to 30 nucleotides, an S1 strand having a length from 5 to 25 nucleotides, and an S2 strand having a length from 15 to 25 nucleotides, wherein:
   (a) the S1 strand and the A strand anneal to form a first double-stranded region;
   (b) the S2 strand and the A strand anneal to form a second double-stranded region;
   (c) at least one double-stranded region is from 5 base pairs to 13 base pairs in length;
   (d) the first double-stranded region is separated from the second double stranded region by a gap, the gap being from 1 to 10 unpaired nucleotides of the A strand, and the gap is between the first double-stranded region and the second double-stranded region; and
   (e) the ribonucleic acid has 0, 1, or 2 overhangs, wherein the overhangs are not in the gap and each are independently from 1 to 5 nucleotides in length.

4. A ribonucleic acid comprising an A strand, which is complementary to a target RNA, the A strand having a length from 15 to 30 nucleotides, an S1 strand having a length from 6 to 25 nucleotides, and an S2 strand having a length from 6 to 25 nucleotides, wherein:
(a) the S1 strand and the A strand anneal to form a first double-stranded region from 5 to 13 base pairs in length;
(b) the S2 strand and the A strand anneal to form a second double-stranded region;
(c) the ribonucleic acid has a nick between the first double-stranded region and the second double-stranded region; and
(d) the ribonucleic acid has 0, 1, or 2 overhangs, wherein the overhangs are not in the gap and each are independently from 1 to 5 nucleotides in length.

5. A ribonucleic acid comprising an A strand, an S1 strand, and an S2 strand, wherein:
the A strand is an antisense strand having a length from 18 to 25 nucleotides;
the S1 strand has a length from 5 to 15 nucleotides;
the S2 strand has a length from 3 to 13 nucleotides or less;
the sum of the lengths of the S1 strand and the S2 strand is from 18 to 25 nucleotides;
the A strand, S1 strand, and S2 strand form a first double-stranded region and a second double-stranded region;
the ribonucleic acid has a nick between the first double-stranded region and the second double-stranded region; and
the ribonucleic acid has 0, 1, or 2 overhangs, wherein the overhangs are not in the gap and each are independently from 1 to 4 nucleotides in length.

6. A ribonucleic acid comprising an A strand, which is complementary to a target RNA, the A strand having a length from 16 to 30 nucleotides, an S1 strand having a length from 5 to 25 nucleotides, and an S2 strand having a length from 15 to 25 nucleotides, wherein:
(a) the S1 strand and the A strand anneal to form a first double-stranded region;
(b) the S2 strand and the A strand anneal to form a second double-stranded region;
(c) at least one double-stranded region is from 5 base pairs to 13 base pairs in length;
(d) the ribonucleic acid has a nick between the first double-stranded region and the second double-stranded region; and
(e) the ribonucleic acid has 0, 1, or 2 overhangs, wherein the overhangs are not in the gap and each are independently from 1 to 5 nucleotides in length.

7. The ribonucleic acid of claim 1, wherein the gap has a length of from 1 to 6 unpaired nucleotides.

8. The ribonucleic acid of claim 1, wherein the gap has a length of 1 unpaired nucleotide.

9. The ribonucleic acid of claim 1, wherein the overhangs are 3' overhangs, and each overhang has a length of from 1 to 4 nucleotides.

10. The ribonucleic acid of claim 1, wherein a 3'-end that is not part of the gap of the ribonucleic acid is a blunt end.

11. The ribonucleic acid of claim 1, wherein the A strand has a length of from 19 to 25 nucleotides.

12. The ribonucleic acid of claim 1, wherein the A strand has a length of from 25 to 30 nucleotides.

13. The ribonucleic acid of claim 1, wherein at least one nucleotide has a modified sugar.

14. The ribonucleic acid of claim 1, wherein at least one nucleotide has a 2' sugar bridge.

15. The ribonucleic acid of claim 1, wherein at least one nucleotide has a modified internucleoside linkage.

16. The ribonucleic acid of claim 1, wherein at least one nucleotide is a locked nucleic acid nucleotide.

17. The ribonucleic acid of claim 1, wherein at least one nucleotide is a locked nucleic acid nucleotide, or at least one nucleotide has a 2'-sugar substitution, or at least one nucleotide has a G clamp, or at least one nucleotide has a modified internucleoside linkage, or at least one nucleotide has a terminal cap substituent, at least one nucleotide has a 2'-methoxy or fluoro modification, or at least one nucleotide has a phosphorothioate internucleoside linkage, or any combination thereof.

18. The ribonucleic acid of claim 1, wherein at least one pyrimidine of the ribonucleic acid comprises a pyrimidine nucleoside according to Formula I or II:

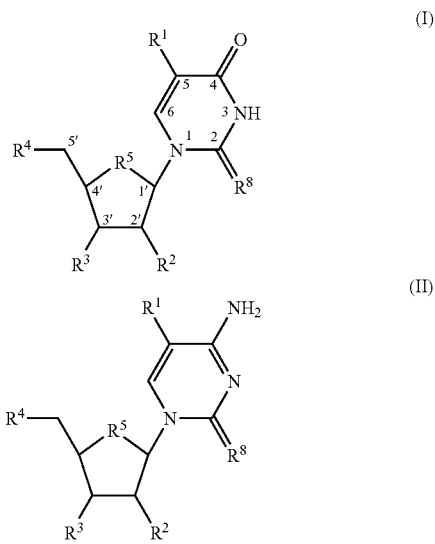

wherein:
$R^1$ and $R^2$ are each independently a —H, —OH, —OCH$_3$, —OCH$_2$, OCH$_2$CH$_3$, —OCH$_2$CH$_2$OCH$_3$, halogen, substituted or unsubstituted $C_1$-$C_{10}$ alkyl, alkoxy, alkoxyalkyl, hydroxyalkyl, carboxyalkyl, alkylsulfonylamino, aminoalkyl, dialkylamino, alkylaminoalkyl, dialkylaminoalkyl, haloalkyl, trifluoromethyl, cycloalkyl, (cycloalkyl)alkyl, substituted or unsubstituted $C_2$-$C_{10}$ alkenyl, substituted or unsubstituted —O-allyl, —O—CH$_2$CH═CH$_2$, —O—CH═CHCH$_3$, substituted or unsubstituted $C_2$-$C_{10}$ alkynyl, carbamoyl, carbamyl, carboxy, carbonylamino, substituted or unsubstituted aryl, substituted or unsubstituted aralkyl, —NH$_2$, —NO$_2$, —C≡N, or heterocyclo group,
$R^3$ and $R^4$ are each independently a hydroxyl, a protected hydroxyl, a phosphate, or an internucleoside linking group, and
$R^5$ and $R^8$ are independently O or S.

19. The ribonucleic acid of claim 18, wherein at least one nucleoside is according to Formula I in which $R^1$ is methyl and $R^2$ is —OH.

20. The ribonucleic acid of claim 18, wherein at least one nucleoside is according to Formula I in which $R^2$ is —OCH$_3$ or fluoro.

21. A pharmaceutical composition comprising the ribonucleic acid according to claim 1 and a pharmaceutically acceptable carrier, diluent, excipient, adjuvant, emulsifier, buffer, stabilizer, or preservative.

22. The pharmaceutical composition of claim 21 further comprising a liposome, a hydrogel, a cyclodextrin, a biodegradable nanocapsule, a bioadhesive microsphere, or a proteinaceous vector.

* * * * *